US012709596B2

(12) United States Patent
Holmes et al.

(10) Patent No.: US 12,709,596 B2
(45) **Date of Patent: *Aug. 18, 2026**

(54) MOLECULES

(71) Applicant: ENA Respiratory Pty Ltd, Sydney (AU)

(72) Inventors: Ian Holmes, Melbourne (AU); Weiguang Zeng, Melbourne (AU); David Jackson, Melbourne (AU); Christophe Demaison, Melbourne (AU); Grant Mclachlan, Melbourne (AU)

(73) Assignee: ENA Respiratory Pty Ltd, Sydney (AU)

( * ) Notice: Subject to any disclaimer, the term of this patent is extended or adjusted under 35 U.S.C. 154(b) by 954 days.

This patent is subject to a terminal disclaimer.

(21) Appl. No.: 17/622,451

(22) PCT Filed: Jun. 26, 2020

(86) PCT No.: PCT/AU2020/050660

§ 371 (c)(1),
(2) Date: Dec. 23, 2021

(87) PCT Pub. No.: WO2020/257870

PCT Pub. Date: Dec. 30, 2020

(65) Prior Publication Data

US 2022/0388950 A1 Dec. 8, 2022

(30) Foreign Application Priority Data

Jun. 26, 2019 (AU) ................................ 2019902231
Dec. 20, 2019 (AU) ................................ 2019904862

(51) Int. Cl.
*C07C 321/14* (2006.01)
*A61K 47/60* (2017.01)
(Continued)

(52) U.S. Cl.
CPC ............ *C07C 321/14* (2013.01); *A61K 47/60* (2017.08); *A61K 47/64* (2017.08); *A61P 31/12* (2018.01);
(Continued)

(58) Field of Classification Search
None
See application file for complete search history.

(56) References Cited

U.S. PATENT DOCUMENTS 5,497,763 A 3/1996 Lloyd et al.
5,544,646 A 8/1996 Lloyd et al.
(Continued)

FOREIGN PATENT DOCUMENTS

AU 2014202674 A1 6/2014
EP 1550458 A1 7/2005
(Continued)

OTHER PUBLICATIONS

Alfredo et al., Pathophysiology of viral-induced exacerbations of COPD. International Journal of COPD. 2007;2 (4):477-483.
(Continued)

*Primary Examiner* — Amy C Bonaparte
(74) *Attorney, Agent, or Firm* — McCarter & English, LLP; Michael J. DeGrazia; Sujatha Rochford

(57) ABSTRACT

The present invention relates to TLR2 agonist compounds and their compositions, and the use of such compounds and compositions in the prevention and/or treatment of respiratory infections, or diseases or conditions associated with viral or bacterial infections.

20 Claims, 4 Drawing Sheets

Gene-reporter luciferase assay

(51) Int. Cl.

| | |
|---|---|
| ***A61K 47/64*** | (2017.01) |
| ***A61P 31/12*** | (2006.01) |
| ***C07K 5/083*** | (2006.01) |
| ***C08G 65/334*** | (2006.01) |

(52) U.S. Cl.

CPC .......... *C07K 5/081* (2013.01); *C08G 65/3348* (2013.01)

(56) References Cited

U.S. PATENT DOCUMENTS

| | | | | |
|---|---|---|---|---|
| 5,660,166 | A | 8/1997 | Lloyd et al. | |
| 5,718,222 | A | 2/1998 | Lloyd et al. | |
| 7,316,996 | B2 | 1/2008 | Muhlradt et al. | |
| 8,883,174 | B2 | 11/2014 | Dickey et al. | |
| 8,986,700 | B2 | 3/2015 | Jackson et al. | |
| 9,089,508 | B2 | 7/2015 | Jackson et al. | |
| 9,676,819 | B2 | 6/2017 | Jackson et al. | |
| 9,889,195 | B2 | 2/2018 | Jackson et al. | |
| 10,406,100 | B2 | 9/2019 | Jackson et al. | |
| 11,351,114 | B2 | 6/2022 | Jackson et al. | |
| 12,017,979 | B2 * | 6/2024 | Holmes | A61K 47/64 |
| 12,195,557 | B2 * | 1/2025 | Jackson | C07K 5/0606 |
| 2004/0191270 | A1 | 9/2004 | Drane et al. | |
| 2007/0066534 | A1 | 3/2007 | Jackson et al. | |
| 2008/0069831 | A1 | 3/2008 | Duke et al. | |
| 2008/0069832 | A1 | 3/2008 | Chomez et al. | |
| 2009/0257980 | A1 | 10/2009 | Davies et al. | |
| 2010/0129385 | A1 | 5/2010 | Jackson et al. | |
| 2010/0310595 | A1 | 12/2010 | Jackson et al. | |
| 2011/0280899 | A1 | 11/2011 | Jackson et al. | |
| 2012/0064109 | A1 | 3/2012 | Jackson et al. | |
| 2013/0230544 | A1 | 9/2013 | Jackson et al. | |
| 2015/0150966 | A1 | 6/2015 | Jackson et al. | |
| 2020/0147028 | A1 | 5/2020 | Bartlett et al. | |
| 2021/0177795 | A1 | 6/2021 | Jackson | |
| 2021/0230217 | A1 | 7/2021 | Jackson et al. | |
| 2022/0347146 | A1 | 11/2022 | Demaison et al. | |
| 2023/0043518 | A1 | 2/2023 | Demaison et al. | |
| 2023/0226004 | A1 | 7/2023 | Tsitoura et al. | |
| 2023/0257345 | A1 | 8/2023 | Holmes et al. | |
| 2023/0278954 | A1 | 9/2023 | McLachlan | |
| 2025/0066416 | A1 | 2/2025 | Jackson et al. | |

FOREIGN PATENT DOCUMENTS

| | | | |
|---|---|---|---|
| EP | 1666056 | A1 | 6/2006 |
| EP | 3728289 | A1 | 10/2020 |
| JP | 2016-216593 | A | 12/2016 |
| WO | WO-2001/037869 | A1 | 5/2001 |
| WO | WO-2001/090129 | A2 | 11/2001 |
| WO | WO-2004/014956 | A1 | 2/2004 |
| WO | WO-2004/014957 | A1 | 2/2004 |
| WO | WO-2005/070959 | A2 | 8/2005 |
| WO | WO-2005/079419 | A2 | 9/2005 |
| WO | WO-2005/112991 | A2 | 12/2005 |
| WO | WO-2006/069262 | A2 | 6/2006 |
| WO | WO-2006/084319 | A1 | 8/2006 |
| WO | WO-2006/091591 | A1 | 8/2006 |
| WO | WO-2007/059931 | A1 | 5/2007 |
| WO | WO-2007/103322 | A2 | 9/2007 |
| WO | WO-2008/085549 | A2 | 7/2008 |
| WO | WO-2009/046498 | A1 | 4/2009 |
| WO | WO-2009/137103 | A2 | 11/2009 |
| WO | WO-2009/155332 | A1 | 12/2009 |
| WO | WO-2010/028246 | A2 | 3/2010 |
| WO | WO-2010/093436 | A2 | 8/2010 |
| WO | WO-2010/111485 | A1 | 9/2010 |
| WO | WO-2010/115229 | A1 | 10/2010 |
| WO | WO-2010/115230 | A1 | 10/2010 |
| WO | WO-2010/128303 | A1 | 11/2010 |
| WO | WO-2011/080259 | A1 | 7/2011 |
| WO | 2011/119759 | A1 | 9/2011 |
| WO | WO-2012/037612 | A1 | 3/2012 |
| WO | WO-2013/049941 | A1 | 4/2013 |
| WO | WO-2014/207708 | A2 | 12/2014 |
| WO | WO-2016/037240 | A1 | 3/2016 |
| WO | WO-2016/044839 | A2 | 3/2016 |
| WO | WO-2017/019896 | A1 | 2/2017 |
| WO | WO-2017/145097 | A2 | 8/2017 |
| WO | 2017/157964 | A1 | 9/2017 |
| WO | 2018/176099 | A1 | 10/2018 |
| WO | WO-2018/197582 | A1 | 11/2018 |
| WO | 2019/043604 | A1 | 3/2019 |
| WO | WO-2019/119067 | A1 | 6/2019 |
| WO | WO-2019/119069 | A1 | 6/2019 |
| WO | 2020/257870 | A1 | 12/2020 |
| WO | 2021/042171 | A1 | 3/2021 |

OTHER PUBLICATIONS

U.S. Appl. No. 16/495,829, filed Sep. 20, 2019, 2020-0147028, Published.

U.S. Appl. No. 16/768,278, filed May 29, 2020, 2021-0177795, Published.

U.S. Appl. No. 16/768,341, filed May 29, 2020, 2021-0230217, Published.

U.S. Appl. No. 18/112,091, filed Feb. 21, 2023, 2023-0226004, Allowed.

U.S. Appl. No. 17/926,886, filed Nov. 21, 2022, 2023-0226004, Published.

U.S. Appl. No. 13/825,679, filed May 15, 2013, U.S. Pat. No. 9,676,819, Issued.

U.S. Appl. No. 15/596,427, filed May 16, 2017, U.S. Pat. No. 10,406,100, Issued.

U.S. Appl. No. 16/522,779, filed Jul. 26, 2019, U.S. Pat. No. 11,351,114, Issued.

Agnihotri et al., Structure-activity relationships in toll-like receptor 2-agonists leading to simplified monoacyl lipopeptides. J Med Chem. Dec. 8, 2011;54(23):8148-60.

Akazawa, Development of a Functionally Designed Artificial Adjuvant. Research Report of the Uehara Memorial Foundation 23. 12 pages, (2009).

Alexopoulou et al., Recognition of double-stranded RNA and activation of NF-kappaB by Toll-like receptor 3. Nature. Oct. 18, 2001;413(6857):732-8.

Alphs et al., Protection against heterologous human papillomavirus challenge by a synthetic lipopeptide vaccine containing a broadly cross-neutralizing epitope of L2. Proc Natl Acad Sci U S A. Apr. 15, 2008;105(15):5850-5.

Amigorena, Fc gamma receptors and cross-presentation in dendritic cells. J Exp Med. Jan. 7, 2002;195(1):F1-3.

Andra et al., Enhancement of endotoxin neutralization by coupling of a C12-alkyl chain to a lactoferricin-derived peptide. Biochem J. Jan. 1, 2005;385(Pt 1):135-43.

Archer et al., MyD88-dependent responses involving toll-like receptor 2 are important for protection and clearance of Legionella pneumophila in a mouse model of Legionnaires' disease. Infect Immun. Jun. 2006;74(6):3325-33.

Asea et al., Novel signal transduction pathway utilized by extracellular HSP70: role of toll-like receptor (TLR) 2 and TLR4. J Biol Chem. Apr. 26, 2002;277(17):15028-34.

Azuma et al., The peptide sequence of diacyl lipopeptides determines dendritic cell TLR2-mediated NK activation. PLoS One. Sep. 2, 2010;5(9):e12550, 12 pages.

Bartlett et al., Upper Airway TLR2 Immune Modulators Prime Broad Respiratory Immunity Against Rhinovirus and Influenza Infection and Inhibit Subsequent Lung Inflammation. American Journal of Respiratory and Critical Care Medicine. 2018;197:Abstract A7803, 3 pages.

Basto et al., Targeting TLR2 for vaccine development. J Immunol Res. 2014;2014:619410, 22 pages.

Batzloff et al., Intranasal vaccination with a lipopeptide containing a conformationally constrained conserved minimal peptide, a universal T cell epitope, and a self-adjuvanting lipid protects mice from group A *Streptococcus* challenge and reduces throat colonization. J Infect Dis. Aug. 1, 2006;194(3):325-30.

(56) References Cited

OTHER PUBLICATIONS

Baz et al., Branched and linear lipopeptide vaccines have different effects on primary CD4+ and CD8+ T-cell activation but induce similar tumor-protective memory CD8+ T-cell responses. Vaccine. May 19, 2008;26(21):2570-9.
Beaumont et al., Design of ester prodrugs to enhance oral absorption of poorly permeable compounds: challenges to the discovery scientist. Curr Drug Metab. Dec. 2003;4(6):461-85.
Belz et al., A previously unrecognized H-2D(b)-restricted peptide prominent in the primary influenza A virus-specific CD8(+) T-cell response is much less apparent following secondary challenge. J Virol. Apr. 2000;74(8):3486-93.
Bodmer et al., Enhanced recognition of a modified peptide antigen by cytotoxic T cells specific for influenza nucleoprotein. Cell. Jan. 29, 1988;52(2):253-8.
Bogoch et al., Diagnosis of influenza from lower respiratory tract sampling after negative upper respiratory tract sampling. Virulence. Jan. 1, 2013;4(1):82-4.
Boiardi et al., Reducing transmission of SARS-CoV-2 with intranasal prophylaxis. EBioMedicine. Jan. 2021;63:103170, 2 pages.
Brown et al., Immune recognition. A new receptor for beta-glucans. Nature. Sep. 6, 2001;413(6851):36-7.
Bulut et al., Chlamydial heat shock protein 60 activates macrophages and endothelial cells through Toll-like receptor 4 and MD2 in a MyD88-dependent pathway. J Immunol. Feb. 1, 2002;168(3):1435-40.
Buwitt-Beckmann et al., TLR1- and TLR6-independent recognition of bacterial lipopeptides. J Biol Chem. Apr. 7, 2006;281(14):9049-57.
Buwitt-Beckmann et al., Toll-like receptor 6-independent signaling by diacylated lipopeptides. Eur J Immunol. Jan. 2005;35(1):282-9.
Chaturvedi et al., A review on mucoadhesive polymer used in nasal drug delivery system. J Adv Pharm Technol Res. Oct. 2011;2(4):215-22.
Cheng et al., Characterization of nasal spray pumps and deposition pattern in a replica of the human nasal airway. J Aerosol Med. 2001 Summer;14(2):267-80.
Chow et al., Toll-like receptor-4 mediates lipopolysaccharide-induced signal transduction. J Biol Chem. Apr. 16, 1999;274(16):10689-92.
Chua et al., A Self-adjuvanting Lipopeptide Vaccine for Immunotherapy of Hepatitis C Virus Infection Activates Dendritic Cells and Induces Antigen-Specific T Cell Responses. J Hepat. 2008;48:S236-S237, Abstract 635.
Chua et al., Comparison of lipopeptide-based immunocontraceptive vaccines containing different lipid groups. Vaccine. Jan. 2, 2007;25(1):92-101.
Chua et al., Dendritic cell acquisition of epitope cargo mediated by simple cationic peptide structures. Peptides. Jun. 2008;29(6):881-90.
Chua et al., Enhancing immunogenicity of HCV DNA vaccines by targeted delivery to dendritic cells. Journal of Hepatology. 2008;48:S236, Abstract 634.
Chua et al., Soluble proteins induce strong CD8+ T cell and antibody responses through electrostatic association with simple cationic or anionic lipopeptides that target TLR2. J Immunol. Aug. 15, 2011;187(4):1692-701.
Chua et al., The use of a TLR2 agonist-based adjuvant for enhancing effector and memory CD8 T-cell responses. Immunol Cell Biol. Apr. 2014;92(4):377-83.
Cleret et al., Lung dendritic cells rapidly mediate anthrax spore entry through the pulmonary route. J Immunol. Jun. 15, 2007;178(12):7994-8001.
Cluff et al., Synthetic toll-like receptor 4 agonists stimulate innate resistance to infectious challenge. Infect Immun. May 2005;73(5):3044-52.
Contoli et al., Viral infections in exacerbations of asthma and chronic obstructive pulmonary disease. Minerva Med. Dec. 2009;100(6):467-78.
Deliyannis et al., Intranasal lipopeptide primes lung-resident memory CD8+ T cells for long-term pulmonary protection against influenza. Eur J Immunol. Mar. 2006;36(3):770-8.
Dikopoulos et al., Novel peptide-based vaccines efficiently prime murine “help”-independent CD8+ T cell responses in the liver. Hepatology. Aug. 2004;40(2):300-9.
Djupesland, Nasal drug delivery devices: characteristics and performance in a clinical perspective-a review. Drug Deliv Transl Res. Feb. 2013;3(1):42-62.
Duggan et al., Broad Resistance Against Pneumonia Induced By Synergistic TLR2/6 And TLR9 Stimulation. American Journal of Respiratory and Critical Care Medicine. 2010;181:Abstract A1799, 3 pages.
Duggan et al., Synergistic interactions of TLR2/6 and TLR9 induce a high level of resistance to lung infection in mice. J Immunol. May 15, 2011;186(10):5916-26.
Engering et al., The mannose receptor functions as a high capacity and broad specificity antigen receptor in human dendritic cells. Eur J Immunol. Sep. 1997;27(9):2417-25.
Ernest et al., The Toll-Like Receptor 2 agonist PEG-Pam2Cys as an immunochemoprophylactic and immunochemotherapeutic against the liver and transmission stages of malaria parasites. Int J Parasitol Drugs Drug Resist. Dec. 2018;8(3):451-458.
Ettmayer et al., Lessons learned from marketed and investigational prodrugs. J Med Chem. May 6, 2004;47(10):2393-404.
Farley et al., Lipopolysaccharide structure determines ionic and hydrophobic binding of a cationic antimicrobial neutrophil granule protein. Infect Immun. Jun. 1988;56(6):1589-92.
Feinberg et al., Structural basis for selective recognition of oligosaccharides by DC-SIGN and DC-SIGNR. Science. Dec. 7, 2001;294(5549):2163-6.
Feng et al., A toll-like receptor agonist mimicking microbial signal to generate tumor-suppressive macrophages. Nat Commun. May 22, 2019;10(1):2272, 14 pages.
Firat et al., H-2 class I knockout, HLA-A2.1-transgenic mice: a versatile animal model for preclinical evaluation of antitumor immunotherapeutic strategies. Eur J Immunol. Oct. 1999;29(10):3112-21.
Frison et al., Oligolysine-based oligosaccharide clusters: selective recognition and endocytosis by the mannose receptor and dendritic cell-specific intercellular adhesion molecule 3 (ICAM-3)-grabbing nonintegrin. J Biol Chem. Jun. 27, 2003;278(26):23922-9.
Fujimoto et al., Virus clearance through apoptosis-dependent phagocytosis of influenza A virus-infected cells by macrophages. J Virol. Apr. 2000;74(7):3399-403.
Fuse et al., Role of Toll-like receptor 2 in recognition of Legionella pneumophila in a murine pneumonia model. J Med Microbiol. Mar. 2007;56(Pt 3):305-312.
Futaki et al., Arginine-rich peptides. An abundant source of membrane-permeable peptides having potential as carriers for intracellular protein delivery. J Biol Chem. Feb. 23, 2001;276(8):5836-40.
Gariepy et al., Vectorial delivery of macromolecules into cells using peptide-based vehicles. Trends Biotechnol. Jan. 2001;19(1):21-8.
Ghielmetti et al., Synthetic bacterial lipopeptide analogs facilitate naive CD4+ T cell differentiation and enhance antigen-specific HLA-II-restricted responses. Eur J Immunol. Aug. 2005;35(8):2434-42.
Gianfrani et al., Human memory CTL response specific for influenza A virus is broad and multispecific. Hum Immunol. May 2000;61(5):438-52.
Gonzalez-Juarrero et al., Dynamics of macrophage cell populations during murine pulmonary tuberculosis. J Immunol. Sep. 15, 2003;171(6):3128-35.
Gotch et al., Cytotoxic T lymphocytes recognize a fragment of influenza virus matrix protein in association with HLA-A2. Nature. Apr. 30-May 6, 1987;326(6116):881-2.
Gratton et al., Cell-permeable peptides improve cellular uptake and therapeutic gene delivery of replication-deficient viruses in cells and in vivo. Nat Med. Mar. 2003;9(3):357-62.
Gros et al., A non-covalent peptide-based strategy for protein and peptide nucleic acid transduction. Biochim Biophys Acta. Mar. 2006;1758(3):384-93.

(56) References Cited

OTHER PUBLICATIONS

Guo et al., The Novel Toll-Like Receptor 2 Agonist SUP3 Enhances Antigen Presentation and T Cell Activation by Dendritic Cells. Front Immunol. Feb. 21, 2017;8:158, 15 pages.
Han et al., Targeted prodrug design to optimize drug delivery. AAPS PharmSci. 2000;2(1):E6, 11 pages.
Hayashi et al., The innate immune response to bacterial flagellin is mediated by Toll-like receptor 5. Nature. Apr. 26, 2001;410(6832):1099-103.
Heil et al., Species-specific recognition of single-stranded RNA via toll-like receptor 7 and 8. Science. Mar. 5, 2004;303(5663):1526-9.
Hemmi et al., A Toll-like receptor recognizes bacterial DNA. Nature. Dec. 7, 2000;408(6813):740-5.
Hemmi et al., Small anti-viral compounds activate immune cells via the TLR7 MyD88-dependent signaling pathway. Nat Immunol. Feb. 2002;3(2):196-200.
Heuking et al., Stimulation of human macrophages (THP-1) using Toll-like receptor-2 (TLR-2) agonist decorated nanocarriers. J Drug Target. Sep. 2009;17(8):662-70.
Hoffmann et al., Induction of tumor cytotoxicity in murine bone marrow-derived macrophages by two synthetic lipopeptide analogues. Biol Chem Hoppe Seyler. Jun. 1989;370(6):575-82.
Huynh et al., Novel toll-like receptor 2 ligands for targeted pancreatic cancer imaging and immunotherapy. J Med Chem. Nov. 26, 2012;55(22):9751-62.
Ismaili et al., Monophosphoryl lipid A activates both human dendritic cells and T cells. J Immunol. Jan. 15, 2002;168(2):926-32.
Iwabuchi et al., Effects of intranasal administration of Bifidobacterium longum BB536 on mucosal immune system in respiratory tract and influenza virus infection in mice. Milk Science. 2009;58(3):129-133.
Jackson et al., A totally synthetic vaccine of generic structure that targets Toll-like receptor 2 on dendritic cells and promotes antibody or cytotoxic T cell responses. Proc Natl Acad Sci U S A. Oct. 26, 2004;101(43):15440-5.
Jaiswal et al., Innate Immune Response Modulation and Resistance to SARS-CoV-2 infection: A Prospective Comparative Cohort Study in High Risk Healthcare Workers. medRxiv. Retrieved online at: https://www.medrxiv.org/content/10.1101/2020.10.20.20214965v1. Oct. 21, 2020, 6 pages.
Jameson et al., Human CD8+ and CD4+ T lymphocyte memory to influenza A viruses of swine and avian species. J Immunol. Jun. 15, 1999;162(12):7578-83.
Kang et al., Recognition of lipopeptide patterns by Toll-like receptor 2-Toll-like receptor 6 heterodimer. Immunity. Dec. 18, 2009;31(6):873-84.
Kawamura et al., Probing the impact of valency on the routing of arginine-rich peptides into eukaryotic cells. Biochemistry. Jan. 31, 2006;45(4):1116-27.
Kery et al., Ligand recognition by purified human mannose receptor. Arch Biochem Biophys. Oct. 1992;298(1):49-55.
Khong et al., Adjuvants for peptide-based cancer vaccines. J Immunother Cancer. Sep. 20, 2016;4:56, 11 pages.
Kutzler et al., Developing DNA vaccines that call to dendritic cells. J Clin Invest. Nov. 2004;114(9):1241-4.
Landsman et al., Lung macrophages serve as obligatory intermediate between blood monocytes and alveolar macrophages. J Immunol. Sep. 15, 2007;179(6):3488-94.
Lau et al., Lipid-containing mimetics of natural triggers of innate immunity as CTL-inducing influenza vaccines. Int Immunol. Dec. 2006;18(12):1801-13.
Li et al., Relationship of Toll like receptor-2 and some virus infectious diseases. Chemistry of Life. 2009;4:568-571.
Licalsi et al., Dry powder inhalation as a potential delivery method for vaccines. Vaccine. Mar. 26, 1999;17(13-14):1796-803.
Lu et al., Synthesis and Evaluation of Novel TLR2 Agonists as Potential Adjuvants for Cancer Vaccines. J Med Chem. Mar. 12, 2020;63(5):2282-2291.
Martinez et al., Direct TLR2 signaling is critical for NK cell activation and function in response to vaccinia viral infection. PLoS Pathog. Mar. 12, 2010;6(3):e1000811, 13 pages.
Medical Dictionary, admixture. retrieved online at: https://medical-dictionary.thefreedictionary.com/admixture. 1 page, (2012).
Meng et al., Cellular recognition of tri-/di-palmitoylated peptides is independent from a domain encompassing the N-terminal seven leucine-rich repeat (LRR)/LRR-like motifs of TLR2. J Biol Chem. Oct. 10, 2003;278(41):39822-9.
Metzger et al., Synthesis of novel immunologically active tripalmitoyl-S-glycerylcysteinyl lipopeptides as useful intermediates for immunogen preparations. Int J Pept Protein Res. Jan. 1991;37(1):46-57.
Morr et al., Differential recognition of structural details of bacterial lipopeptides by toll-like receptors. Eur J Immunol. Dec. 2002;32(12):3337-47.
Muhlradt et al., Isolation, structure elucidation, and synthesis of a macrophage stimulatory lipopeptide from Mycoplasma fermentans acting at picomolar concentration. J Exp Med. Jun. 2, 1997;185(11):1951-8.
Muhlradt et al., Structure and specific activity of macrophage-stimulating lipopeptides from Mycoplasma hyorhinis. Infect Immun. Oct. 1998;66(10):4804-10.
Muller, Prodrug approaches for enhancing the bioavailability of drugs with low solubility. Chem Biodivers. Nov. 2009;6(11):2071-83.
Okusawa et al., Relationship between structures and biological activities of mycoplasmal diacylated lipopeptides and their recognition by toll-like receptors 2 and 6. Infect Immun. Mar. 2004;72(3):1657-65.
Olive et al., A lipid core peptide construct containing a conserved region determinant of the group A streptococcal M protein elicits heterologous opsonic antibodies. Infect Immun. May 2002;70(5):2734-8.
Olive et al., Enhanced protection against *Streptococcus pyogenes* infection by intranasal vaccination with a dual antigen component M protein/Sfbl lipid core peptide vaccine formulation. Vaccine. Feb. 26, 2007;25(10):1789-97.
Ozinsky et al., The repertoire for pattern recognition of pathogens by the innate immune system is defined by cooperation between toll-like receptors. Proc Natl Acad Sci U S A. Dec. 5, 2000;97(25):13766-71.
Palma et al., The toll-like receptor 2/6 ligand MALP-2 reduces the viability of *Mycobacterium tuberculosis* in murine macrophages. Open Microbiol J. Apr. 3, 2009;3:47-52.
Pascolo et al., HLA-A2.1-restricted education and cytolytic activity of CD8(+) T lymphocytes from beta2 microglobulin (beta2m) HLA-A2.1 monochain transgenic H-2Db beta2m double knockout mice. J Exp Med. Jun. 16, 1997;185(12):2043-51.
Pina et al., Shiga toxin B-subunit sequential binding to its natural receptor in lipid membranes. Biochim Biophys Acta. Mar. 2007;1768(3):628-36.
Poltorak et al., Defective LPS signaling in C3H/HeJ and C57BL/10ScCr mice: mutations in Tlr4 gene. Science. Dec. 11, 1998;282(5396):2085-8.
Proud et al., Prophylactic intranasal administration of a TLR2/6 agonist reduces upper respiratory tract viral shedding in a SARS-CoV-2 challenge ferret model. EBioMedicine. Jan. 2021;63:103153, 9 pages.
Raffai et al., Binding of an antibody mimetic of the human low density lipoprotein receptor to apolipoprotein E is governed through electrostatic forces. Studies using site-directed mutagenesis and molecular modeling. J Biol Chem. Mar. 10, 2000;275(10):7109-16.
Raffai et al., Molecular characterization of two monoclonal antibodies specific for the LDL receptor-binding site of human apolipoprotein E. J Lipid Res. Sep. 1995;36(9):1905-18.
Rathananand et al., Preparation of mucoadhesive microspheres for nasal delivery by spray drying. Indian J Pharm Sci. 2007;69(5):651-657.
Reppe et al., Immunostimulation with macrophage-activating lipopeptide-2 increased survival in murine pneumonia. Am J Respir Cell Mol Biol. Apr. 2009;40(4):474-81.

(56) References Cited

OTHER PUBLICATIONS

Richard et al., TLR2 signaling decreases transmission of *Streptococcus pneumoniae* by limiting bacterial shedding in an infant mouse Influenza A co-infection model. PLoS Pathog. 2014;10(8):e1004339, 9 pages.
Riedl et al., Complexes of DNA vaccines with cationic, antigenic peptides are potent, polyvalent CD8(+) T-cell-stimulating immunogens. Methods Mol Med. 2006;127:159-69.
Riedl et al., Peptides containing antigenic and cationic domains have enhanced, multivalent immunogenicity when bound to DNA vaccines. J Mol Med (Berl). Feb. 2004;82(2):144-52.
Rose et al., FSL-1, a bacterial-derived toll-like receptor 2/6 agonist, enhances resistance to experimental HSV-2 infection. Virol J. Nov. 10, 2009;6:195, 11 pages.
Rothbard et al., A sequence pattern common to T cell epitopes. EMBO J. Jan. 1988;7(1):93-100.
Sasidharan Nair et al., Immune checkpoint inhibitors in cancer therapy: a focus on T-regulatory cells. Immunol Cell Biol. Jan. 2018;96(1):21-33.
Schirmbeck et al., Antigenic epitopes fused to cationic peptide bound to oligonucleotides facilitate Toll-like receptor 9-dependent, but CD4+ T cell help-independent, priming of CD8+ T cells. J Immunol. Nov. 15, 2003;171(10):5198-207.
Schwandner et al., Peptidoglycan- and lipoteichoic acid-induced cell activation is mediated by toll-like receptor 2. J Biol Chem. Jun. 18, 1999;274(25):17406-9.
Seifert et al., Activation of superoxide formation and lysozyme release in human neutrophils by the synthetic lipopeptide Pam3Cys-Ser-(Lys)4. Involvement of guanine-nucleotide-binding proteins and synergism with chemotactic peptides. Biochem J. May 1, 1990;267(3):795-802.
Sharma et al., Effect of TLR agonist on infections bronchitis virus replication and cytokine expression in embryonated chicken eggs. Mol Immunol. Apr. 2020;120:52-60.
Sherman et al., Extracellular processing of peptide antigens that bind class I major histocompatibility molecules. J Exp Med. May 1, 1992;175(5):1221-6.
Shiratsuchi et al., Elimination of influenza virus-infected cells by phagocytosis. Yakugaku Zasshi. Dec. 2006;126(12):1245-51.
Singh et al., Recent trends in targeted anticancer prodrug and conjugate design. Curr Med Chem. 2008;15(18):1802-26.
Stambach et al., Characterization of carbohydrate recognition by langerin, a C-type lectin of Langerhans cells. Glycobiology. May 2003;13(5):401-10.
Takeuchi et al., Cutting edge: preferentially the R-stereoisomer of the mycoplasmal lipopeptide macrophage-activating lipopeptide-2 activates immune cells through a toll-like receptor 2- and MyD88-dependent signaling pathway. J Immunol. Jan. 15, 2000;164(2):554-7.
Takeuchi et al., Cutting edge: role of Toll-like receptor 1 in mediating immune response to microbial lipoproteins. J Immunol. Jul. 1, 2002;169(1):10-4.
Tan et al., Intranasal administration of the TLR2 agonist Pam2Cys provides rapid protection against influenza in mice. Mol Pharm. 2012;9(9):2710-2718.
Tannock et al., Relative immunogenicity of the cold-adapted influenza virus A/Ann Arbor/6/60 (A/AA/6/60-ca), recombinants of A/AA/6/60-ca, and parental strains with similar surface antigens. Infect Immun. Feb. 1984;43(2):457-62.
Tansey et al., Synthesis and characterization of branched poly(L-glutamic acid) as a biodegradable drug carrier. J Control Release. Jan. 8, 2004;94(1):39-51.
Testa, Prodrug research: futile or fertile? Biochem Pharmacol. Dec. 2004.
Tighe et al., Conjugation of protein to immunostimulatory DNA results in a rapid, long-lasting and potent induction of cell-mediated and humoral immunity. Eur J Immunol. Jul. 2000;30(7):1939-47.
Voss et al., The activity of lipopeptide TLR2 agonists critically depends on the presence of solubilizers. Eur J Immunol. Dec. 2007;37(12):3489-98.
Wali et al., Immune Modulation to Improve Survival of Viral Pneumonia in Mice. Am J Respir Cell Mol Biol. Dec. 2020;63(6):758-766.
Wallace et al., The cytotoxic T-cell response to herpes simplex virus type 1 infection of C57BL/6 mice is almost entirely directed against a single immunodominant determinant. J Virol. Sep. 1999;73(9):7619-26.
Wang et al., Adjuvant effect of the novel TLR1/TLR2 agonist Diprovocim synergizes with anti-PD-L1 to eliminate melanoma in mice. Proc Natl Acad Sci U S A. Sep. 11, 2018;115(37):E8698-E8706.
Wikipedia, TLR-2. Retrieved online at: https://en.wikipedia.org/wiki/TLR2. 14 pages, (2021).
You et al., Induced Resistance to Influenza A Infection By Cooperative TLR2/6 and TLR9 Activation. American Journal of Respiratory and Critical Care Medicine. 2010;181:Abstract A2629, 3 pages.
Zeng et al., Characterisation of the antibody response to a totally synthetic immunocontraceptive peptide vaccine based on LHRH. Vaccine. Aug. 15, 2005;23(35):4427-35.
Zeng et al., Highly immunogenic and totally synthetic lipopeptides as self-adjuvanting immunocontraceptive vaccines. J Immunol. Nov. 1, 2002;169(9):4905-12.
Zeng et al., Synthesis of a new template with a built-in adjuvant and its use in constructing peptide vaccine candidates through polyoxime chemistry. J Pept Sci. Jan.-Feb. 1996;2(1):66-72.
Zeng et al., Totally synthetic lipid-containing polyoxime peptide constructs are potent immunogens. Vaccine. Jan. 6, 2000;18(11-12):1031-9.
International Search Report and Written Opinion for Application No. PCT/AU2018/050295, dated May 23, 2018, 10 pages.
International Search Report and Written Opinion for Application No. PCT/AU2018/051397, dated Feb. 28, 2019, 16 pages.
International Search Report and Written Opinion for Application No. PCT/AU2018/051401, dated Feb. 12, 2019, 13 pages.
International Search Report and Written Opinion for Application No. PCT/AU2020/050660, dated Sep. 3, 2020, 10 pages.
International Search Report and Written Opinion for Application No. PCT/AU2021/050506, dated Jul. 13, 2021, 14 pages.
Sekiya, T. et al. "PEGylation of a TLR2-agonist-based vaccine delivery system improves antigen trafficking and the magnitude of ensuing antibody and CD8+T cell responses." Biomaterials 137: 61-72 (2017).
American Cancer Society, Acute Lymphocytic Leukemia (ALL) Causes, Risk Factors, and Prevention. cancer.org. 13 pages, Aug. 13, 2025.
American Cancer Society, Can Acute Lymphocytic Leukemia Be Prevented? 1 page, (2018).
Blackadar, Historical review of the causes of cancer. World J Clin Oncol. Feb. 10, 2016;7(1):54-86.
Cui et al., Origin and evolution of pathogenic coronaviruses. Nat Rev Microbiol. Mar. 2019;17(3):181-192.
Deliyannis et al., TLR2-mediated activation of innate responses in the upper airways confers antiviral protection of the lungs. JCI Insight. Mar. 8, 2021;6(5):e140267, 17 pages.
Hassanpour et al., Review of cancer from perspective of molecular. Journal of Cancer Research and Practice. 2017;4:127-129.
Huang et al., The role of toll-like receptors (TLRs) in pan-cancer. Ann Med. Dec. 2022;54(1):1918-1937.
Lu, TLR Agonists for Cancer Immunotherapy: Tipping the Balance between the Immune Stimulatory and Inhibitory Effects. Front Immunol. Mar. 3, 2014;5:83, 4 pages.
Nair et al., Natural Killer T Cells in Cancer Immunotherapy. Front Immunol. Sep. 22, 2017;8:1178, 18 pages.
Pahlavanneshan et al., Toll-Like Receptor-Based Strategies for Cancer Immunotherapy. J Immunol Res. May 22, 2021;2021:9912188, 14 pages.
Rolfo et al., Applications and clinical trial landscape using Toll-like receptor agonists to reduce the toll of cancer. NPJ Precis Oncol. Mar. 8, 2023;7(1):26, 11 pages.
Tang et al., The hallmarks of COVID-19 disease. PLoS Pathog. May 22, 2020;16(5):e1008536, 24 pages.

(56) References Cited

OTHER PUBLICATIONS

Yu et al., Tumor-immune profiling of murine syngeneic tumor models as a framework to guide mechanistic studies and predict therapy response in distinct tumor microenvironments. PLoS One. Nov. 2, 2018;13(11):e0206223. 27 pages.
Zhong et al., Comparison of the molecular and cellular phenotypes of common mouse syngeneic models with human tumors. BMC Genomics. Jan. 2, 2020;21(1):2, 17 pages.

* cited by examiner

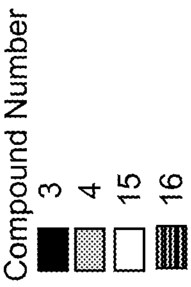
Figure 1
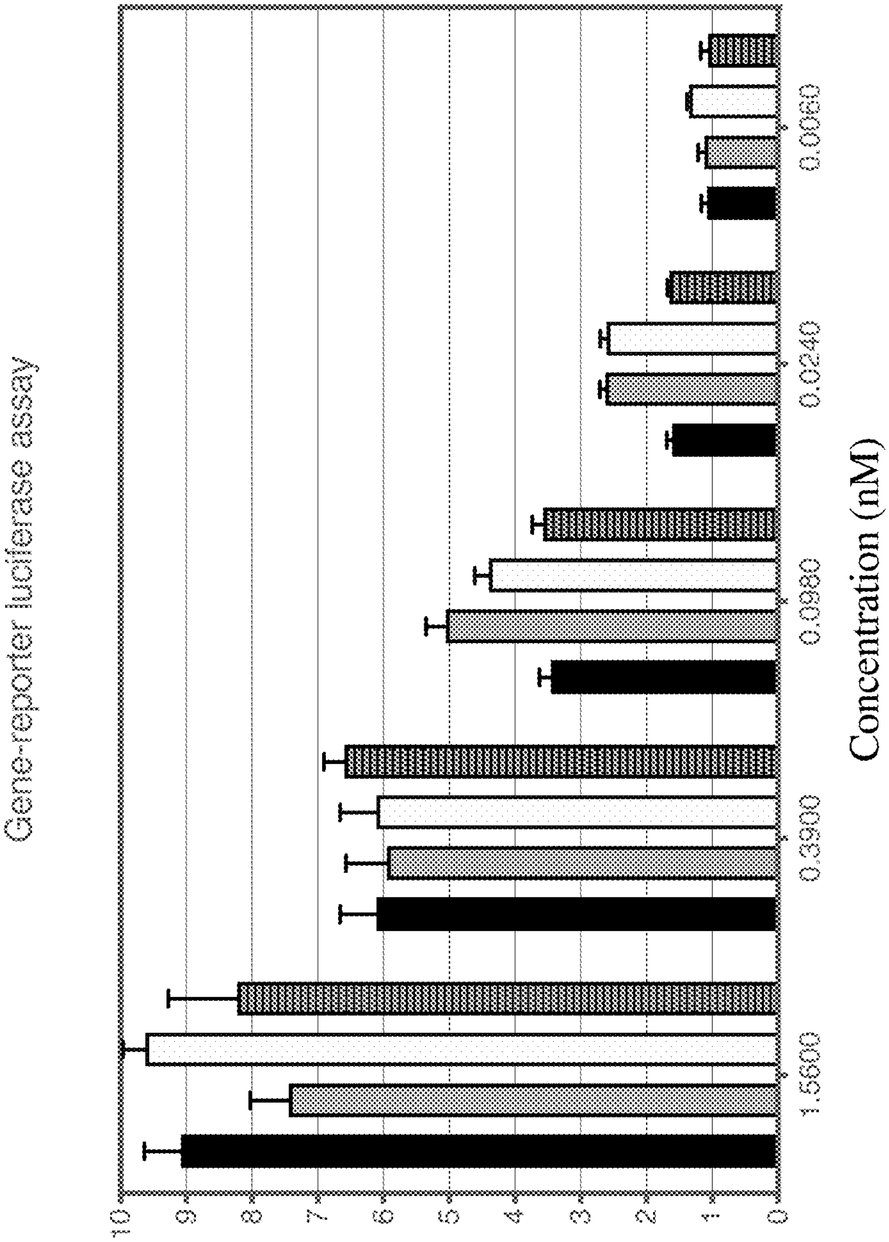

MOLECULES

This application is a 35 U.S.C. § 371 national stage filing of International Application No. PCT/AU2020/050660, filed on Jun. 26, 2020, which claims priority to Australian provisional patent application no. 2019902231, filed on Jun. 26, 2019 and Australian provisional patent application no. 2019904862, filed on Dec. 20, 2019, the entire contents of each of which are hereby incorporated by reference.

FIELD OF THE INVENTION

The present invention relates to compounds and their compositions, and the use of such compounds and compositions in the prevention and/or treatment of respiratory infections, or respiratory diseases or conditions associated with viral or bacterial infections.

BACKGROUND OF THE INVENTION

Respiratory infections are among the most common causes of human disease worldwide and are commonly caused by viruses. According to the World Health Organisation (WHO), worldwide, seasonal epidemics of influenza alone are estimated to result in about 3 to 5 million cases of severe illness, and about 250,000 to 500,000 deaths per year.

Although vaccines are available for some seasonal strains, for example influenza, these have not always been shown to be adequate due to several factors, such as infection between the lag phase between inoculation and the formation of antibodies and immune cells being formed. Seasonal vaccinations often also need modification, including re-formulation and administration, and may also not provide protection for the full length of time desired. For other occurrences of influenza, such as unexpected panademic outbreaks, a vaccine is not always known, developed or available.

Viral respiratory infections can also worsen the severity of diseases of the respiratory conditions leading to exacerbations (attacks). Exacerbations can occur for conditions such as asthma and chronic obstructive pulmonary disease (COPD). Asthma and COPD exacerbations are the most clinically and economically important forms of the diseases.

The vast majority of exacerbations, particularly in asthma, continue to occur despite use of the best available current therapies. When exacerbations do occur, treatment options are limited and have developed little in recent years. Treatment involves increasing doses of inhaled bronchodilators and systemic or oral corticosteroids—which are the same drugs that failed to prevent the exacerbation occurring in the first place.

There is a need, therefore, for new or improved compounds and methods for the treatment and/or prevention for respiratory infections, or respiratory conditions associated with viral or bacterial infections.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides Toll-Like Receptor 2 protein (TLR2) agonist compounds and their compositions. TLR2 agonists have previously been identified to show potential in treating respiratory diseases and conditions associated with infectious agents such as viruses and bacteria. Advantageously, the compounds and compositions of the present application may show activity and have use in therapeutic areas such as treating and/or preventing respiratory diseases or conditions associated with viral or bacterial infections. In addition, the compounds and compositions of the present application may demonstrate increased stability which may translate to longer clearance rates following administration. Compounds of the invention demonstrate improved solution stability compared to other related compounds.

In one aspect, the present invention provides a compound comprising the structure:

A-Y—B wherein A comprises or consists of:

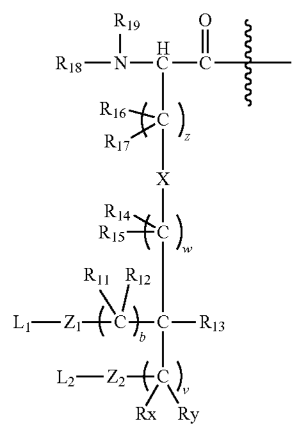

wherein b and w are each independently an integer from 0 to 7 and v is an integer from 0 to 5, such as from 2 to 5, provided that:

the sum of b, v, and w is at least 3; and the sum of b and w is from 0 to 7;

z is 1 or 2;

X is selected from —S—, —S(═O)— and —S(═O)$_2$—;

$Z_1$ and $Z_2$ are each independently selected from the group consisting of —O—, —NR—, —S—, S(═O), —S(═O)$_2$—, —C(═O)O—, —OC(═O)—, —C(═O)NR—, —NRC(═O)—, —C(═O)S—, —SC(═O)—, —OC(═O)O—, —NRC(═O)O—, —OC(═O)NR—, and —NRC(═O)NR—;

$R_{11}$, $R_{12}$, $R_x$, $R_y$, $R_{14}$, $R_{15}$, $R_{16}$, and $R_{17}$ are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(═O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

Y is

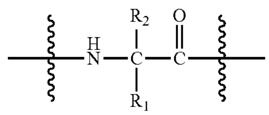

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_8$ is selected from the group consisting of H and a straight or branched $C_1$-$C_6$ alkyl;

and

B comprises or consists of Polyethylene Glycol (PEG), or a pharmaceutically acceptable salt, solvate or prodrug thereof.

The present invention also provides a compound comprising A and PEG, wherein the A and PEG are linked by a glycine, serine, homoserine, threonine, phosphoserine, asparagine or glutamine residue, or an ester of a glutamine residue, wherein A in the compound has the structure:

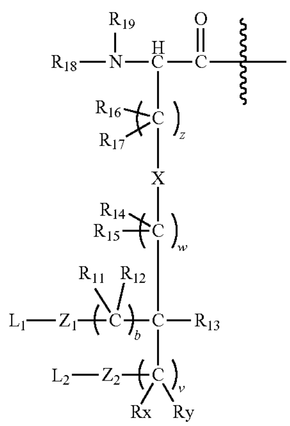

wherein b and w are each independently an integer from 0 to 7 and v is an integer from 0 to 5, such as from 2 to 5, provided that:

the sum of b, v, and w is at least 3; and the sum of b and w is from 0 to 7;

z is 1 or 2;

X is selected from —S—, —S(=O)— and —$S(=O)_2$—;

$Z_1$ and $Z_2$ are each independently selected from the group consisting of —O—, —NR—, —S—, —S(=O)—, —$S(=O)_2$—, —C(=O)O—, —OC(=O)—, —C(=O)NR—, —NRC(=O)—, —C(=O)S—, —SC(=O)—, —OC(=O)O—, —NRC(=O)O—, —OC(=O)NR—, and —NRC(=O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(=O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

or a pharmaceutically acceptable salt, solvate or prodrug thereof.

In one aspect, the present invention provides a compound comprising:

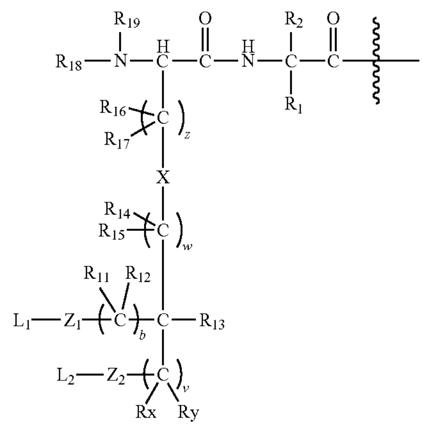

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_8$ is selected from the group consisting of H and a straight or branched $C_1$-$C_6$ alkyl;

b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(=O)— and —$S(=O)_2$—;

$Z_1$ and $Z_2$ are each independently selected from the group consisting of —O—, —NR—, —S—, —S(=O)—, —$S(=O)_2$—, —C(=O)O—, —OC(=O)—, —C(=O)NR—, —NRC(=O)—, —C(=O)S—, —SC(=O)—, —OC(=O)O—, —NRC(=O)O—, —OC(=O)NR—, and —NRC(=O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(=O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

covalently linked to polyethylene glycol (PEG), or a pharmaceutically acceptable salt, solvate or prodrug thereof.

In one aspect, the present invention provides a compound of formula (VI):

(VI)

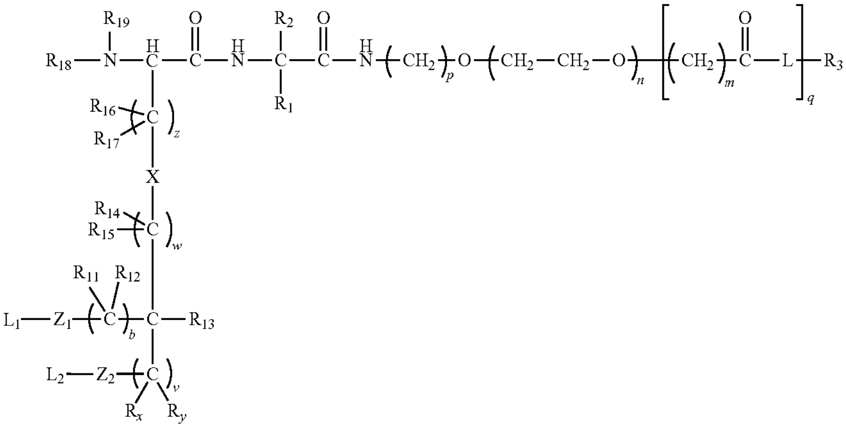

wherein n is 3 to 100;

m is 1, 2, 3 or 4;

p is 2, 3 or 4;

q is null or 1;

$R_1$ and $R_2$ are independently selected from the group consisting of H, $—CH_2OH$, $—CH_2CH_2OH$, $—CH(CH_3)OH$, $—CH_2OPO(OH)_2$, $—CH_2C(═O)NH_2$, $—CH_2CH_2C(═O)OH$ and $CH_2CH_2C(═O)OR_8$, wherein any one of the alkyl hydrogens can be replaced with a halogen;

$R_8$ is selected from the group consisting of H and a straight or branched $C_1$-$C_6$ alkyl;

wherein when q=1, $R_3$ is $—NH_2$ or —OH;

wherein when q=0, $R_3$ is H;

L is null or consists of 1 to 10 units, wherein each unit is a natural alpha amino acid or derived from a natural alpha amino acid, and has the formula:

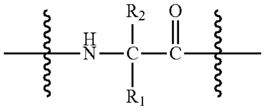

wherein $R_4$ is H; and $R_5$ is the side chain, or second hydrogen of the amino acid;

b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(═O)— and $—S(═O)_2—$;

$Z_1$ and $Z_2$ are each independently selected from the group consisting of —O—, —NR—, —S—, —S(═O)—, $—S(═O)_2—$, —C(═O)O—, —OC(═O)—, —C(═O)NR—, —NRC(═O)—, —C(═O)S—, —SC(═O)—, —OC(═O)O—, —NRC(═O)O—, —OC(═O)NR—, and —NRC(═O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(═O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

or a pharmaceutically acceptable salt, solvate or prodrug thereof.

In one embodiment, the present invention provides a compound of formula (VII):

$$A\text{-}Y—NH—(CH_2)_p—O—(CH_2—CH_2—O)_n—[(CH_2)_m—CO\text{-}L\text{-}]_qR_3 \quad (VII)$$

wherein

A has the structure:

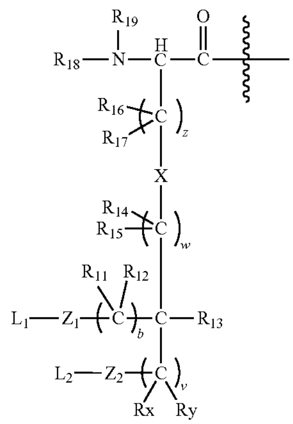

Y is

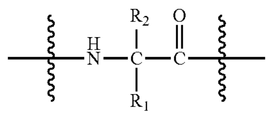

wherein $R_1$ and $R_2$ are independently selected from the group consisting of H, $—CH_2OH$, $—CH_2CH_2OH$, $—CH(CH_3)OH$, $—CH_2OPO(OH)_2$, $—CH_2C(=O)NH_2$, $—CH_2CH_2C(=O)OH$ and $—CH_2CH_2C(=O)OR_8$, wherein any one of the alkyl hydrogens can be replaced with a halogen;

$R_8$ is selected from the group consisting of H and a straight or branched $C_1$-$C_6$ alkyl;

n is 3 to 100;

m is 1, 2, 3 or 4;

p is 2, 3 or 4;

q is null or 1;

wherein when q=1, $R_3$ is $—NH_2$ or —OH;

wherein when q=0, $R_3$ is H;

L is null or consists of 1 to 10 units, wherein each unit is a natural alpha amino acid or derived from a natural alpha amino acid, and has the formula:

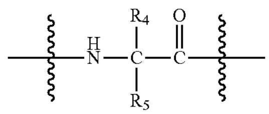

wherein $R_4$ is H; and $R_5$ is the side chain, or second hydrogen of the amino acid;

b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(=O)— and $—S(=O)_2—$;

$Z_1$ and $Z_2$ are each independently selected from the group consisting of —O—, —NR—, —S—, —S(=O)—, $—S(=O)_2—$, —C(=O)O—, —OC(=O)—, —C(=O)NR—, —NRC(=O)—, —C(=O)S—, —SC(=O)—, —OC(=O)O—, —NRC(=O)O—, —OC(=O)NR—, and —NRC(=O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

$R_{19}$ is H, $C_1$-$C_5$ aliphatic, an amino protecting group, $L_3$-C(=O)—, or A2;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

or a pharmaceutically acceptable salt, solvate or prodrug thereof.

In one embodiment, the compound has the formula (X):

formula (X)

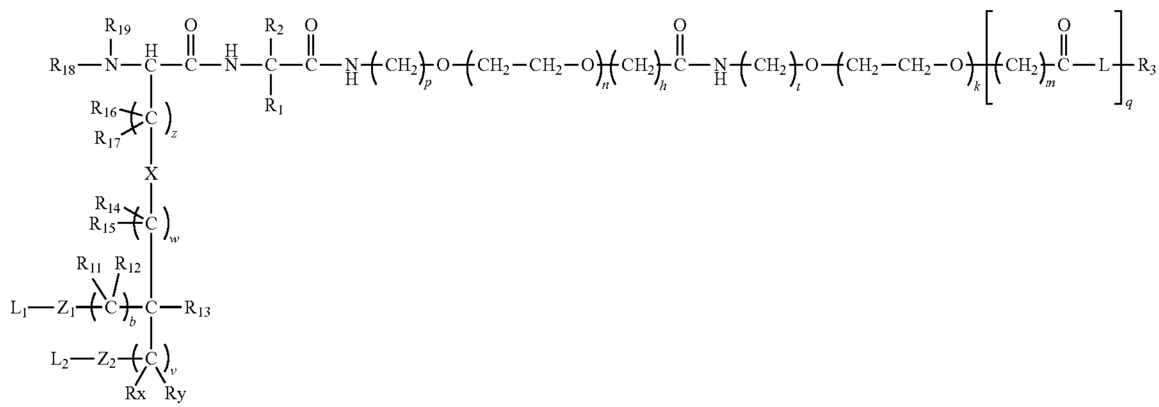

wherein n is 3 to 100;

k is 3 to 100;

m is 1, 2, 3 or 4;

p is 2, 3 or 4;

t is 2, 3 or 4;

h is 1, 2, 3 or 4;

q is null or 1;

wherein $R_1$ and $R_2$ are independently selected from the group consisting of H, $—CH_2OH$, $—CH_2CH_2OH$, $—CH(CH_3)OH$, $—CH_2OPO(OH)_2$, $—CH_2C(=O)NH_2$, $—CH_2CH_2C(=O)OH$ and $—CH_2CH_2C(=O)OR_8$, wherein any one of the alkyl hydrogens can be replaced with a halogen;

$R_8$ is selected from the group consisting of H and a straight or branched $C_1$-$C_6$ alkyl;

wherein when q=1, $R_3$ is $—NH_2$ or —OH;

wherein when q=0, $R_3$ is H;

L is null or consists of 1 to 10 units, wherein each unit is a natural alpha amino acid or derived from a natural alpha amino acid, and has the formula:

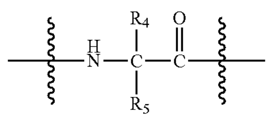

wherein $R_4$ is H; and $R_5$ is the side chain, or second hydrogen of the amino acid;

b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(═O)— and —S(═O)$_2$—;

$Z_1$ and $Z_2$ are each independently selected from the group consisting of —O—, —NR—, —S—, —S(═O)—, —S(═O)$_2$—, —C(═O)O—, —OC(═O)—, —C(═O)NR—, —NRC(═O)—, —C(═O)S—, —SC(═O)—, —OC(═O)O—, —NRC(═O)O—, —OC(═O)NR—, and —NRC(═O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(═O)—, or A2;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

or a pharmaceutically acceptable salt, solvate or prodrug thereof.

The present invention also provides for compositions comprising, consisting essentially of, or consisting of, a compound of the invention as described herein or a pharmaceutically acceptable salt, solvate or prodrug thereof, and a pharmaceutically acceptable carrier, diluent or excipient.

In one aspect, the present invention provides a method of treating and/or preventing a disease, comprising raising an innate immune response in a subject by administering an effective amount of a compound of the invention as described herein or a pharmaceutically acceptable salt, solvate or prodrug thereof to the subject in need thereof.

In another aspect, the present invention provides a method of treating and/or preventing a disease associated with, or caused by, an infectious agent, comprising administering to a subject in need thereof an effective amount of a compound of the invention as described herein or a pharmaceutically acceptable salt, solvate or prodrug thereof.

In another aspect, the present invention provides a method of treating and/or preventing a respiratory disease or condition associated with a viral or bacterial infection, comprising administering to a subject in need thereof a compound of the invention as described herein or a pharmaceutically acceptable salt, solvate or prodrug thereof.

In another aspect, the present invention provides a method of treating and/or preventing a respiratory infection, comprising administering to a subject in need thereof a compound of the invention as described herein or a pharmaceutically acceptable salt, solvate or prodrug thereof.

In another aspect, the present invention provides a method for reducing airway inflammation, comprising administering to a subject in need thereof a compound of the invention as described herein or a pharmaceutically acceptable salt, solvate or prodrug thereof.

The present invention also provides a method of improving the ability of a subject to control a respiratory disease or condition during a respiratory viral infection, the method comprising administering to a subject in need thereof a compound of the invention as described herein or a pharmaceutically acceptable salt, solvate or prodrug thereof.

The present invention also provides a method of treating and/or preventing a disease or condition associated with the TLR2 receptor, the method comprising administering to a subject in need thereof a compound of the invention as described herein or a pharmaceutically acceptable salt, solvate or prodrug thereof.

The present invention also provides a method of agonising TLR2 activity in a cell, the method comprising contacting the cell with a compound of the invention as described herein or a pharmaceutically acceptable salt, solvate or prodrug thereof.

In another aspect, the present invention provides for use of a compound of the invention as described herein or a pharmaceutically acceptable salt, solvate or prodrug thereof in the preparation of a medicament for raising an innate immune response in a subject.

In another aspect, the present invention provides for use of a compound of the invention as described herein or a pharmaceutically acceptable salt, solvate or prodrug thereof in the preparation of a medicament for treating and/or preventing a disease caused by an infectious agent.

In another aspect, the present invention further provides for use of a compound of the invention as described herein or a pharmaceutically acceptable salt, solvate or prodrug thereof in the preparation of a medicament for treating and/or preventing a respiratory disease or condition associated with a viral or bacterial infection in a subject.

In another aspect, the present invention further provides for use of a compound of the invention as described herein or a pharmaceutically acceptable salt, solvate or prodrug thereof in the preparation of a medicament for treating and/or preventing a respiratory infection in a subject.

In another aspect, the present invention further provides use of a compound of the invention as described herein or a pharmaceutically acceptable salt, solvate or prodrug thereof in the preparation of a medicament for reducing airway inflammation.

In another aspect, the present invention further provides use of a compound of the invention as described herein or a pharmaceutically acceptable salt, solvate or prodrug thereof in the preparation of a medicament for improving the ability of a subject to control a respiratory disease or condition during a respiratory viral infection.

In another aspect, the present invention further provides use of a compound of the invention as described herein or a pharmaceutically acceptable salt, solvate or prodrug thereof in the preparation of a medicament for treating and/or preventing a disease or condition associated with the TLR2 receptor.

In one aspect, the present invention provides for use of a compound of the invention as described herein or a pharmaceutically acceptable salt, solvate or prodrug thereof, for raising an innate immune response in a subject.

In another aspect, the present invention provides for use of a compound of the invention as described herein or a pharmaceutically acceptable salt, solvate or prodrug thereof, for preventing a disease caused by an infectious agent, in a subject.

In another aspect, the present invention provides for use of a compound of the invention as described herein or a pharmaceutically acceptable salt, solvate or prodrug thereof, for treating and/or preventing a respiratory disease or condition associated with a viral or bacterial infection in a subject.

In another aspect, the invention provides use of a compound of the invention as described herein or a pharmaceutically acceptable salt, solvate or prodrug thereof for reducing airway inflammation in a subject.

In another aspect, the invention provides use of a compound of the invention as described herein or a pharmaceutically acceptable salt, solvate or prodrug thereof for controlling a respiratory disease or condition during a respiratory viral infection in a subject.

In another aspect, the invention provides use of a compound of the invention as described herein or a pharmaceutically acceptable salt, solvate or prodrug thereof for treating and/or preventing a disease or condition associated with the TLR2 receptor.

In another aspect, the present invention further provides use of a compound of the invention as described herein or a pharmaceutically acceptable salt, solvate or prodrug thereof for agonising TLR2 in a cell.

The present invention also provides a kit for use, or when used, in a method of the invention, the kit comprising, consisting essentially of or consisting of:

a compound of the invention as described herein; and optionally written instructions describing the use of the compound in a method of the invention.

In yet another aspect, the present invention provides a process for preparing a compound of the invention. In some embodiments, the method comprises the steps outlined in the syntheses shown in the Examples.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 1. TLR2 activity of compounds 3, 4, 15 and 16 from the NK-κB luciferase assay described in Example 2.

DETAILED DESCRIPTION OF THE EMBODIMENTS

Figure 2:
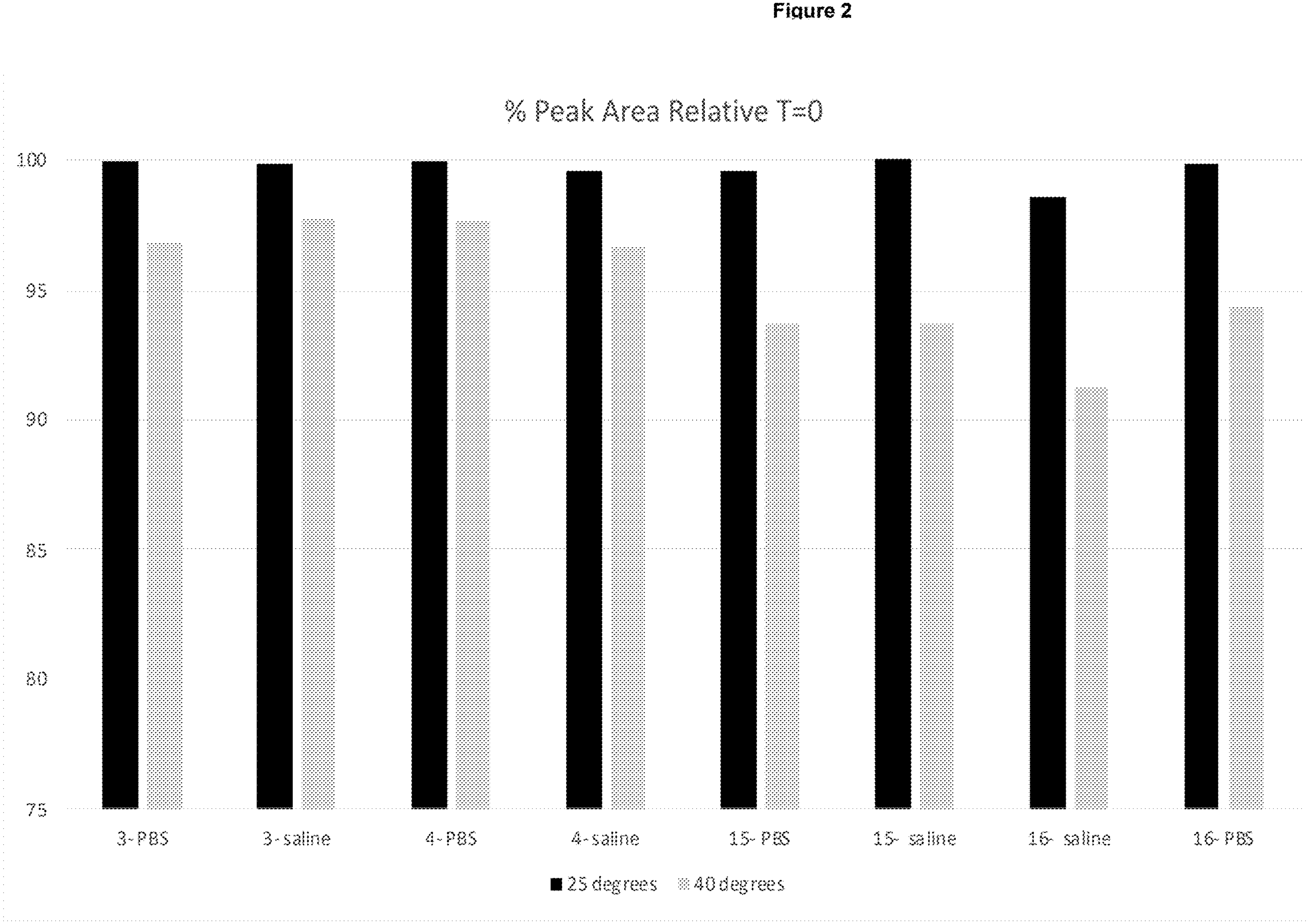
FIG. 2. Two-week (14 day) stability results of compounds 3, 4, 15 and 16 after being stored in either saline (0.9%) or phosphate buffered saline (PBS; pH 7.4) at either 25° C. or 40° C. relative to the percent peak area of the main HPLC peak at time zero, which was normalised to 100% to exclude the contribution of impurities to the total peak area.

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

As used herein, except where the context requires otherwise, the term "comprise" and variations of the term, such as "comprising", "comprises" and "comprised", are not intended to exclude further additives, components, integers or steps.

For purposes of interpreting this specification, terms used in the singular will also include the plural and vice versa.

The general chemical terms used in the formulae herein have their usual meaning.

The term "aliphatic" is intended to include saturated and unsaturated, nonaromatic, straight chain, branched, acyclic, and cyclic hydrocarbons. Those skilled in the art will appreciate that aliphatic groups include, for example, alkyl, alkenyl, alkynyl, cycloalkyl, and cycloalkenyl groups, and hybrids thereof such as (cycloalkyl)alkyl, (cycloalkenyl) alkyl and (cycloalkyl)alkenyl groups. In various embodiments, aliphatic groups comprise from 1-12, 1-8, 1-6, or 1-4 carbon atoms. In some embodiments, aliphatic groups comprise 5-21, from 9-21, or from 11-21 carbon atoms, such as from 11, 13, 15, 17, or 19 carbon atoms. In some embodiments, the aliphatic group is saturated.

The term "heteroaliphatic" is intended to include aliphatic groups, wherein one or more chain and/or ring carbon atoms are independently replaced with a heteroatom, preferably a heteroatom selected from oxygen, nitrogen and sulfur. In some embodiments, the heteroaliphatic is saturated. Examples of heteroaliphatic groups include linear or branched, heteroalkyl, heteroalkenyl, and heteroalkynyl groups.

The term "alkyl" is intended to include saturated straight chain and branched chain hydrocarbon groups. In some embodiments, alkyl groups have from 1 to 12, 1 to 10, 1 to 8, 1 to 6, or from 1 to 4 carbon atoms. In some embodiments, alkyl groups have from 5-21, from 9-21, or from 11-21 carbon atoms, such as from 11, 13, 15, 17, or 19 carbon atoms. Examples of straight chain alkyl groups include, but are not limited to, methyl, ethyl, n-propyl, n-butyl, n-pentyl, n-hexyl, n-heptyl, and n-octyl. Examples of branched alkyl groups include, but are not limited to, isopropyl, iso-butyl, sec-butyl, tert-butyl, neopentyl, isopentyl, and 2,2-dimethylpropyl.

The term "alkenyl" is intended to include straight and branched chain alkyl groups having at least one double bond between two carbon atoms. In some embodiments, alkenyl groups have from 2 to 12, from 2 to 10, from 2 to 8, from 2 to 6, or from 2 to 4 carbon atoms. In some embodiments, alkenyl groups have from 5-21, from 9-21, or from 11-21 carbon atoms, such as from 11, 13, 15, 17, or 19 carbon atoms.

In some embodiments, alkenyl groups have one, two, or three carbon-carbon double bonds. Examples of alkenyl groups include, but are not limited to, vinyl, allyl, $-CH{=}CH(CH_3)$, $-CH{=}C(CH_3)_2$, $-C(CH_3){=}CH_2$, and $-C(CH_3){=}CH(CH_3)$.

The term "alkynyl" is intended to include straight and branched chain alkyl groups having at least one triple bond between two carbon atoms. In some embodiments, the alkynyl group have from 2 to 12, from 2 to 10, from 2 to 8, from 2 to 6, or from 2 to 4 carbon atoms. In some embodiments, alkynyl groups have one, two, or three carbon-carbon triple bonds. Examples include, but are not limited to, $-C{\equiv}CH$, $-C{\equiv}CH_3$, $-CH_2C{\equiv}CH_3$, and $-C{\equiv}CH_2CH(CH_2CH_3)_2$.

The term "heteroalkyl" is intended to include alkyl groups, wherein one or more chain carbon atoms are replaced with a heteroatom, preferably a heteroatom selected from the group consisting of oxygen, nitrogen, and sulfur. In some embodiments, the heteroalkyl is saturated. Heteroalkyl groups include, for example, polyethylene glycol groups and polyethylene glycol ether groups, and the like.

The term "cycloalkyl" is intended to include mono-, bi- or tricyclic alkyl groups. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl. In some embodiments, the cycloalkyl group has from 3 to 8, from 3 to 7, from 3 to 6, from 4 to 6, from 3 to 5, or from 4 to 5 ring carbon atoms. Bi- and tricyclic ring systems include bridged, spiro, and fused cycloalkyl ring systems. Examples of bi- and tricyclic ring cycloalkyl systems include, but are not limited to, bicyclo[2.1.1]hexanyl, bicyclo[2.2.1]heptanyl, adamantyl, and decalinyl.

The term "cycloalkenyl" is intended to include non-aromatic cycloalkyl groups having at least one double bond between two carbon atoms. In some embodiments, cycloalkenyl groups have one, two or three double bonds. In some embodiments, cycloalkenyl groups have from 4 to 14, from 5 to 14, from 5 to 10, from 5 to 8, or from 5 to 6 carbon atoms in the ring(s). In some embodiments, cycloalkenyl groups have 5, 6, 7, or 8 ring carbon atoms. Examples of cycloalkenyl groups include cyclohexenyl, cyclopentenyl, cyclohexadienyl, butadienyl, pentadienyl, and hexadienyl.

The term "aryl" is intended to include cyclic aromatic hydrocarbon groups that do not contain any ring heteroatoms. Aryl groups include monocyclic, bicyclic and tricyclic ring systems. Examples of aryl groups include, but are not limited to, phenyl, azulenyl, heptalenyl, biphenyl, fluorenyl, phenanthrenyl, anthracenyl, indenyl, indanyl, pentalenyl, and naphthyl. In some embodiments, aryl groups have from 6 to 14, from 6 to 12, or from 6 to 10 carbon atoms in the ring(s). In some embodiments, the aryl groups are phenyl or naphthyl. Aryl groups include aromatic-aliphatic fused ring systems. Examples include, but are not limited to, indanyl and tetrahydronaphthyl.

The term "heterocyclyl" is intended to include non-aromatic ring systems containing 3 or more ring atoms, of which one or more is a heteroatom. In some embodiments, the heteroatom is nitrogen, oxygen, or sulfur. In some embodiments, the heterocyclyl group contains one, two, three, or four heteroatoms. In some embodiments, heterocyclyl groups include mono-, bi- and tricyclic rings having from 3 to 16, from 3 to 14, from 3 to 12, from 3 to 10, from 3 to 8, or from 3 to 6 ring atoms. Heterocyclyl groups include partially unsaturated and saturated ring systems, for example, imidazolinyl and imidazolidinyl. Heterocyclyl groups include fused and bridged ring systems containing a heteroatom, for example, quinuclidyl. Heterocyclyl groups include, but are not limited to, aziridinyl, azetidinyl, azepanyl, diazepanyl, 1,3-dioxanyl, 1,3-dioxolanyl, isoxazolidinyl, morpholinyl, piperazinyl, piperidinyl, pyranyl, pyrazolidinyl, pyrrolinyl, pyrrolidinyl, tetrahydrofuranyl, tetrahydrothienyl, thiadiazolidinyl, and trithianyl.

The term "heteroaryl" is intended to include aromatic ring systems containing 5 or more ring atoms, of which, one or more is a heteroatom. In some embodiments, the heteroatom is nitrogen, oxygen, or sulfur. In some embodiments, heteroaryl groups include mono-, bi- and tricyclic ring systems having from 5 to 16, from 5 to 14, from 5 to 12, from 5 to 10, from 5 to 8, or from 5 to 6 ring atoms. Heteroaryl groups include, but are not limited to, pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, pyrazolopyridinyl, triazolopyridinyl, benzotriazolyl, benzoxazolyl, benzothiazolyl, imidazopyridinyl, isoxazolopyridinylxanthinyl, guaninyl, quinolinyl, isoquinolinyl, tetrahydroquinolinyl, quinoxalinyl, and quinazolinyl. Heteroaryl groups include fused ring systems in which all of the rings are aromatic, for example, indolyl, and fused ring systems in which only one of the rings is aromatic, for example, 2,3-dihydroindolyl.

The term "halo" or "halogen" is intended to include F, $C_1$, Br, and I.

The term "heteroatom" is intended to include oxygen, nitrogen, sulfur, or phosphorus. In some embodiments, the heteroatom is selected from the group consisting of oxygen, nitrogen, and sulfur.

As used herein, the term "substituted" is intended to mean that one or more hydrogen atoms in the group indicated is replaced with one or more independently selected suitable substituents, provided that the normal valency of each atom to which the substituent(s) are attached is not exceeded, and that the substitution results in a stable compound. In some embodiments, optional substituents in the compounds described herein include but are not limited to halo, CN, $NO_2$, OH, $NH_2$, $NHR_{100}$, $NR_{100}R_{200}$, $C_{1-6}$haloalkyl, $C_{1-6}$haloalkoxy, $C(O)NH_2$, $C(O)NHR_{100}$, $C(O)NR_{100}R_{200}$, $SO_2R_{100}$, $OR_{100}$, $SR_{100}$, $S(O)R_{100}$, $C(O)R_{100}$, and $C_{1-6}$ aliphatic; wherein $R_{100}$ and $R_{200}$ are each independently $C_{1-6}$ aliphatic, for example $C_{1-6}$alkyl.

The term "carboxyl protecting group" as used herein is intended to mean a group that is capable of being readily removed to provide the OH group of a carboxyl group and protects the carboxyl group against undesirable reaction during synthetic procedures. Such protecting groups are described in Protective Groups in Organic Synthesis edited by T. W. Greene et al. (John Wiley & Sons, 1999) and 'Amino Acid—Protecting Groups' by Fernando Albericio (with Albert Isidro-Llobet and Mercedes Alvarez) Chemical Reviews 2009 (109) 2455-2504. Examples include, but are not limited to, alkyl and silyl groups, for example methyl, ethyl, tert-butyl, methoxymethyl, 2,2,2-trichloroethyl, benzyl, diphenylmethyl, trimethylsilyl, and tert-butyldimethylsilyl, and the like.

The term "amine protecting group" as used herein is intended to mean a group that is capable of being readily removed to provide the $NH_2$ group of an amine group and protects the amine group against undesirable reaction during synthetic procedures. Such protecting groups are described in Protective Groups in Organic Synthesis edited by T. W. Greene et al. (John Wiley & Sons, 1999) and 'Amino Acid—Protecting Groups' by Fernando Albericio (with Albert Isidro-Llobet and Mercedes Alvarez) Chemical Reviews 2009 (109) 2455-2504. Examples include, but are not limited to, acyl and acyloxy groups, for example acetyl, chloroacetyl, trichloroacetyl, o-nitrophenylacetyl, o-nitrophenoxy-acetyl, trifluoroacetyl, acetoacetyl, 4-chlorobutyryl, isobutyryl, picolinoyl, aminocaproyl, benzoyl, methoxy-carbonyl, 9-fluorenylmethoxycarbonyl, 2,2,2-trifluoroethoxycarbonyl, 2-trimethylsilylethoxy-carbonyl, tert-butyloxycarbonyl, benzyloxycarbonyl, p-nitrobenzyloxycarbonyl, 2,4-dichloro-benzyloxycarbonyl, and the like. Further examples include Cbz (carboxybenzyl), Nosyl (o- or p-nitrophenylsulfonyl), Bpoc (2-(4-biphenyl) isopropoxycarbonyl) and Dde (1-(4,4-dimethyl-2,6-dioxo-hexylidene)ethyl).

The term "carboxamide protecting group" as used herein is intended to mean a group that is capable of being readily removed to provide the $NH_2$ group of a carboxamide group and protects the carboxamide group against undesirable reaction during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Examples include, but are not limited to, 9-xanthenyl (Xan), trityl (Trt), methyltrityl (Mtt), cyclopropyldimethylcarbinyl (Cpd), and dimethylcyclopropylmethyl (Dmcp).

As used herein, the term "and/or" means "and", or "or", or both.

The term "(s)" following a noun contemplates the singular and plural form, or both.

The term "ester" refers to a carboxylic acid group where the hydrogen of the hydroxyl group has been replaced by a saturated, straight-chain (i.e. linear) or branched hydrocarbon group. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl. The alkyl group may be a $C_1$-$C_6$ alkyl group. As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range. The alkyl group may be a branched alkyl group.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As discussed above, the inventors have developed and optimised compounds for the treatment and/or prevention of respiratory diseases or conditions, particularly those associated with an infectious agent, such as bacteria or virus. Specifically, the compounds may provide significant protection against viral replication in the lung when those compounds are administered to the upper respiratory tract. These compounds may have greater efficacy than other known TLR2 agonists. The TLR2 agonist efficacy may also occur without significantly compromising TLR specificity and/or causing significant weight loss in the animal models described herein. Further, the compounds may demonstrate favourable stability, eg within a formulation and/or biological matrix environment, as they may be relatively resistant to hydrolytic and/or enzyme-mediated processes degradation. Compounds of the invention demonstrate improved solution stability compared to other related compounds.

In one aspect, the present invention provides a compound of Formula (I):

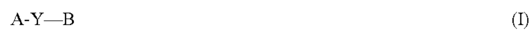

wherein A is:

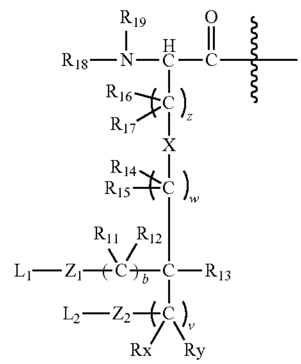

wherein b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(═O)— and —S(═O)$_2$—;

$Z_1$ and $Z_2$ are each independently selected from the group consisting of —O—, —NR—, —S—, —S(═O)—, —S(═O)$_2$—, —C(═O)O—, —OC(═O)—, —C(═O)NR—, —NRC(═O)—, —C(═O)S—, —SC(═O)—, —OC(═O)O—, NRC(═O)O—, —OC(═O)NR—, and —NRC(═O)NR—;

$R_{11}$, $R_{12}$, $R_x$, $R_y$, $R_{14}$, $R_{15}$, $R_{16}$, and $R_{17}$ are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(═O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

Y is

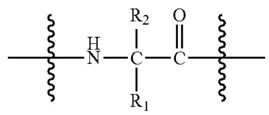

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C$(═O)$NH_2$, —$CH_2CH_2C$(═O)OH and —$CH_2CH_2C$(═O)$OR_8$, wherein any one of the alkyl hydrogens can be replaced with a halogen;

$R_8$ is selected from the group consisting of H and a straight or branched $C_1$-$C_6$ alkyl;

and

B comprises or consists of Polyethylene Glycol (PEG), or a pharmaceutically acceptable salt, solvate or prodrug thereof.

In some embodiments, v is an integer selected from 2, 3, 4 or 5. In some embodiments, v is 2.

In some embodiments, $R_x$, $R_y$, $R_{11}$, $R_{12}$, $R_{13}$, $R_{14}$, $R_{15}$, $R_{16}$, and $R_{17}$ are H.

In some embodiments, Z, and $Z_2$ are the same and selected from the group consisting of —O—, —NR—, —S—, S(═O), S(═O)$_2$—, —C(═O)O—, —OC(═O)—, —C(═O)NR—, —NRC(═O)—, —C(═O)S—, —SC(═O)—, OC(═O)O—, NRC(═O)O—, —OC(═O)NR—, and —NRC(═O)NR—.

In some embodiments, $Z_1$ and $Z_2$ are independently selected from the group consisting of —C(═O)O—, —OC(═O)—, —C(═O)NR—, —NRC(═O)—, —C(═O)S—, —SC(═O)—, —OC(═O)O—, —NRC(═O)O—, —OC(═O)NR—, and —NRC(═O)NR—.

In some embodiments, w is an integer selected from 1-7. In some embodiments, w is 1.

In some embodiments, b is 0.

In some embodiments, $R_{19}$ is selected from the group consisting of H, $C_1$-$C_6$ alkyl, —C(═O) $C_1$-$C_6$ alkyl or —C(═O)$C_{11}$-$C_{19}$alkyl.

In some embodiments, $L_1$ and $L_2$ are independently selected from $C_5$-$C_{21}$ aliphatic or $C_4$-$C_{20}$ heteroaliphatic. In some embodiments, $L_1$ and $L_2$ and independently selected from $C_{10}$-$C_{18}$ aliphatic or $C_{10}$-$C_{18}$ heteroaliphatic. In some embodiments, $L_1$ and $L_2$ are independently selected from $C_{14}$-alkyl and $C_{15}$-alkyl. In some embodiments, $L_1$ and $L_2$ are branched $C_{5-21}$ aliphatic. The branched $C_{5-21}$ aliphatic group may be branched at the carbon atom bonded to $Z_1$ or $Z_2$.

In some embodiments, the invention provides a compound of formula (I) wherein:

v is an integer selected from 2 to 5;

b is 0;

$R_x$, $R_y$, $R_{13}$, $R_{14}$, $R_{15}$, $R_{16}$, and $R_{17}$ are H;

$Z_1$ and $Z_2$ are independently selected from the group consisting of —C(═O)O—, —OC(═O)—, —C(═O)NR—, —NRC(═O)—, —C(═O)S—, —SC(═O)—, —OC(═O)O—, —NRC(═O)O—, —OC(═O)NR—, and —NRC(═O)NR—;

w is an integer selected from 1 to 7;

$R_{19}$ is selected from the group consisting of H, $C_1$-$C_6$ alkyl, —C(═O) $C_1$-$C_6$ alkyl or —C(═O)$C_{11}$-$C_{19}$alkyl; and $L_1$ and $L_2$ and independently selected from $C_{10}$-$C_{18}$ aliphatic or $C_{10}$-$C_{18}$ heteroaliphatic.

In some embodiments, X is S.

In some embodiments, X is S(═O).

In some embodiments, X is S(═O)$_2$.

In some embodiments, B denotes a substituted PEG.

In some embodiments, B is a substituted PEG according to the following formula B-I:

(B-I)

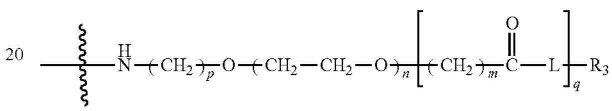

wherein n is 3 to 100;

m is 1, 2, 3 or 4;

p is 2, 3 or 4;

q is null or 1;

$R_3$ is H, —$NH_2$ or —OH, wherein when q is null, $R_3$ is H and when q is 1, $R_3$ is —$NH_2$ or —OH;

L is null or consists of 1 to 10 units, wherein each unit is a natural alpha amino acid or derived from a natural alpha amino acid, and has the formula:

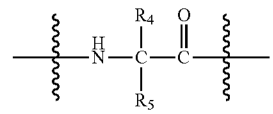

wherein $R_4$ is H; and $R_5$ is the side chain, or second hydrogen of the amino acid.

In some embodiments, B is a substituted PEG according to the following formula B-II:

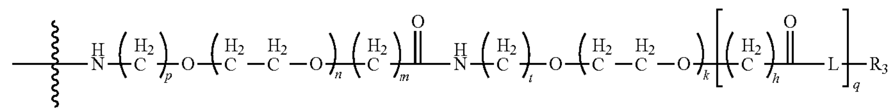

wherein p is 2, 3 or 4;

n is 3 to 100;

m is 1, 2, 3 or 4;

t is 2, 3 or 4;

k is 3 to 100;

his 1, 2, 3 or 4;

q is null or 1;

wherein when q is 1, $R_3$ is —$NH_2$ or —OH;

wherein when q is null, $R_3$ is H;

L is null or consists of 1 to 10 units, wherein each unit is a natural alpha amino acid or derived from a natural alpha amino acid, and has the formula:

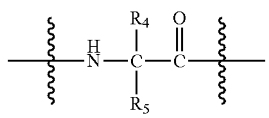

wherein $R_4$ is H; and $R_5$ is the side chain, or second hydrogen of the amino acid.

In some embodiments of the substituted PEG of formula B-I or B-II, q is 1.

In some embodiments of the substituted PEG of formula B-I or B-II, n may be from 10 to 14, such as 11, or from 24 to 30, such as 27.

In some embodiments of the substituted PEG of formula B-I or B-II, m is from 1 to 3, such as 2.

In some embodiments of the substituted PEG of formula B-I or B-II, when q is 1, $R_3$ is —$NH_2$.

In some embodiments of the substituted PEG of formula B-I or B-II, L is a natural alpha amino acid residue.

In another aspect, the invention provides a compound comprising a moiety (G) according to the following formula:

(G)

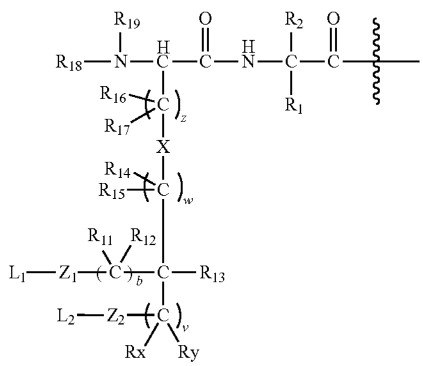

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any of the alkyl hydrogens can be replaced with a halogen;

$R_8$ is selected from the group consisting of H and a straight or branched $C_1$-$C_6$ alkyl;

$Z_1$, $L_1$, $Z_2$, $L_2$, X, b, w, v, z, $R_x$, $R_y$, $R_{11}$, $R_{12}$, $R_{13}$, $R_{14}$, $R_{15}$, $R_{16}$, $R_{17}$, $R_{18}$ and $R_{19}$ are as defined in the compound of formula (I) above;

covalently linked to polyethylene glycol (PEG), or a pharmaceutically acceptable salt, solvate or prodrug thereof.

In some embodiments, moiety G and PEG are directly linked through the covalent bond denoted by ⌇. Typically, the PEG is a substituted PEG and covalently linked at one end through an amide linker that includes the carbonyl group connected to the covalent bond denoted by ⌇.

In some embodiments, the PEG is a substituted PEG. In some embodiments, the substituted PEG is denoted by the following formula:

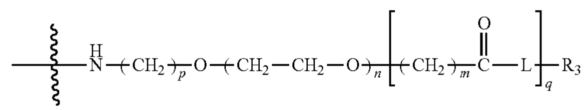

wherein n is 3 to 100;

m is 1, 2, 3 or 4;

p is 2, 3 or 4;

q is null or 1;

$R_3$ is H, —$NH_2$ or —OH, wherein when q is null, $R_3$ is H and when q is 1, $R_3$ is —$NH_2$ or —OH;

L is null or consists of 1 to 10 units, wherein each unit is a natural alpha amino acid or derived from a natural alpha amino acid, and has the formula:

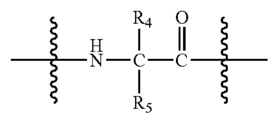

wherein $R_4$ is H; and $R_5$ is the side chain, or second hydrogen of the amino acid.

In some embodiments, when q is 1, $R_3$ is —$NH_2$.

In some embodiments, L is a natural alpha amino acid residue.

In one aspect, the present invention provides a compound of formula (VI):

(VI)

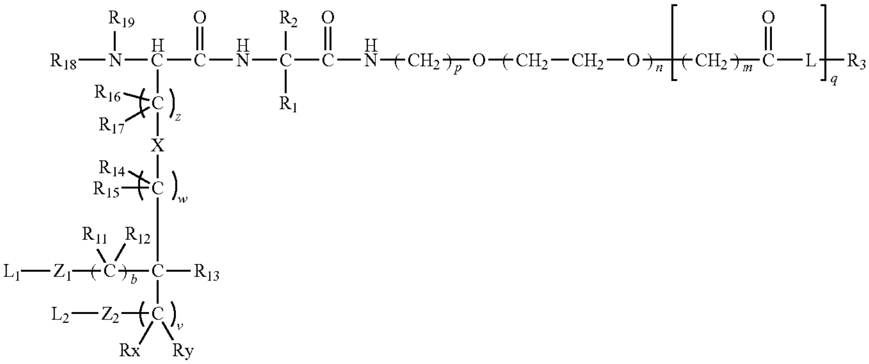

wherein n is 3 to 100;

m is 1, 2, 3 or 4;

p is 2, 3 or 4;

q is null or 1;

$R_1$ and $R_2$ are independently selected from the group consisting of H, —$CH_2OH$, —$CH_2CH_2OH$, —CH($CH_3$)OH, —$CH_2OPO(OH)_2$, —$CH_2C$(═O)$NH_2$, —$CH_2CH_2C$(═O)OH and $CH_2CH_2C$(═O)$OR_8$, wherein any one of the alkyl hydrogens can be replaced with a halogen;

$R_8$ is selected from the group consisting of H and a straight or branched $C_1$-$C_6$ alkyl;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

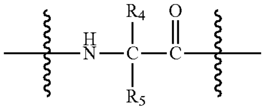

wherein $R_4$ is H; and $R_5$ is the side chain, or second hydrogen of the amino acid;

b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(═O)— and —S(═O)$_2$—;

$Z_1$ and $Z_2$ are each independently selected from the group consisting of —O—, —NR—, —S—, —S(═O)—, —S(═O)$_2$—, —C(═O)O—, —OC(═O)—, —C(═O)NR—, —NRC(═O)—, —C(═O)S—, —SC(═O)—, —OC(═O)O—, —NRC(═O)O—, —OC(═O)NR—, and —NRC(═O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(═O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

or a pharmaceutically acceptable salt, solvate or prodrug thereof.

In some embodiments of the compound of formula (VI), v is 2, 3, 4 or 5, preferably 2 or 3, most preferably 2.

In some embodiments of the compound of formula (VI), b is 0.

In some embodiments, of the compound of formula (VI), z is 1.

In some embodiments, the compound of formula (VI) is denoted by formula (VI'):

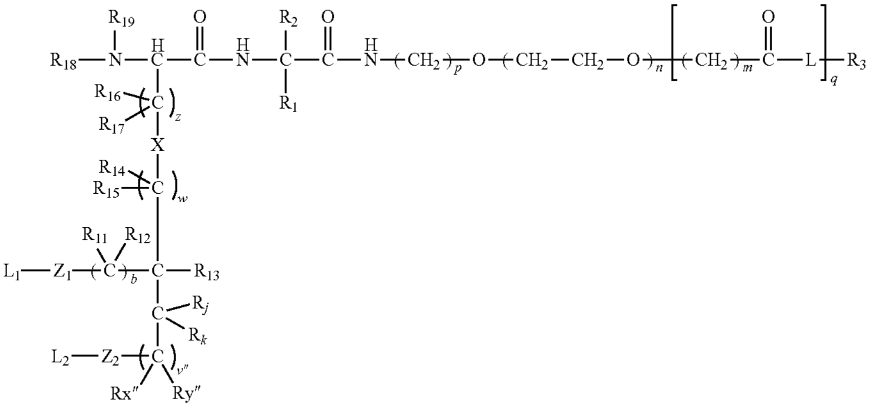

wherein $Z_1$, $L_1$, $Z_2$, $L_2$, X, b, w, z, $R_{11}$, $R_{12}$, $R_{13}$, $R_{14}$, $R_{15}$, $R_{16}$, $R_{17}$, $R_{18}$ and $R_{19}$ are as defined in the compound of formula (I) above;

$R_1$, $R_2$, p, n, m, L, q and $R_3$ are as defined in the compound of formula (VI) above;

v" is 1, 2, 3 or 4, preferably 1;

$R_j$ and $R_k$ are independently selected from H or $C_1$-$C_6$ aliphatic, preferably H; and each instance of $R_{x''}$ and $R_{y''}$ are independent selected from H or $C_1$-$C_6$ aliphatic, preferably H;

or a pharmaceutically acceptable salt, solvate or prodrug thereof.

In some embodiments, the compound is a compound of formula (VII):

$$A\text{-}Y—NH—(CH_2)_p—O—(CH_2—CH_2—O)_n—[(CH_2)_m—CO\text{-}L\text{-}]_qR_3 \quad (VII)$$

wherein A and Y are as defined for the compound of formula (I), and n is 3 to 100;

m is 1, 2, 3 or 4;

p is 2, 3 or 4;

q is null or 1;

wherein when q is 1, $R_3$ is —$NH_2$ or —OH;

wherein when q is null, $R_3$ is H;

L is null or consists of 1 to 10 units, wherein each unit is a natural alpha amino acid residue or derived from a natural alpha amino acid, and has the formula:

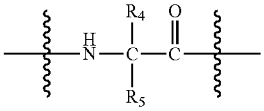

wherein $R_4$ is H; and $R_5$ is the side chain, or second hydrogen of the amino acid;

or a pharmaceutically acceptable salt, solvate or prodrug thereof.

In some embodiments, the compound is a compound of formula (X):

(X)

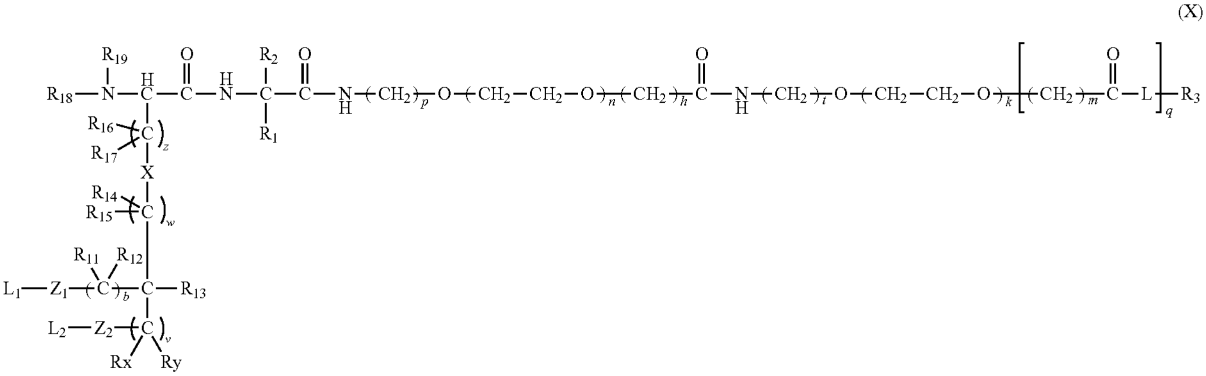

wherein n is 3 to 100;

k is 3 to 100;

m is 1, 2, 3 or 4;

p is 2, 3 or 4;

t is 2, 3 or 4;

h is 1, 2, 3 or 4;

q is null or 1;

wherein $R_1$ and $R_2$ are independently selected from the group consisting of H, $—CH_2OH$, $—CH_2CH_2OH$, $—CH(CH_3)OH$, $—CH_2OPO(OH)_2$, $—CH_2C({=}O)NH_2$, $—CH_2CH_2C({=}O)OH$ and $—CH_2CH_2C({=}O)OR_8$, wherein any one of the alkyl hydrogens can be replaced with a halogen;

$R_8$ is selected from the group consisting of H and a straight or branched $C_1$-$C_6$ alkyl;

wherein when q=1, $R_3$ is $—NH_2$ or —OH;

wherein when q=0, $R_3$ is H;

L is null or consists of 1 to 10 units, wherein each unit is a natural alpha amino acid or derived from a natural alpha amino acid, and has the formula:

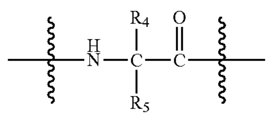

wherein $R_4$ is H; and $R_5$ is the side chain, or second hydrogen of the amino acid;

b and w are each independently an integer from 0 to 7 and v is an integer from 0 to 5, provided that:

the sum of b, v, and w is at least 3; and the sum of b and w is from 0 to 7;

z is 1 or 2;

X is selected from —S—, —S(=O)— and $—S(=O)_2—$;

$Z_1$ and $Z_2$ are each independently selected from the group consisting of —O—, —NR—, —S—, —S(=O)—, $—S(=O)_2—$, —C(=O)O—, —OC(=O)—, —C(=O)NR—, —NRC(=O)—, —C(=O)S—, —SC(=O)—, —OC(=O)O—, —NRC(=O)O—, —OC(=O)NR—, and —NRC(=O)NR—;

$R_{11}$, $R_{12}$, $R_x$, $R_y$, $R_{14}$, $R_{15}$, $R_{16}$, and $R_{17}$ at each instance of b, v, w, and z are each independently H or $C_1$-$C_6$ aliphatic;

R, $R_{13}$ and $R_{18}$ are each independently H or $C_1$-$C_6$ aliphatic;

Rig is H, $C_1$-$C_6$ aliphatic, an amino protecting group, $L_3$-C(=O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

or a pharmaceutically acceptable salt, solvate or prodrug thereof.

The present invention also provides for compositions containing a compound of the invention or a pharmaceutically acceptable salt, solvate or prodrug thereof, and a pharmaceutically acceptable carrier, diluent or excipient. Any of the compounds described herein or variations thereof may be included in the compositions of the invention.

As discussed above, the present invention provides Toll-Like Receptor 2 protein (TLR2) agonist compounds and their compositions. In humans, TLR2 plays a fundamental role in the recognition of pathogens and activation of the innate immunity response. It is encoded by the TLR2 gene and is expressed on the surface of specific cells.

Without wishing to be bound by any theory or mode of action, it is believed that the compounds of the invention described herein are agonists of TLR2 and show activity by binding at TLR2 and stimulating the innate immune system. The innate immune system forms an immediate defence against pathogens such as pathogens that infect and replicate in cells lining the respiratory tract. Research has shown that agents which stimulate the innate immune system may be useful for limiting respiratory infections, which may provide protection from infections both in isolation and during the period between inoculation and the formation of antibodies and immune cells. Such agents are considered to be useful for the treatment and/or prevention of respiratory infections, or respiratory conditions caused by or associated with infectious agents such as a virus (such as Influenza A) or bacterium (such as pneumonia) in a non-antigen specific manner.

In this regard, compounds of the invention as described herein may have activity, both activation of human TLR2 and inhibition of viral progression, that is at least comparable to other TLR2 agonists such as Pam2Cys-Ser-K4, Pam2Cys-Ser-Ser-PEG and Pam3Cys-Ser-PEG.

As used herein, 'Ser' refers to the amino acid serine and 'Cys' refers to the amino acid cysteine.

As used herein, 'PEG' refers to the polymer compound polyethylene glycol. Unless otherwise defined, reference to 'PEG' includes any length polymer of ethylene oxide. Reference to PEG also includes substituted PEG. In some embodiments, substituted PEG may be defined by formulas B-I or B-II as described herein.

In one aspect, therefore, the present invention provides a method of treating and/or preventing a disease, comprising raising an innate immune response in a subject by administering an effective amount of a compound of the invention as described herein or a pharmaceutically acceptable salt, solvate or prodrug thereof to the subject in need thereof.

In another aspect, the present invention provides a method of treating and/or preventing a disease caused by an infectious agent, comprising administering to a subject in need thereof an effective amount of a compound of the invention as described herein or a pharmaceutically acceptable salt, solvate or prodrug thereof.

In another aspect, the present invention provides a method of treating and/or preventing a respiratory disease or condition associated with a viral or bacterial infection, comprising administering to a subject in need thereof a compound of the invention as described herein or a pharmaceutically acceptable salt, solvate or prodrug thereof.

In another aspect, the present invention provides a method of treating and/or preventing a respiratory infection, comprising administering to a subject in need thereof a compound of the invention as described herein or a pharmaceutically acceptable salt, solvate or prodrug thereof. Preferably the method further comprises a step of identifying a subject having a respiratory infection.

In another aspect, the present invention provides a method for reducing airway inflammation, comprising administering to a subject in need thereof a compound of the invention as described herein or a pharmaceutically acceptable salt, solvate or prodrug thereof.

The present invention also provides a method of improving the ability of a subject to control a respiratory disease or condition during a respiratory viral infection, the method comprising administering to a subject in need thereof a compound of the invention as described herein or a pharmaceutically acceptable salt, solvate or prodrug thereof. Preferably the infection is not a rhinovirus infection.

The present invention also provides a method of treating and/or preventing a disease or condition associated with the TLR2 receptor, the method comprising administering to a subject in need thereof a compound of the invention as described herein or a pharmaceutically acceptable salt, solvate or prodrug thereof.

The present invention also provides a method of agonising TLR2 activity in a cell, the method comprising contacting the cell with a compound of the invention as described herein or a pharmaceutically acceptable salt, solvate or prodrug thereof. In some embodiments, the cell is contacted with the compound by administration of the compound or pharmaceutically acceptable salt, solvate or prodrug thereof, or composition comprising the compound, pharmaceutically acceptable salt, solvate or prodrug thereof, to a subject in need thereof. In some embodiments, the cell is provided in the form of a cell culture.

In another aspect, the present invention provides for use of a compound of the invention as described herein or a pharmaceutically acceptable salt, solvate or prodrug thereof in the preparation of a medicament for raising an innate immune response in a subject.

In another aspect, the present invention provides for use of a compound of the invention as described herein or a pharmaceutically acceptable salt, solvate or prodrug thereof in the preparation of a medicament for treating and/or preventing a disease caused by an infectious agent.

In another aspect, the present invention further provides for use of a compound of the invention as described herein or a pharmaceutically acceptable salt, solvate or prodrug thereof in the preparation of a medicament for treating and/or preventing a respiratory disease or condition associated with a viral or bacterial infection in a subject.

In another aspect, the present invention further provides for use of a compound of the invention as described herein or a pharmaceutically acceptable salt, solvate or prodrug thereof in the preparation of a medicament for treating and/or preventing a respiratory infection in a subject.

In yet another aspect, the present invention provides for use of a compound of the invention as described herein or a pharmaceutically acceptable salt, solvate or prodrug thereof in the preparation of a medicament for treating and/or preventing a respiratory infection.

In another aspect, the present invention further provides use of a compound of the invention as described herein or a pharmaceutically acceptable salt, solvate or prodrug thereof in the preparation of a medicament for reducing airway inflammation.

In another aspect, the present invention further provides use of a compound of the invention as described herein or a pharmaceutically acceptable salt, solvate or prodrug thereof in the preparation of a medicament for improving the ability of a subject to control a respiratory disease or condition during a respiratory viral infection. Preferably the infection is not a rhinovirus infection.

In another aspect, the present invention further provides use of a compound of the invention as described herein or a pharmaceutically acceptable salt, solvate or prodrug thereof in the preparation of a medicament for treating and/or preventing a disease or condition associated with the TLR2 receptor.

In one aspect, the present invention provides for use of a compound of the invention as described herein or a pharmaceutically acceptable salt, solvate or prodrug thereof, for raising an innate immune response in a subject.

In another aspect, the present invention provides for use of a compound of the invention as described herein or a pharmaceutically acceptable salt, solvate or prodrug thereof, for preventing a disease caused by an infectious agent, in a subject.

In another aspect, the present invention provides for use of a compound of the invention as described herein or a pharmaceutically acceptable salt, solvate or prodrug thereof, for treating and/or preventing a respiratory disease or condition associated with a viral or bacterial infection in a subject.

In a further aspect, the invention provides for use of a compound of the invention as described herein or a pharmaceutically acceptable salt, solvate or prodrug thereof, for (a) treating and/or preventing a respiratory infection in a subject; (b) reducing airway inflammation in a subject; (c) controlling a respiratory disease or condition during a respiratory viral infection in a subject; (d) for treating and/or preventing a disease or condition associated with the TLR2 receptor.

In any of these aspects, the compound may be administered in a composition. Typically, the composition further comprises a pharmaceutically acceptable carrier, diluent or excipient. The composition may be formulated for administration to the upper and/or lower respiratory tract, for example by inhalation or intranasally.

In any aspect of the invention, the compound of the invention as described herein or a pharmaceutically acceptable salt, solvate or prodrug thereof may be conjugated with other compounds. Other compounds are any of those described herein.

In any aspect of the invention, the compound of the invention as described herein or a pharmaceutically acceptable salt, solvate or prodrug thereof is administered once daily or once weekly.

In any aspect of the invention, where prevention or prophylaxis is intended or required, the compound is administered to the subject before any clinically or biochemically detectable symptoms of viral infection.

In any aspect of the invention, administration of the compound of the invention as described herein or a pharmaceutically acceptable salt, solvate or prodrug thereof to a subject reduces viral load in a subject. Preferably, the viral load is reduced in the respiratory tract, for example the upper and/or lower respiratory tract. Preferably, the viral load is reduced in the lungs.

In any aspect herein, the infectious agent may be a virus. Preferably, the virus is one associated with infection of the respiratory tract. Even more preferably, the virus is influenza. In any aspect, the virus is not a rhinovirus.

Influenza (commonly referred to as "the flu") is an infectious disease caused by RNA viruses of the family Orthomyxoviridae (the influenza viruses) that affects birds and mammals. The most common symptoms of the disease are chills, fever, sore throat, muscle pains, severe headache, coughing, weakness/fatigue and general discomfort.

The influenza viruses make up three of the five genera of the family Orthomyxoviridae. Influenza Type A and Type B viruses co-circulate during seasonal epidemics and can cause severe influenza infection. Influenza Type C virus infection is less common but can be severe and cause local epidemics.

Influenza Type A virus can be subdivided into different serotypes or subtypes based on the antibody response to these viruses. Influenza A viruses are divided into subtypes based on two proteins on the surface of the virus: the hemagglutinin (H) and the neuraminidase (N). There are 18 different hemagglutinin subtypes and 11 different neuraminidase subtypes. (H1 through H18 and N1 through N11 respectively.) The sub types that have been confirmed in humans are H1N1, H1N2, H2N2, H3N2, H5N1, H7N2, H7N3, H7N7, H9N2 and H10N7.

Influenza has an enormous impact on public health with severe economic implications in addition to the devastating health problems, including morbidity and even mortality. Accordingly, there is a need for therapeutic agents which can prevent infection, or reduce severity of infection in individuals.

In any aspect or embodiment of the invention, the influenza infection for which treatment or prevention is required is an infection with a virus selected from the group consisting of influenza Types A, B or C.

The term 'respiratory disease' or 'respiratory condition' refers to any one of several ailments that involve inflammation and affect a component of the respiratory system including the upper (including the nasal cavity, pharynx and larynx) and lower respiratory tract (including trachea, bronchi and lungs). The inflammation in the upper and lower respiratory tract may be associated with or caused by viral infection or an allergen. It is expected that the anti-inflammatory activity of the compounds either alone or when co-administered with a glucocorticoid would make them particularly suitable for treatment of these disease or conditions.

A symptom of respiratory disease may include cough, excess sputum production, a sense of breathlessness or chest tightness with audible wheeze. Exercise capacity may be quite limited. In asthma the FEV1.0 (forced expiratory volume in one second) as a percentage of that predicted nomographically based on weight, height and age, may be decreased as may the peak expiratory flow rate in a forced expiration. In COPD the FEV1.0 as a ratio of the FVC is typically reduced to less than 0.7. The impact of each of these conditions may also be measured by days of lost work/school, disturbed sleep, requirement for bronchodilator drugs, requirement for glucocorticoids including oral glucocorticoids.

The existence of, improvement in, treatment of or prevention of a respiratory disease may be determined by any clinically or biochemically relevant method of the subject or a biopsy therefrom. For example, a parameter measured may be the presence or degree of lung function, signs and symptoms of obstruction; exercise tolerance; night time awakenings; days lost to school or work; bronchodilator usage; Inhaled corticosteroid (ICS) dose; oral glucocorticoid (GC) usage; need for other medications; need for medical treatment; hospital admission.

As used herein, the term respiratory infection means an infection by virus or bacteria anywhere in the respiratory tract. Examples of respiratory infection include but are not limited to colds, sinusitis, throat infection, tonsillitis, laryngitis, bronchitis, pneumonia or bronchiolitis. Preferably, in any embodiment of the invention the respiratory infection is a cold.

An individual may be identified as having a respiratory tract infection by viral testing and may exhibit symptoms of itchy watery eyes, nasal discharge, nasal congestion, sneezing, sore throat, cough, headache, fever, malaise, fatigue and weakness. In one aspect, a subject having a respiratory infection may not have any other respiratory condition. Detection of the presence or amount of virus may be by PCR/sequencing of RNA isolated from clinical samples (nasal wash, sputum, BAL) or serology.

The term "pharmaceutically acceptable" may be used to describe any pharmaceutically acceptable salt, hydrate or prodrug, or any other compound which upon administration to a subject, is capable of providing (directly or indirectly) a compound of the invention as described herein, or a pharmaceutically acceptable salt, solvate or prodrug thereof, or an active metabolite or residue thereof.

Suitable pharmaceutically acceptable salts may include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts may include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "*Handbook of Pharmaceutical salts*" P. H. Stahl, C. G. Wermuth, 1st edition, 2002, Wiley-VCH.

In the case of compounds that are solids, it will be understood by those skilled in the art that the inventive compounds, agents, solvates and salts may exist in different crystalline or polymorphic forms, all of which are intended to be within the scope of the present invention and specified formulae.

The term "polymorph" includes any crystalline form of compounds of the invention as described herein, such as anhydrous forms, hydrous forms, solvate forms and mixed solvate forms.

It will be understood that compounds of the invention may possess a chiral centre and may therefore exist in an R- or S-configuration. The compounds may be provided in the form of a racemate or in an enatio- or diastereo-enriched form. Enantio- and diastereo-enriched forms of the compounds may be obtained either through asymmetric synthesis, the incorporation of chiral pool materials or through a stereoselective resolution. The compounds may therefore be provided as a purified enantiomer or diastereomer, or as a mixture of any ratio thereof. The isomers may be separated conventionally by chromatographic methods or using a resolving agent. Alternatively the individual isomers may be prepared by asymmetric synthesis using chiral intermediates. Where the compound has a carbon-carbon double bond, it may occur in Z- or E-form and all isomeric forms of the compounds being included in the present invention.

The compounds of the invention are intended to include, where applicable, solvated as well as unsolvated forms of the compounds. As used herein, the term "solvate" refers to a complex of variable stoichiometry formed by association of a solvent with a compound of the invention. The solvate may therefore comprise sub-stoichiometric amounts of the solvent, equimolar amounts of the solvent or super-stoichiometric amounts of the solvent relative to the compound of the invention. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Solvates wherein the solvent is water may be referred to as hydrates.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds as described herein are to also include isotope variations, such as the replacement of hydrogen for deuterium.

Compounds of the present invention may exist in and be isolated in optically active and racemic forms. As would be understood by a person skilled in the art, the present invention is intended to encompass any racemic, optically active or stereoisomeric form, or mixtures thereof, of compounds of the invention which possess the useful properties described herein. It is well known in the art how to prepare such forms (for example, by resolution of racemic mixtures by recrystallization, by synthesis from optically-active starting materials, by chiral synthesis, or by chiral chromatographic separation). In one preferred embodiment, with regard to the carbon shown with a * below, the compound of the present invention is provided in a racemic mixture. In another preferred aspect, the compound of the present invention contains

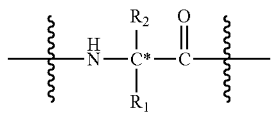

provided with excess of, or only, the L-configuration or naturally occurring amino acid.

In any aspect or embodiment of the invention, a compound of the present invention may be provided in a chiral form enriched at a chiral centre at the following carbon atom (shown at *) of moiety A:

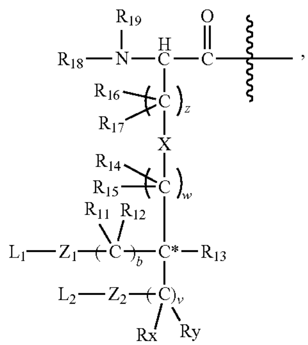

wherein the chiral centre is in the R configuration. In some embodiments, this stereoisomer of the compound may be depicted as:

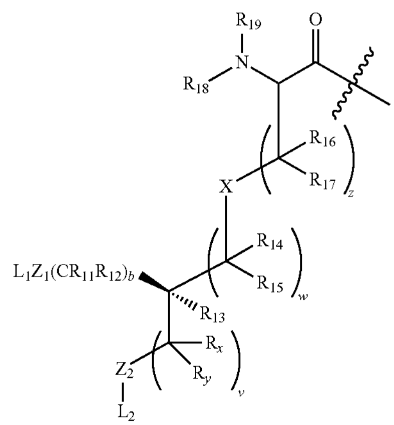

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, $R_{19}$, b, v and z are as defined for the compound of Formula (I) and w is 1. Other stereocentres in these compounds may be racemic or enriched in either the R or S configuration.

In any aspect or embodiment of the invention, a compound of the present invention may be provided in a chiral form enriched at a chiral centre at the following carbon atom (shown at *) of moiety A:

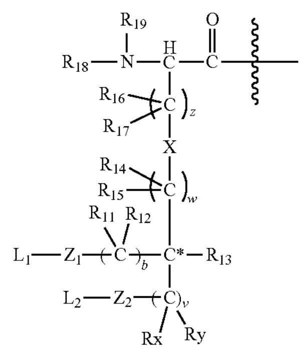

wherein the chiral centre is in the S configuration. In some embodiments, moiety A of this stereoisomer of the compound may be depicted as:

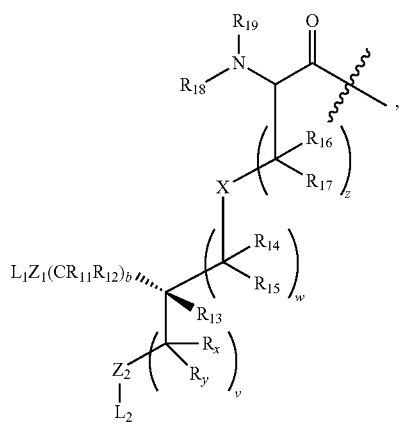

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, $R_{19}$, b, v, w, and z are as defined for the compound or Formula (I). Other stereocentres in these compounds may be racemic or enriched in either the R or S configuration.

In any aspect or embodiment of the invention, a compound of the present invention may be provided in a chiral form enriched at a chiral centre at the following carbon atom (shown at **) of moiety A:

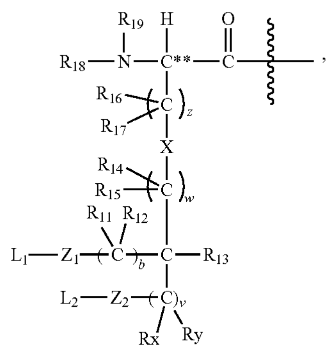

wherein the chiral centre is in the L configuration. A compound in this form may also be referred to as an L-Cys analogue stereoisomer of a compound of the invention. In some embodiments, this stereoisomer of the compound may be depicted as:

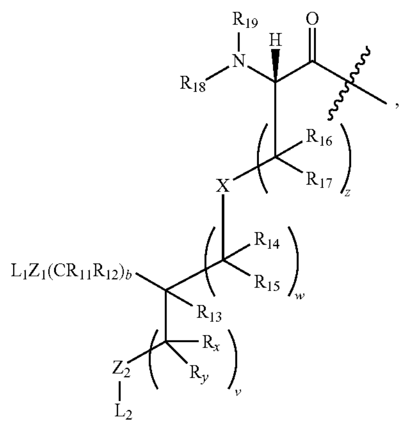

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, $R_{19}$, b, v, w, and z are as defined for the compound or Formula (I). Other stereocentres in these compounds may be racemic or enriched in either the R or S configuration.

In any aspect or embodiment of the invention, a compound of the present invention may be provided in a chiral form enriched at a chiral centre at the following carbon atom (shown at **) of moiety A:

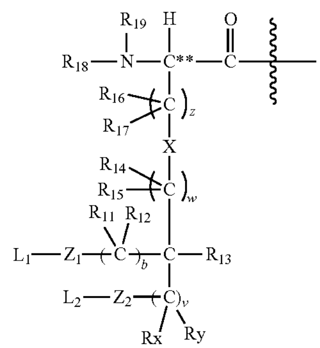

wherein the chiral centre is in the D configuration. A compound in this form may also be referred to as a D-Cys analogue stereoisomer of a compound of the invention. In some embodiments, moiety A of this stereoisomer of the compound may be depicted as:

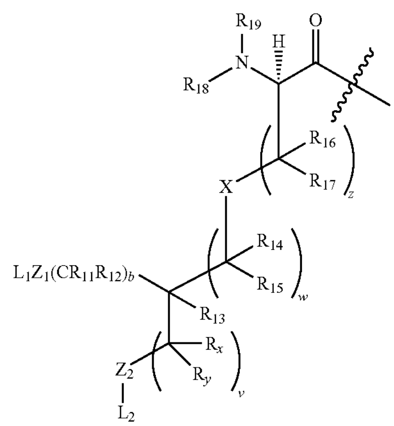

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, $R_{19}$, b, v and z are as defined for the compound or Formula (I) and w is 1. Other stereocentres in these compounds may be racemic or enriched in either the R or S configuration.

In any aspect or embodiment of the invention, a compound of the present invention may be provided in a chiral form enriched at chiral centres at the following carbon atoms (shown at * and **) of moiety A:

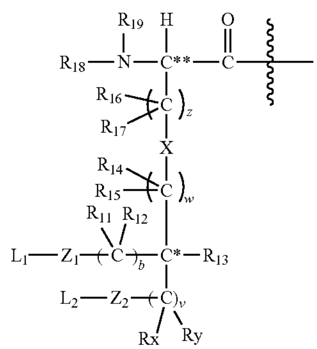

wherein the chiral centre * is in the R configuration and the chiral centre ** is in the R configuration. A compound in this form may also be referred to as an R,R-Cys analogue stereoisomer of a compound of the invention. In some embodiments, this stereoisomer of the compound may be depicted as:

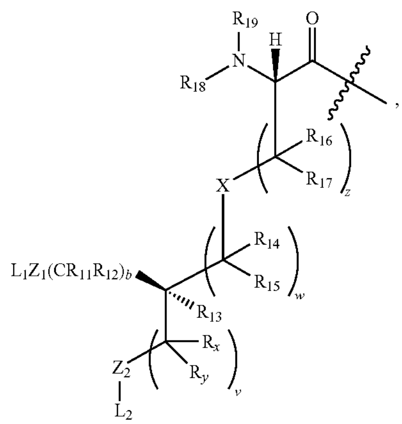

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, and $R_{19}$ are as defined for the compound of Formula (I), b is 0, v is 1, z is 1 and w is 1. Other stereocentres in these compounds may be racemic or enriched in either the R or S configuration.

In any aspect or embodiment of the invention, a compound of the present invention may be provided in a chiral form enriched at chiral centres at the following carbon atoms (shown at * and **) of moiety A:

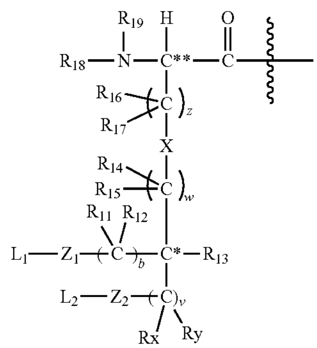

wherein the chiral centre * is in the S configuration and the chiral centre ** is in the R configuration. A compound in this form may also be referred to as an S,R-Cys analogue stereoisomer of a compound of the invention. In some embodiments, moiety A of this stereoisomer of the compound may be depicted as:

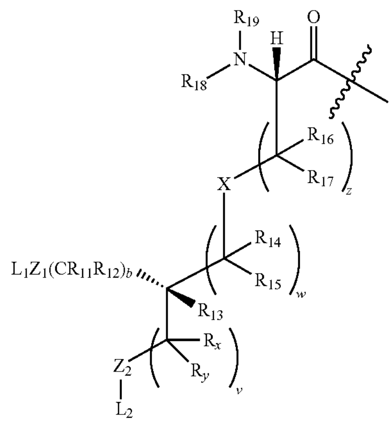

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, and $R_{19}$ are as defined for the compound of Formula (I), b is 0, v is 1, z is 1 and w is 1. Other stereocentres in these compounds may be racemic or enriched in either the R or S configuration.

In any aspect or embodiment of the invention, a compound of the present invention may be provided in a chiral form enriched at chiral centres at the following carbon atoms (shown at * and **) of moiety A:

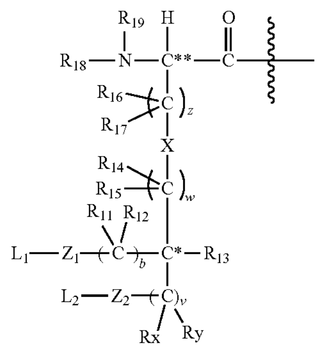

wherein the chiral centre * is in the S configuration and the chiral centre ** is in the S configuration. A compound in this form may also be referred to as an S,S-Cys analogue stereoisomer of a compound of the invention. In some embodiments, moiety A of this stereoisomer of the compound may be depicted as:

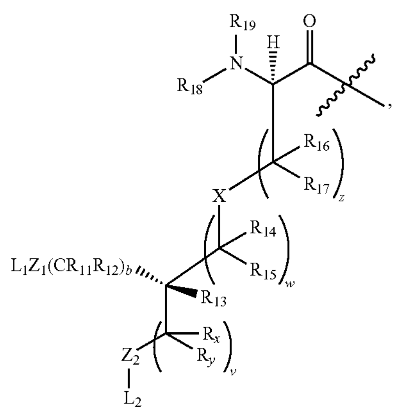

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, and $R_{19}$ are as defined for the compound of Formula (c), b is 0, v is 1, z is i and w is i. Other stereocentres in these compounds may be racemic or enriched in either the R or S configuration.

In any aspect or embodiment of the invention, a compound of the present invention may be provided in a chiral form enriched at chiral centres at the following carbon atoms (shown at * and **) of moiety A:

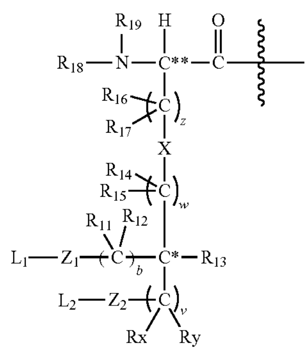

wherein the chiral centre * is in the R configuration and the chiral centre ** is in the S configuration. A compound in this form may also be referred to as an R,S-Cys analogue stereoisomer of a compound of the invention. In some embodiments, moiety A of this stereoisomer of the compound may be depicted as:

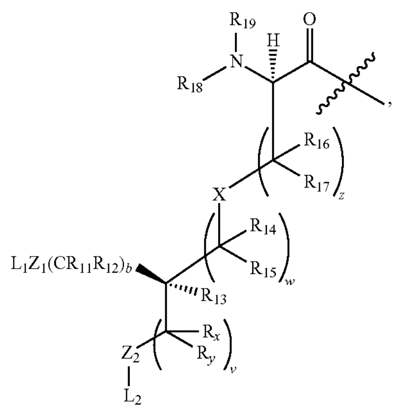

wherein $L_1$, $L_2$, $Z_1$, $Z_2$, $R_x$, $R_y$, $R_{11}$, $R_{12}$, $R_{13}$, $R_{14}$, $R_{15}$, $R_{16}$, $R_{17}$, $R_{18}$, and $R_{19}$ are as defined for the compound of Formula (I), b is 0, v is 1, z is 1 and w is 1. Other stereocentres in these compounds may be racemic or enriched in either the R or S configuration.

In any aspect or embodiment of the invention, a compound of the present invention comprises a chiral centre in the Y moiety of the compound (shown at ***):

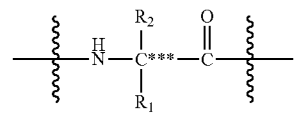

wherein the chiral centre is in the L-configuration. A compound in this form may also be referred to as an L-Y stereoisomer of a compound of the invention. The stereochemistry of the chiral centre in the L-Y stereoisomer may be combined without limitation with other chiral centres of the compound, such as in moiety A as described herein.

In any aspect or embodiment of the invention, a compound of the present invention comprises a chiral centre in the Y moiety of the compound (shown at ***):

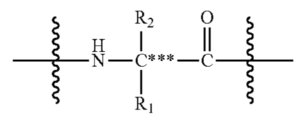

wherein the chiral centre is in the D-configuration. A compound in this form may also be referred to as an D-Y stereoisomer of a compound of the invention. The stereochemistry of the chiral centre in the D-Y stereoisomer may be combined without limitation with other chiral centres of the compound, such as in moiety A as described herein.

In any aspect of the present invention, 1%, 5%, 10%, 20%, 30%, 40%, 50%, 60%, 70%, 80%, 90%, 95%, 96%, 97%, 98%, 99% or more than 99% of the compound present in a composition is the R diastereomer around the chiral centre denoted * in the moiety A of the compound described herein.

In any aspect of the present invention, 1%, 5%, 10%, 20%, 30%, 40%, 50%, 60%, 70%, 80%, 90%, 95%, 96%, 97%, 98%, 99% or more than 99% of the compound present in a composition is the S diastereomer around the chiral centre denoted * in the moiety A of the compound described herein.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the R diastereomer around the chiral centre denoted ** in the moiety A of the compound described herein.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the S diastereomer around the chiral centre denoted ** in the moiety A of the compound described herein.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the R diastereomer around the chiral centre denoted *** of the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the S diastereomer around the chiral centre denoted *** of the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the R diastereomer around the chiral centre denoted * in moiety A, the R diastereomer around the chiral centre denoted  in moiety A and the R diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the R diastereomer around the chiral centre denoted * in moiety A, the S diastereomer around the chiral centre denoted  in moiety A and the R diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the R diastereomer around the chiral centre denoted * in moiety A, the R diastereomer around the chiral centre denoted  in moiety A and the S diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the R diastereomer around the chiral centre denoted * in moiety A, the S diastereomer around the chiral centre denoted  in moiety A and the S diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the S diastereomer around the chiral centre denoted * in moiety A, the R diastereomer around the chiral centre denoted  in moiety A and the R diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the S diastereomer around the chiral centre denoted * in moiety A, the S diastereomer around the chiral centre denoted  in moiety A and the R diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the S diastereomer around the chiral centre denoted * in moiety A, the R diastereomer around the chiral centre denoted  in moiety A and the S diastereomer around the chiral centre denoted * in the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the S diastereomer around the chiral centre denoted * in moiety A, the S diastereomer around the chiral centre denoted  in moiety A and the S diastereomer around the chiral centre denoted * in the Y moiety.

The compounds of the invention demonstrate improved solution stability under accelerated degradation conditions relative to other related compounds. Solution stability may be assess by measuring the concentration of compound in a solution at day 0 and comparing the concentration of the compound after a period of time, such as 14 days. Solution stability may be assessed under ambient conditions, eg 25° C. and 65% relative humidity, or under accelerated conditions, eg 40° C. and 75% relative humidity. Typically, an acceptable stability for a compound of interest for the indications of the invention when stored for 14 days in solution under accelerated conditions would be retention of at least 80% concentration in the solution of the compound relative to the initial concentration of the compound in the solution. Typically, the solution may be a saline solution (eg 0.9% aq. NaCl) or phosphate-buffered saline (PBS; eg pH 7.4). In some embodiments, the compounds of the invention after 14 day storage in pH 7.4 PBS buffer is at least about 80%, 85%, 90%, 91%, 92% or greater relative to the amount of compound detected in the solution at day 0.

A "prodrug" is a compound that may not fully satisfy the structural requirements of the compounds provided herein, but is modified in vivo, following administration to a subject or patient, to produce a compound of the invention as described herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (eg, two, three or four) amino acid residues which are covalently joined to free amino, and amido groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of a compound of the invention.

The compounds of the invention as described herein or a pharmaceutically acceptable salt, solvate or prodrug thereof may be covalent irreversible or covalent reversible agonists of the active site of a protein.

Where a protecting group (PG) is referred to, a person skilled in the art would readily understand what type of protecting group would be suitable. Examples of suitable amine protecting groups for the purposes described herein include (but are not limited to) tert-butyloxycarbonyl (t-Boc) and 9H-fluoren-9-ylmethoxycarbonyl (Fmoc).

Pharmaceutical compositions may be formulated from compounds of the invention as described herein for any appropriate route of administration including, for example, topical (for example, transdermal or ocular), oral, buccal, respiratory (for example, nasal, inhalation, intrapulmonary), vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. Suitable oral forms include, for example, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials. Examples of components are described in Martindale—The Extra Pharmacopoeia (Pharmaceutical Press, London 1993) and Martin (ed.), Remington's Pharmaceutical Sciences. Preferably, the compositions are formulated for administration to the respiratory tract, for example, by intrapulmonary administration (eg. inhalation) or intranasal administration. The compositions may be administered to the upper and/or lower respiratory tract.

Preferably, the pharmaceutical compositions are in a form suitable for administration via the respiratory route, and may be in any form such as a powder, liquid or suspension. Such compositions may target tissue including pulmonary tissue (including alveolus, terminal bronchiole, bronchiole, and bronchus) or the nasal cavity (including paranasal cavity, frontal sinus, ethmoid sinus, maxillary sinus, sphenoidal sinus, superior turbinate, middle turbinate, and inferior turbinate).

In the context of this specification the term "administering" and variations of that term including "administer" and "administration", includes contacting, applying, delivering or providing a compound or composition of the invention to an organism, or a surface by any appropriate means.

The dose of the biologically active compound according to the invention may vary within wide limits and may be adjusted to individual requirements. Active compounds according to the present invention are generally administered in a therapeutically effective amount.

A composition according to the present invention is to be administered in an effective amount. The phrase 'therapeutically effective amount' or 'effective amount' generally refers to an amount of a compound of the invention described herein, a pharmaceutically acceptable salt, polymorph or prodrug thereof of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein. Undesirable effects, e.g. side effects, are sometimes manifested along with the desired therapeutic effect; hence, a practitioner balances the potential benefits against the potential risks in determining what is an appropriate "effective amount".

The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. In one aspect, the dose administered to a subject is any dose that reduces viral load. Preferably, the dose does not significantly increase inflammation, for example does not significantly increase absolute neutrophil numbers or the proportion of neutrophils of total BAL cells in the lung. The terms "therapeutically effective amount" or "effective amount" may also refer to an amount of the compound of Formula (I), Formula (II), Formula (III) Formula (IV) and/or Formula (V) or a pharmaceutically acceptable salt, solvate or prodrug thereof, that results in an improvement or remediation of the symptoms of a respiratory infection, or respiratory disease or condition associated with a viral or bacterial infection.

In some embodiments, an effective amount for a human subject lies in the range of about 250 nmoles/kg body weight/dose to 0.005 nmoles/kg body weight/dose. Preferably, the range is about 250 nmoles/kg body weight/dose to 0.05 nmoles/kg body weight/dose. In some embodiments, the body weight/dose range is about 250 nmoles/kg, to 0.1 nmoles/kg, about 50 nmoles/kg to 0.1 nmoles/kg, about 5 nmoles/kg to 0.1 nmol/kg, about 2.5 nmoles/kg to 0.25 nmoles/kg, or about 0.5 nmoles/kg to 0.1 nmoles/kg body weight/dose. In some embodiments, the amount is at, or about, 250 nmoles, 50 nmoles, 5 nmoles, 2.5 nmoles, 0.5 nmoles, 0.25 nmoles, 0.1 nmoles or 0.05 nmoles/kg body weight/dose of the compound. Dosage regimes are adjusted to suit the exigencies of the situation and may be adjusted to produce the optimum therapeutic dose.

Compounds of the invention described herein may be compositions formulated as inhaled formulations, including dry powder, sprays, mists, or aerosols. This may be particularly preferred for treatment of a respiratory infection. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient. Alternatively, the composition may be a dry powder and administered to the respiratory tract as defined herein.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

It will be understood, however, that the specific dose level for any particular subject will depend upon a variety of factors including the activity of the specific compound employed, the age, body weight, general health, sex, diet, time of administration, route of administration, and rate of excretion, drug combination (i.e. other drugs being used to treat the subject), and the severity of the particular disorder undergoing therapy. The dosage will generally be lower if the compounds are administered locally rather than systemically, and for prevention rather than for treatment. Such treatments may be administered as often as necessary and for the period of time judged necessary by the treating physician. A person skilled in the art will appreciate that the dosage regime or therapeutically effective amount of the compound of the invention, or a pharmaceutically acceptable salt, solvate or prodrug thereof, to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in a single or multiple doses per day.

It will also be appreciated that different dosages may be required for treating different disorders.

As used herein, the terms "treatment" or "treating" of a subject includes the application or administration of a compound or composition of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

"Subject" includes any human or non-human animal. Thus, in addition to being useful for human treatment, the compounds of the present invention may also be useful for veterinary treatment of mammals, including companion animals and farm animals, such as, but not limited to dogs, cats, horses, cows, sheep, and pigs.

The compounds of the present invention may be administered along with a pharmaceutical carrier, diluent or excipient as described above.

| Compound Structure | Compound name |
| --- | --- |
| 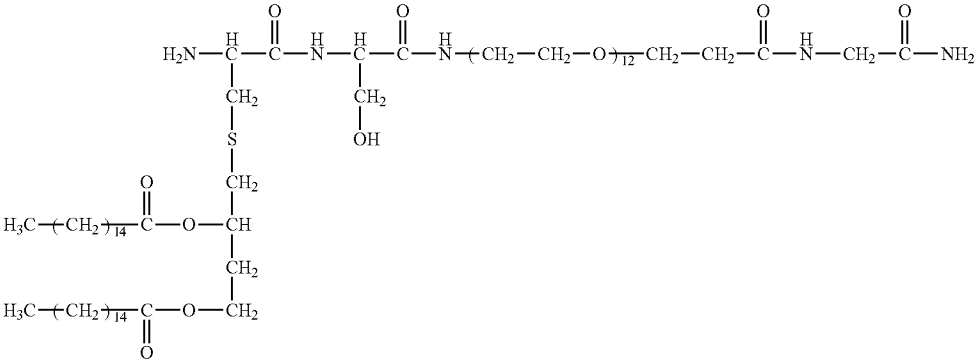 | Compound 1 |
| 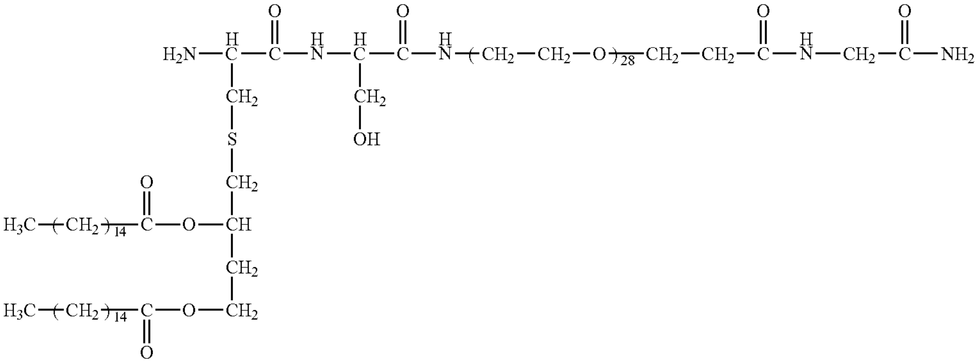 | Compound 2 |

-continued
| Compound Structure | Compound name |
|---|---|
| 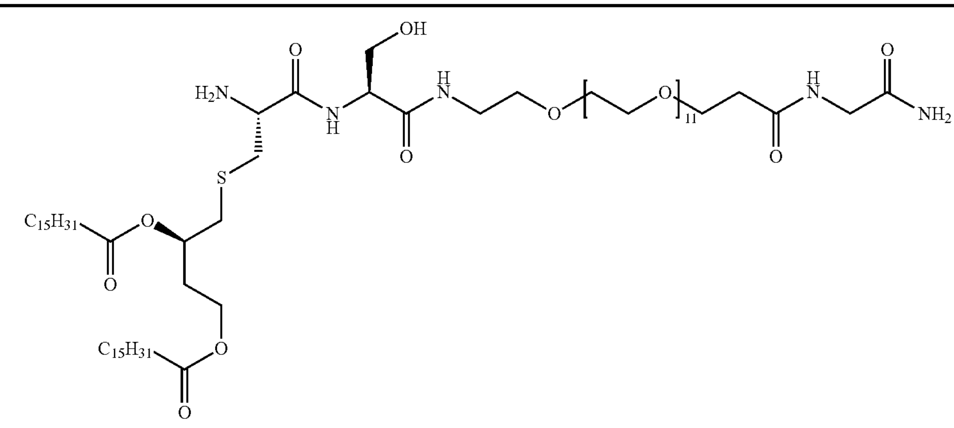 | Compound 3 |
| 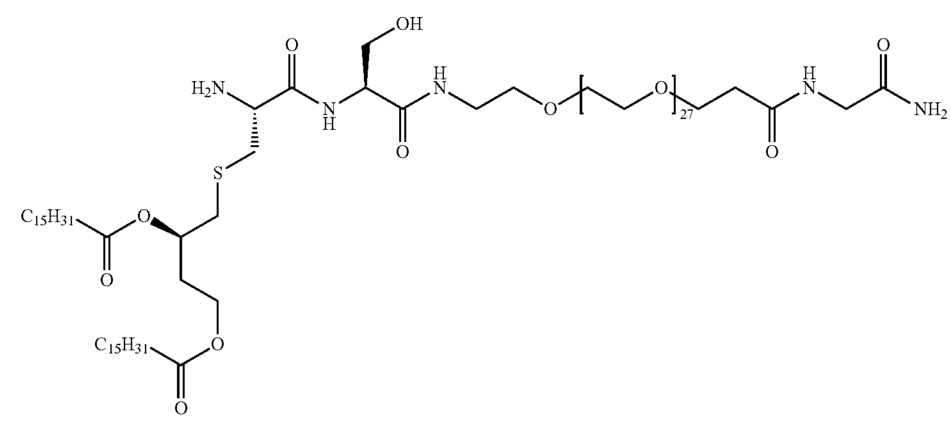 | Compound 4 |
| 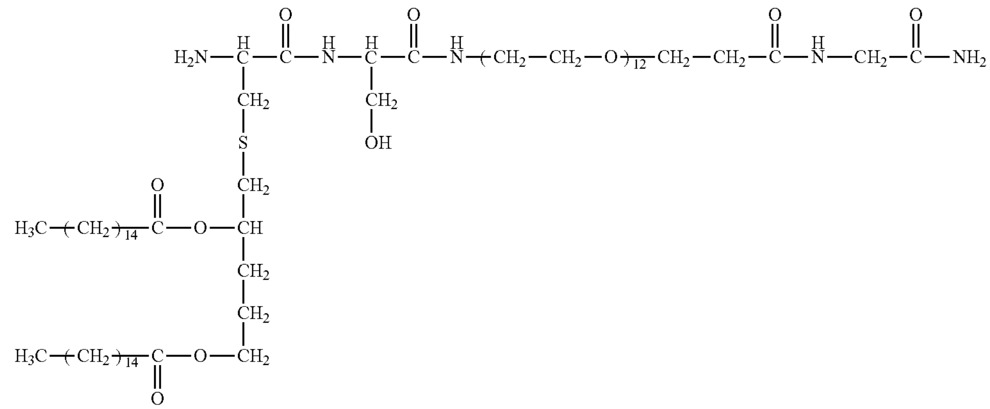 | Compound 5 |

-continued
| Compound Structure | Compound name |
|---|---|
| 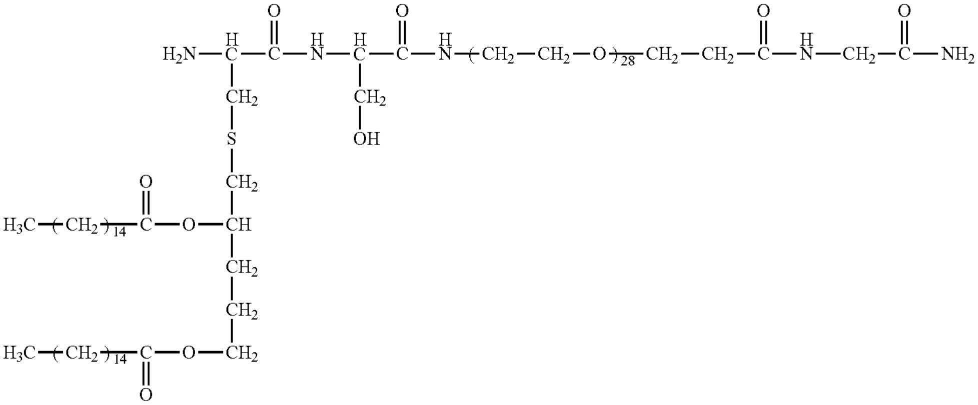 | Compound 6 |
| 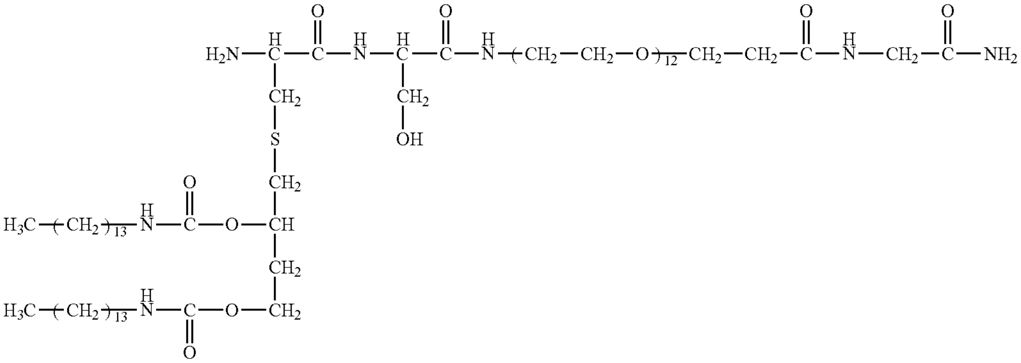 | Compound 7 |
| 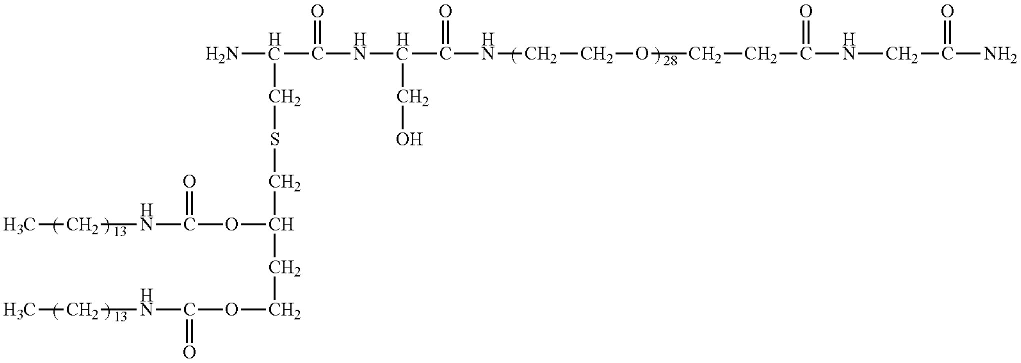 | Compound 8 |
| 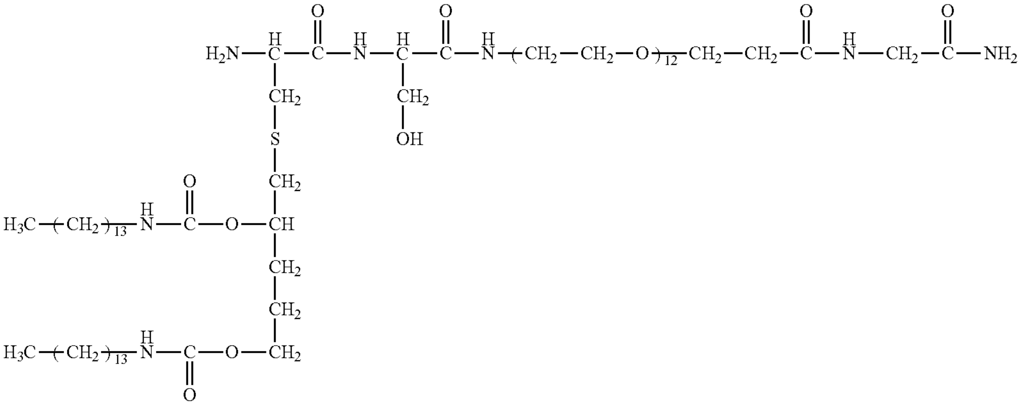 | Compound 9 |

-continued
| Compound Structure | Compound name |
|---|---|
| 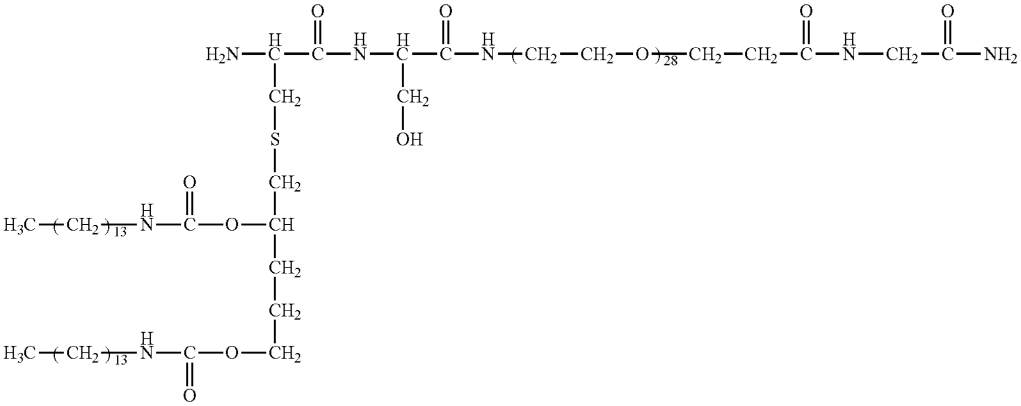 | Compound 10 |
| 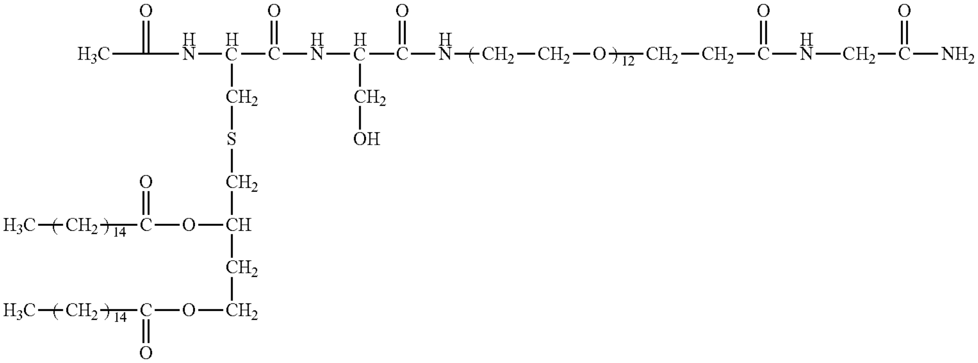 | Compound 11 |
| 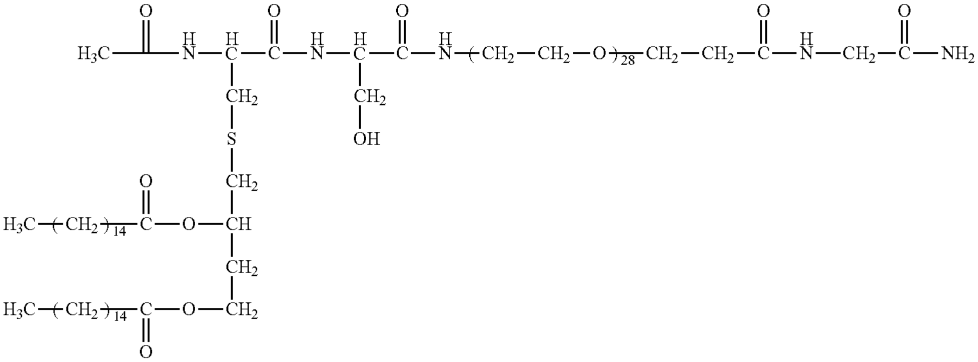 | Compound 12 |
| 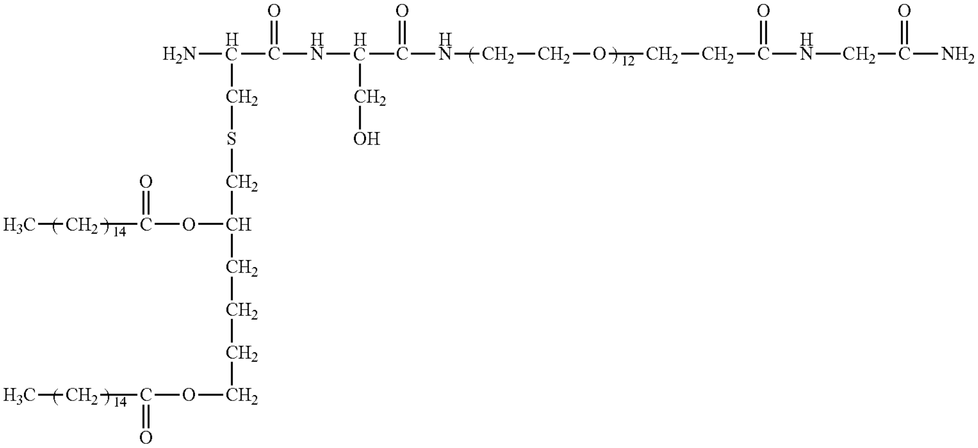 | Compound 13 |

-continued
| Compound Structure | Compound name |
| --- | --- |
| 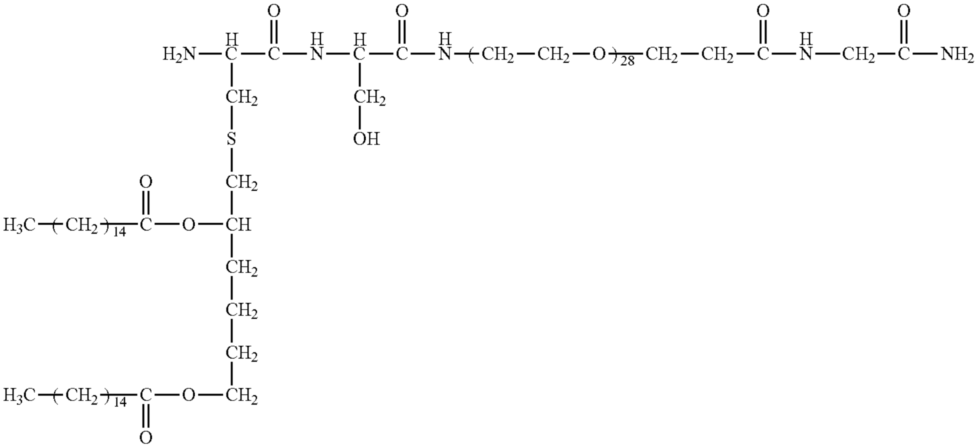 | Compound 14 |
| 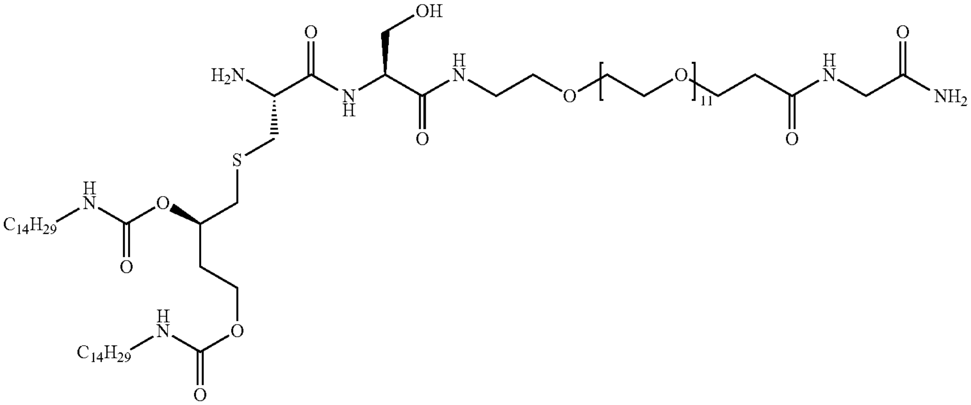 | Compound 15 |
| 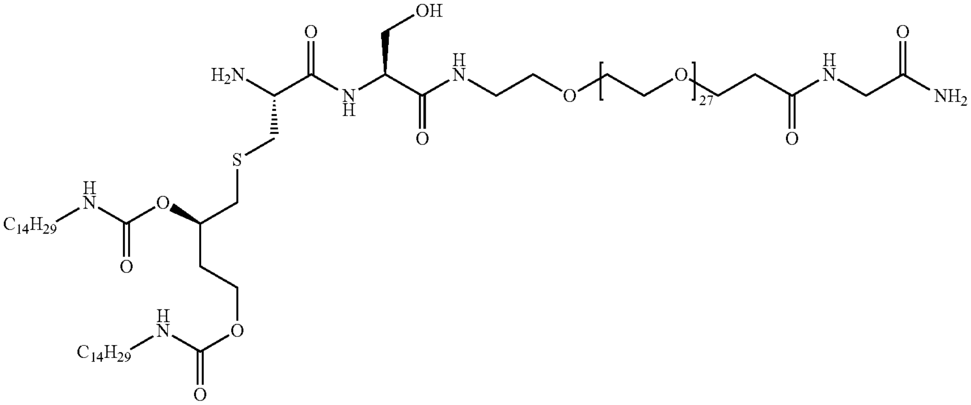 | Compound 16 |

-continued
| Compound Structure | Compound name |
| --- | --- |
| 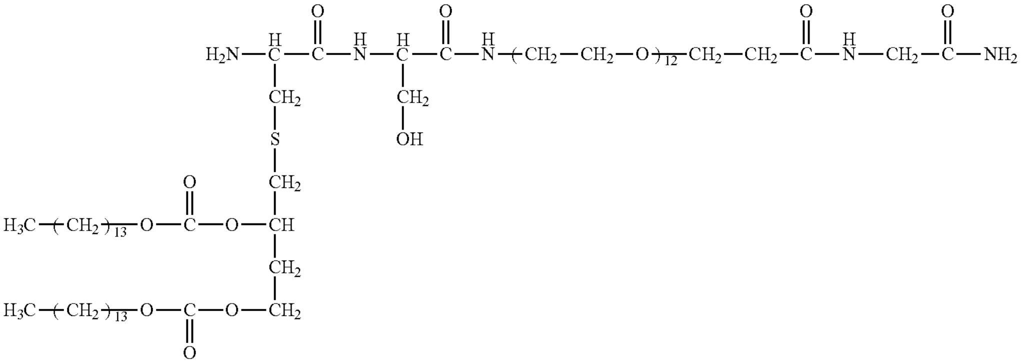 | Compound 17 |
| 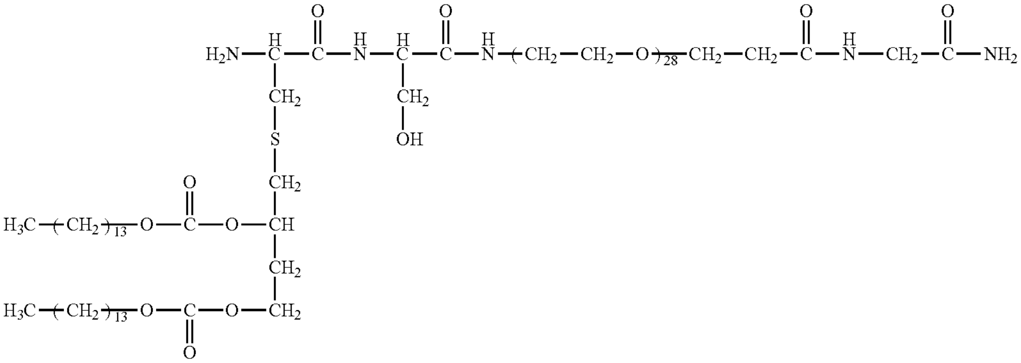 | Compound 18 |
| 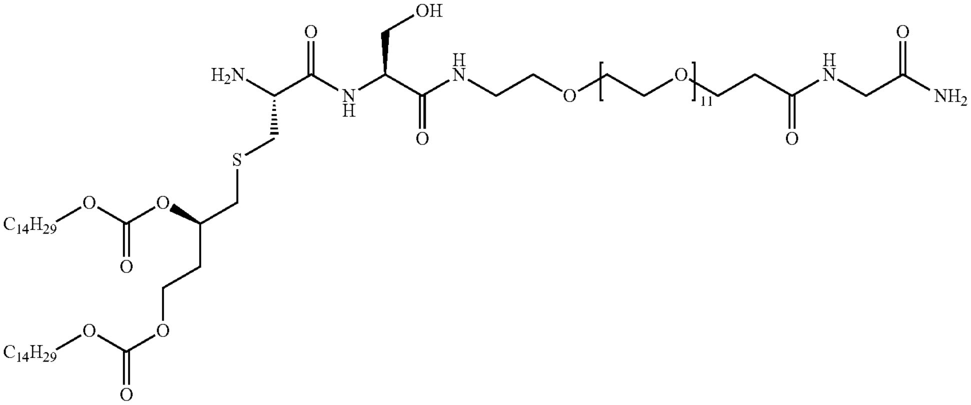 | Compound 19 |
| 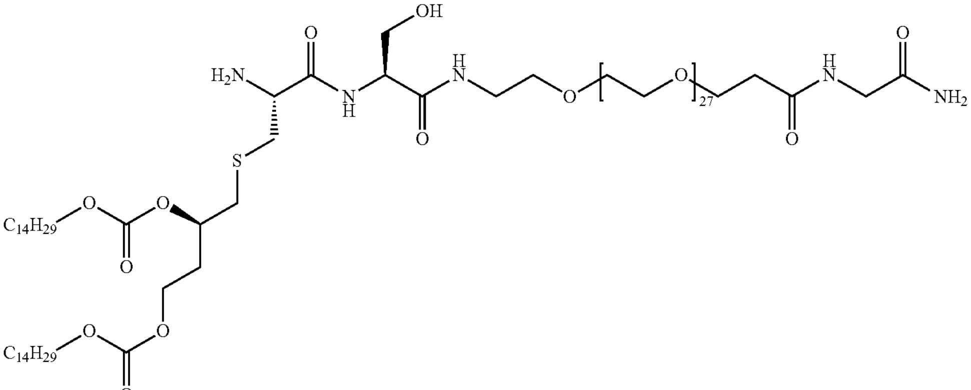 | Compound 20 |

-continued
| Compound Structure | Compound name |
|---|---|
| 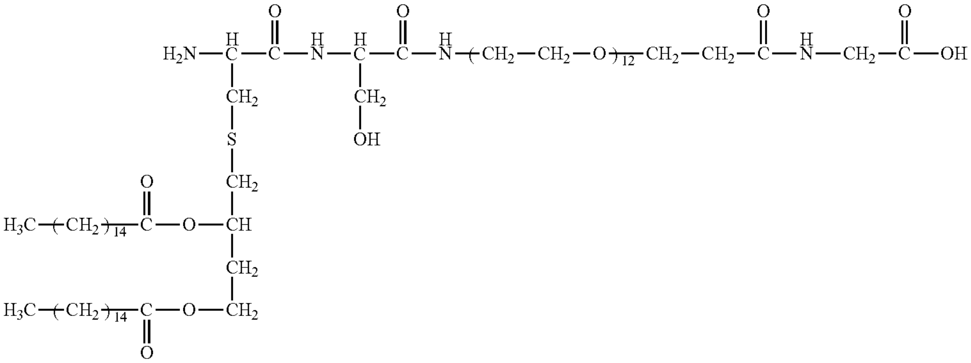 | Compound 21 |
| 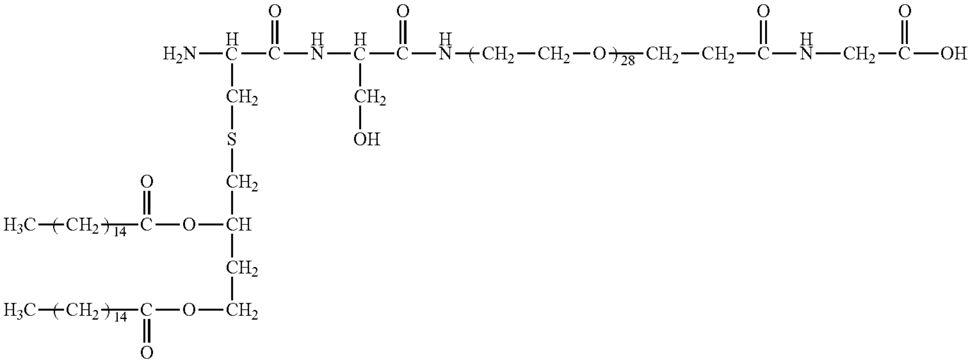 | Compound 22 |
| 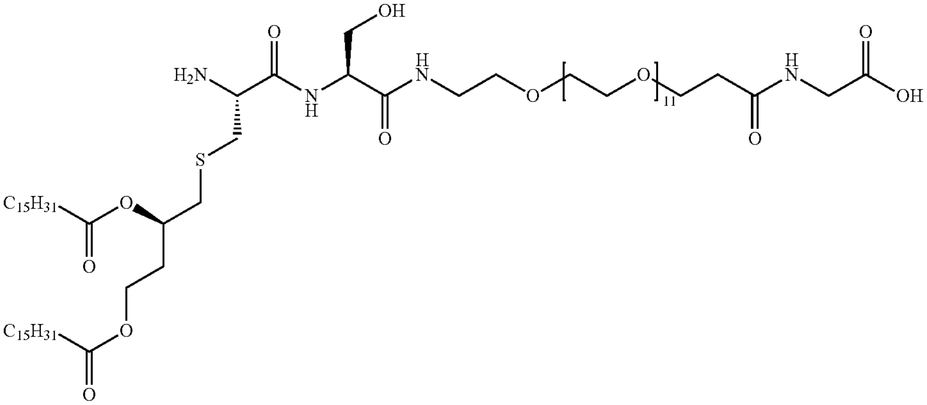 | Compound 23 |
| 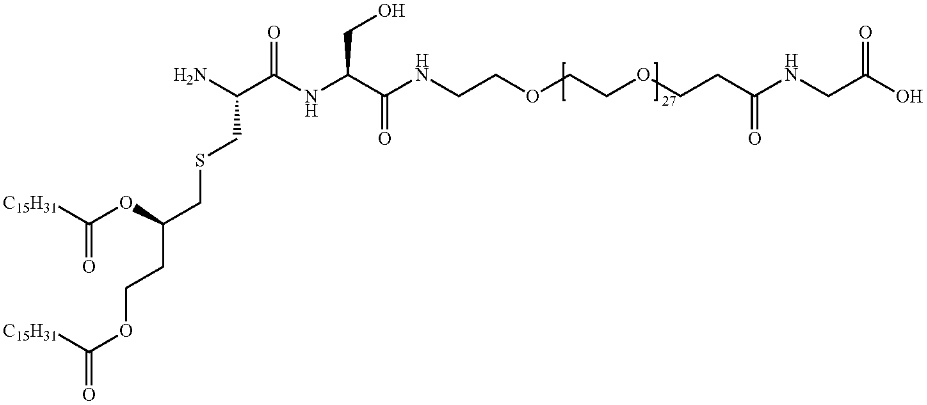 | Compound 24 |

-continued
| Compound Structure | Compound name |
|---|---|
| 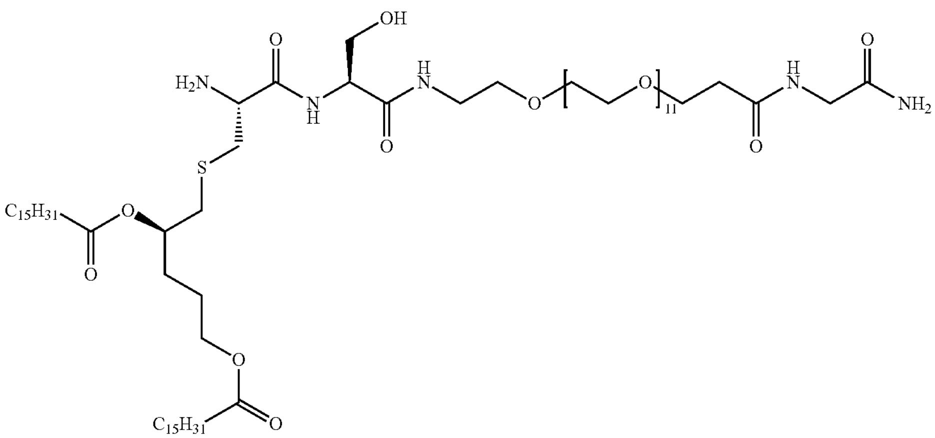 | Compound 25 |
| 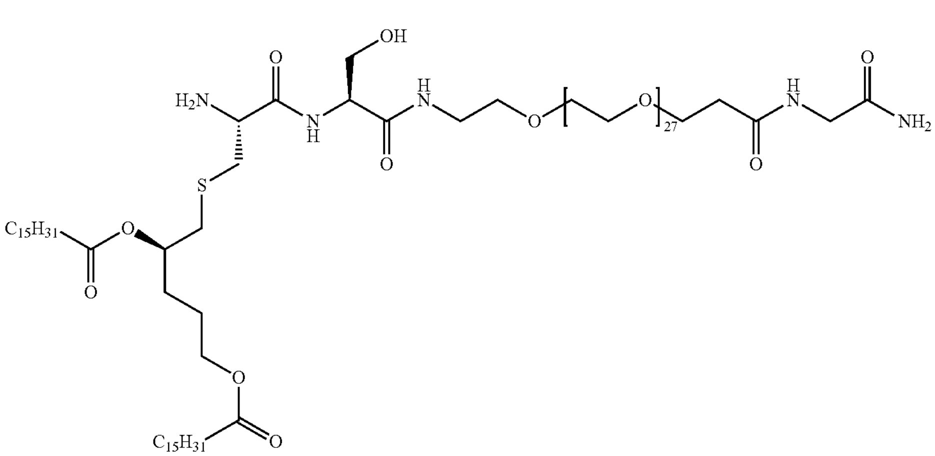 | Compound 26 |
| 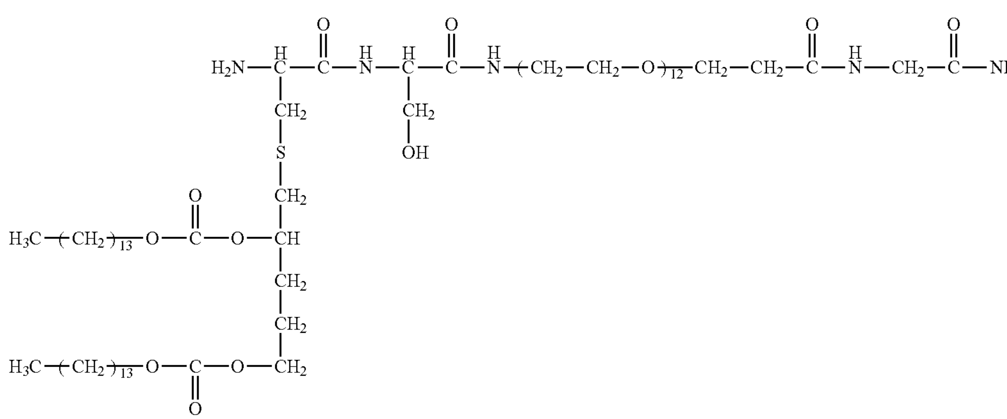 | Compound 27 |

-continued
| Compound Structure | Compound name |
| --- | --- |
| 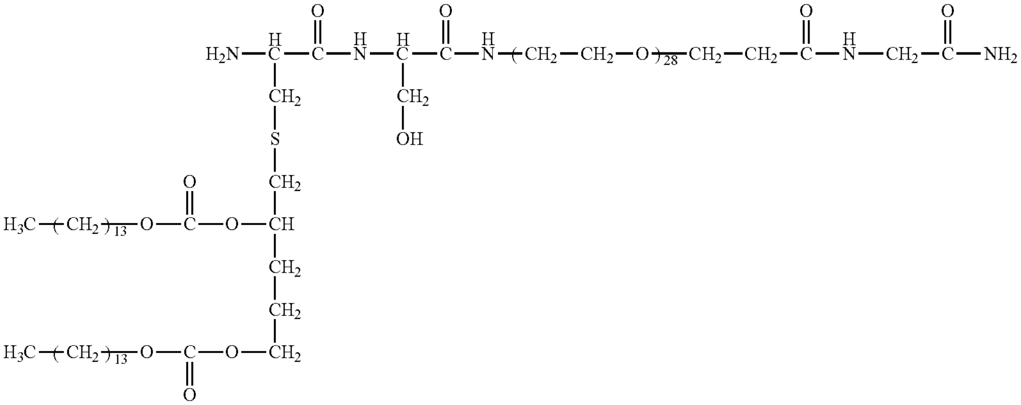 | Compound 28 |
| 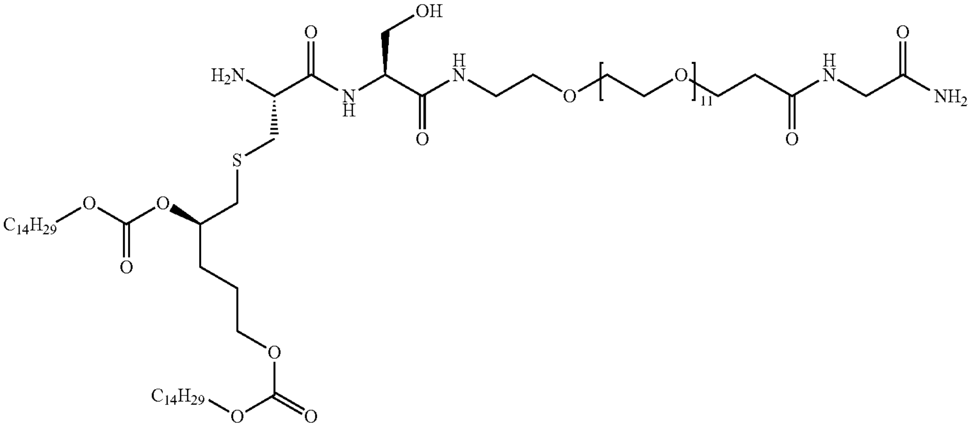 | Compound 29 |
| 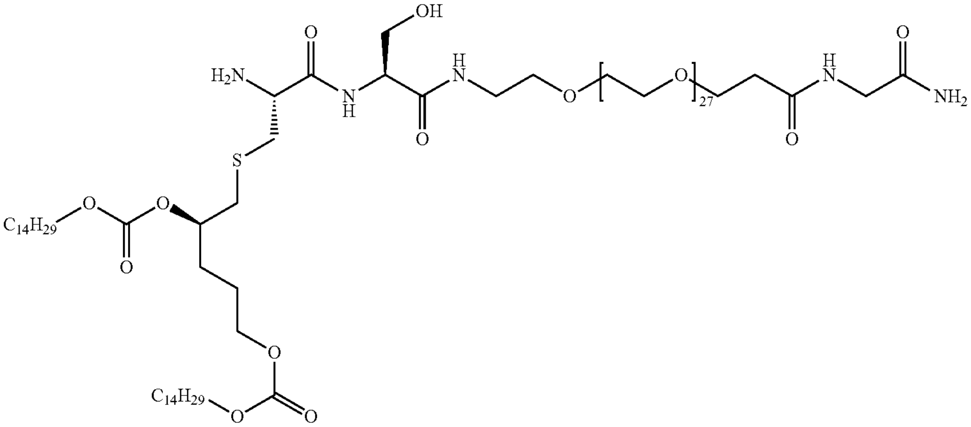 | Compound 30 |

-continued
| Compound Structure | Compound name |
| --- | --- |
| 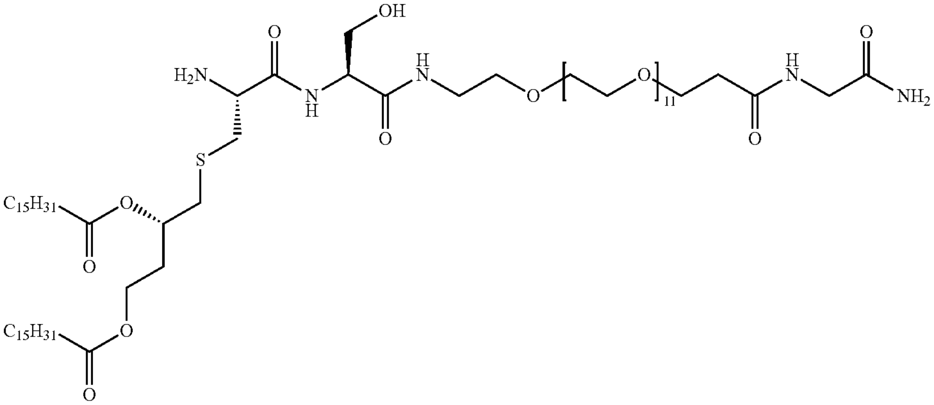 | Compound 31 |
| 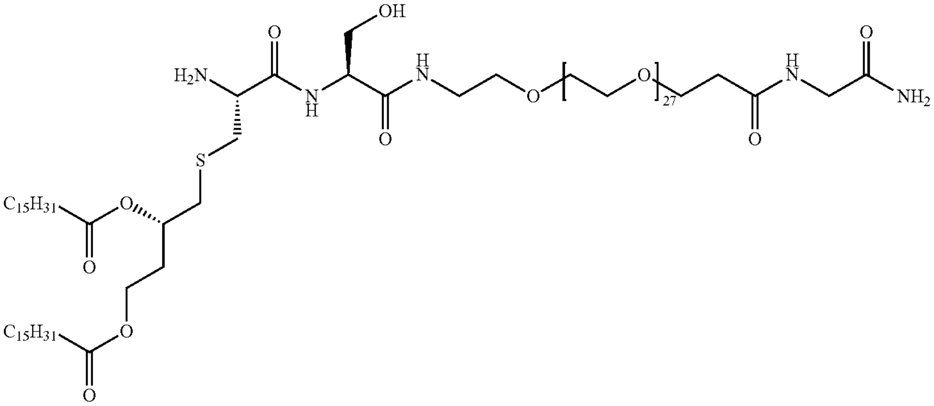 | Compound 32 |
| 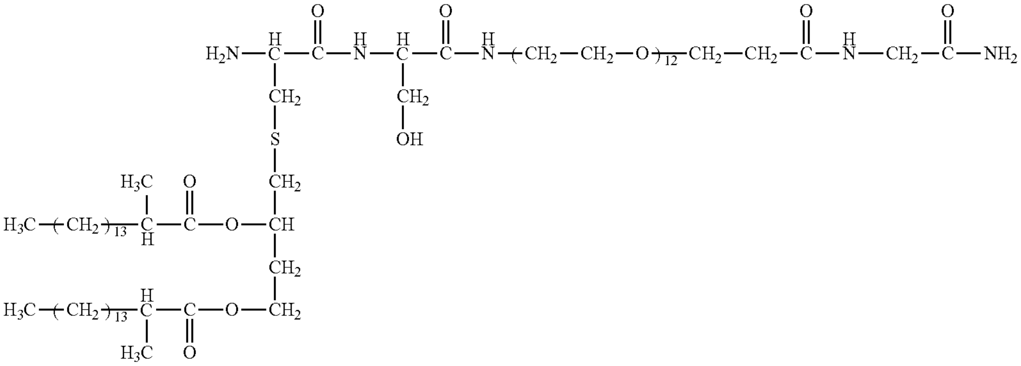 | Compound 33 |
| 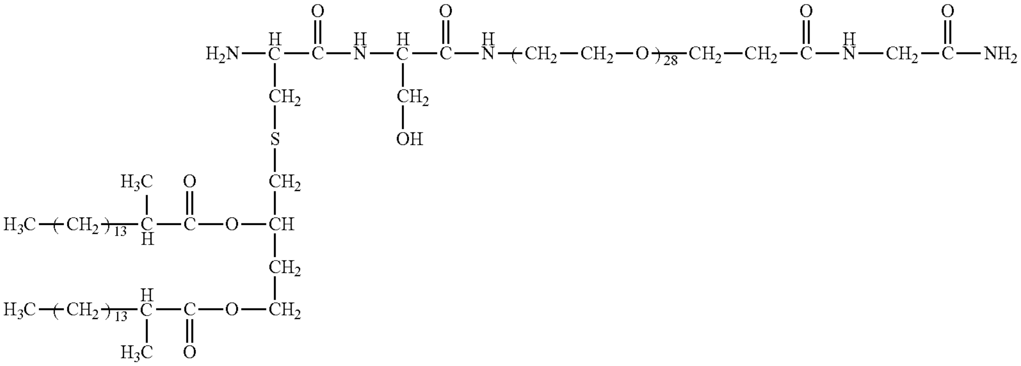 | Compound 34 |

-continued

| Compound Structure | Compound name |
| --- | --- |
| 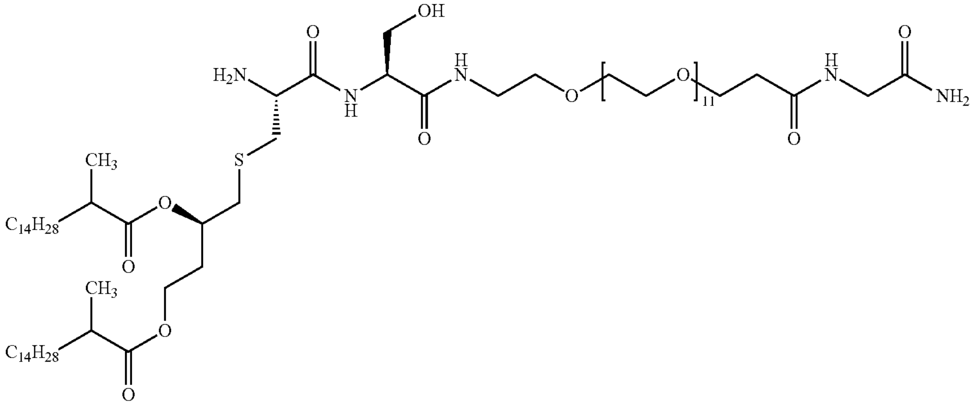 | Compound 35 |
| 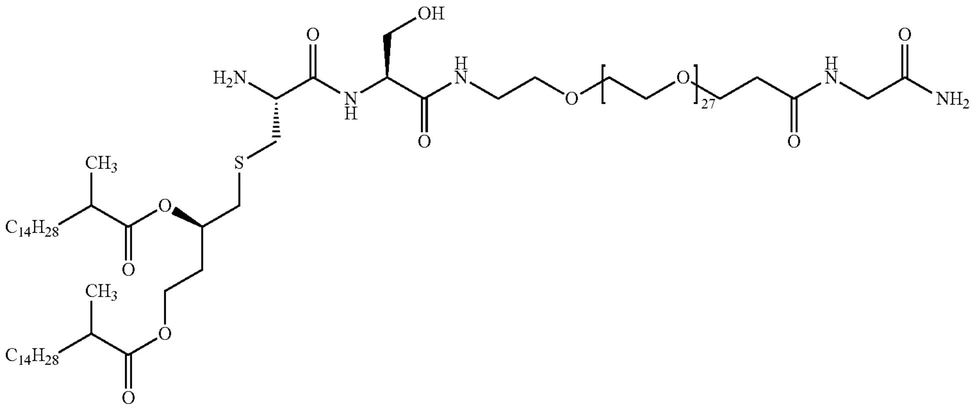 | Compound 36 |

It will be understood that the invention disclosed and defined in this specification extends to all alternative combinations of two or more of the individual features mentioned or evident from the text or drawings. All of these different combinations constitute various alternative aspects of the invention.

Example 1—Synthesis of Compounds

Example 1.1—Synthesis a Using Fmoc Solid Phase Chemistry

Compounds of the invention, including those according to Formula (I), may be provided by coupling a compound of the formula A-1:

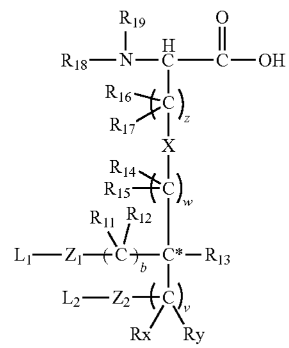

wherein $L_1$, $L_2$, $Z_1$, $Z_2$, v, b, w, z, $R_x$, $R_y$, $R_{11}$, $R_{12}$, $R_{13}$, $R_{14}$, $R_{15}$, $R_{16}$, $R_{17}$, $R_{18}$ and X have the meanings as defined for any compound of the invention defined herein and $R_{16}$ is an amino protecting group with a compound of formula YB-1:

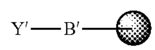

wherein

Y' is

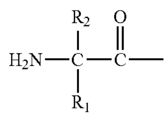

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C$(═O)$NH_2$, —$CH_2CH_2C$(═O)OH and —$CH_2CH_2C$(═O)$OR_8$, wherein any one of the alkyl hydrogens can be replaced with a halogen;

$R_8$ is selected from the group consisting of H and a straight or branched $C_1$-$C_6$ alkyl;

B' is a Polyethylene Glycol (PEG); and

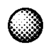

is a solid support resin.

In some embodiments, B' comprises a substituted PEG of Formula B-I. In these embodiments, the following sequence of solid phase reactions may be employed:

a) Optionally coupling 1 to 10 alpha amino acids or compounds derived from a natural alpha amino acid, that constitutes L, to a solid phase resin using Fmoc chemistry b) Coupling PG-NH—$(CH_2)_p$—O—$(CH_2CH_2O)_n$—$(CH_2)_m$—COOH to a solid phase resin or substituted resin if L is present, wherein PG represents an amino protecting group compatible with Fmoc chemistry;

c) Removing PG;

d) Coupling PG-NH—$CR_{13}R_{14}$—COOH, wherein PG' represents an amino protecting group compatible with Fmoc chemistry;

e) Removing PG';

f) Coupling an acid of the formula (A-I);

g) Optionally removing $R_{19}$ and optionally acylating and/or alkylating to introduce $R_{18}$ and/or $R_{19}$; and h) Removing the compound from the solid phase support In some embodiments, B' comprises a substituted PEG according to formula (B-II) and the following sequence of solid phase reactions may be employed:

a) Optionally coupling 1 to 10 alpha amino acids or compounds derived from a natural alpha amino acid, that constitute L, to a solid phase resin using Fmoc chemistry b) Coupling PG-NH—$(CH_2)_t$—O—$(CH_2CH_2O)_k$—$(CH_2)_h$—COOH to a solid phase resin or substituted resin if L is present, wherein PG represents an amino protecting group compatible with Fmoc chemistry;

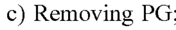

c) Removing PG;

d) Coupling PG'-NH—$(CH_2)_p$—O—$(CH_2CH_2O)_n$—$(CH_2)_m$—COOH, wherein PG' represents an amino protecting group compatible with Fmoc chemistry;

e) Removing PG';

f) Coupling PG"-NH—$CR_{13}R_{14}$—COOH, wherein PG" represents an amino protecting group compatible with Fmoc chemistry;

g) Removing PG";

h) Coupling an acid of the formula (A-1);

i) Optionally removing $R_{19}$ and optionally acylating and/or alkylating to incorporate $R_{18}$ and/or $R_{19}$; and j) Removing the compound from the solid phase resin.

It will be appreciated that the exact sequence of events can be varied from that outlined, and additional steps added where necessary and synthetically expedient, for example oxidation of the cysteine sulfur to the sulfoxide.

Example 1.2—Synthesis of Intermediate for Use in the Solid Phase Coupling A

Some embodiments of the intermediate acid of formula A-II:

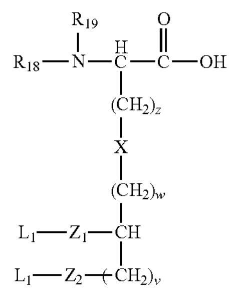

wherein $L_1$, $L_2$, X, v, w and $R_{15}$ are as defined for the compound of formula A-1 above, $Z_1$ and $Z_2$ are independently selected from —NHC(O)—, —C(O)NH—, —OC(O)—, —C(O)O—, —NHC(O)O— and —OC(O)O—;

may be prepared by the synthesis shown in Scheme 1.

Scheme 1 describes the synthesis of embodiments of the compound of formula A-II, wherein X is S, $L_1$-$Z_1$ are —OC(O)E-$C_gH_{(g'+2)}$, wherein E is —O— or —NH— and g' is 11, 12, 13, 14, 15, 16, 17, 18 or 19;

$L_2$-$Z_2$ are —OC(O)E-$C_gH_{(g'+2)}$, wherein E is —O— or —NH— and g' is 11, 12, 13, 14, 15, 16, 17, 18 or 19; and $R_{19}$ is PG3, which is an amino protecting group.

Scheme 1

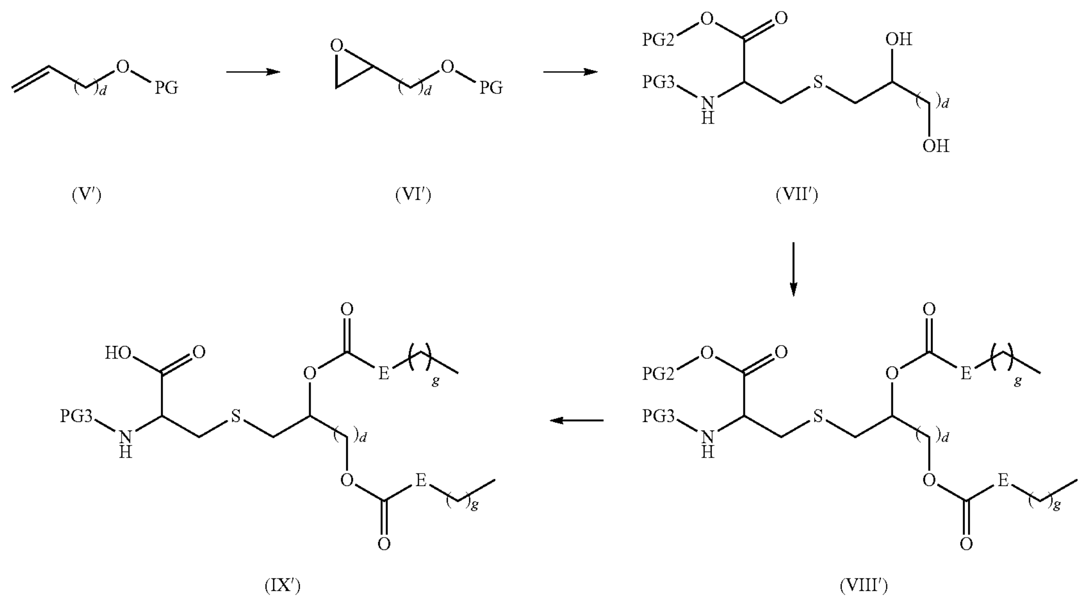

(V') (VI') (VII') (VIII') (IX')

Reaction of protected alkene alcohols of the formula (V'), where PG is a suitable protecting group, for example a silyl group such as TBDMS, forms an epoxide of the formula (VI'). It will be appreciated that the epoxide formation may be carried out to give the product racemically or to give enantioenriched material. If a racemic or scalemic mixture of enantiomers is produced preparative chiral chromatography is employed to separate the enantiomers if required.

Epoxides of the formula (VI') are reacted with suitably protected cystine analogues, for example tert-butyl N-(((9H-fluoren-9-yl)methoxy)carbonyl)-S—(((R)-2-((((9H-fluoren-9-yl)methoxy)carbonyl)amino)-3-(tert-butoxy)-3-oxopropyl)thio)-D-cysteinate, where PG2 is a tert-butyl ester and PG3 is Fmoc, under reducing conditions to give alcohols of the formula (VII'). It will be appreciated that alcohols of the formula (VII') can be comprised of more than one stereoisomer and where stereoisomers are present these can be separated by chiral preparative chromatography as required.

Alcohols of the formula (VII') can be acylated to give carbonyl containing adducts of the formula (VIII') using suitable reagents. Where esters are required, acid chlorides can be reacted in the presence of suitable bases and solvents; where carbamates are required isocyanates can be reacted in the presence of suitable bases and solvents and where carbonates are required chloroformates can be reacted in the presence of suitable bases and solvents. Carbonyl containing adducts of the formula (VIII') can then be deprotected to reveal carboxylic acids of the formula (IX') using suitable reagents, for example where PG2 is tert-butyl, trifluoroacetic acid can be used to preferentially remove the tert-butyl group.

Acids of the formula (IX') can then be used as reagents in solid phase synthesis to add groups of formula Y and B.

Example 1.3—Synthesis B Using Fmoc Solid Phase Chemistry

Compounds of the invention, including those according to Formula (I), wherein z is 1, w is 1 and b is 0, may be provided by preparing a resin bound peptide of the following formula:

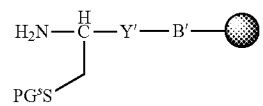

wherein

Y' is

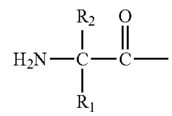

wherein R, and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_8$ is selected from the group consisting of H and a straight or branched $C_1$-$C_6$ alkyl;

B' is a Polyethylene Glycol (PEG);

$PG^s$ is H or a sulphur protecting group, such as tert-butyl; and

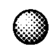

is a solid support resin.

Following optional sulphur deprotection, this resin bound peptide may be reacted with a 1,2-epoxy-alkanol of the following formula:

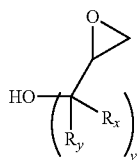

wherein $R_x$, $R_y$ and v have the meanings given for Formula (I)

to provide an alkylated thiol of formula S-1:

S-1

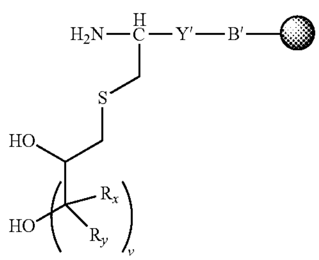

wherein Y' and B' have the meaning given above, and v has the meaning given for the compound of formula (I), or a sulfone or sulfoxide thereof.

The diol moieties of resin bound compound S-1 may be further reacted to provide a compound of the invention, for example, by diol functionalisation with palmitic groups or lauryl carbamate groups, etc.

Example 1.4—Synthesis and Characterisation of Compounds 3, 4, 15 and 16

Synthesis of compounds 3 and 4. The synthesis of compounds 3 and 4 is depicted below in Scheme 2.

Fmoc-Gly was added as the first amino acid to the solid support, followed by coupling of Fmoc-$NHCH_2CH_2O$—$(PEG)_{11}$-$CH_2CH_2COOH$ or Fmoc-$NHCH_2CH_2O$—$(PEG)_{27}$-$CH_2CH_2COOH$ in 2-fold molar excess in presence of a two-fold excess of Hexafluorophosphate Benzotriazole Tetramethyl Uronium (HBTU), Hydroxybenzotriazole (HOBT) and 4-fold excess of diisopropylethylamine (DIPEA) in 2 ml of dimethylformamide (DMF) for 2 hrs. Fmoc-Ser(tBu)-OH is then coupled to provide intermediate A2, followed by the coupling of Boc-Cys(StBu) A1. The thiol-tert-butyl group on the cysteine residue was removed by incubating the peptide resin in 0.5M of dithiothreitol for 1 hr in DMF at RT. To 250 mg of Boc-Cys-Ser(tBu) $CH_2CH_2O$-$(PEG)_{11}$-$CH_2CH_2C(O)$Gly resin or Boc-Cys-Ser (tBu)$CH_2CH_2O$-$(PEG)_{27}$—$CH_2CH_2C(O)$Gly resin (0.25 mmole/g, 0.25 g=0.0625 mmole) saturated in DMF was added 250 µl of R—(+)-1,2-epoxy-butan-4-ol [(R)-2-(oxiran-2-yl)ethan-1-ol] ($M_w$=88.11, d=1.1, 250 µl=3.125 mmol equivalent to a 50 fold excess over the free sulfhydryl group present on the peptide resin) and 25 µl of diisopropylethylamine (DIPEA, $M_w$=129.2, d=0.74, 25 µl=0.14 mmol). The reaction mixture was left in a water bath at 50° C. for 2 hrs and then thoroughly washed with DMF to provide intermediate A3.

Palmitic acid (320 mg, 1.25 mmol), DIPCDI (225 uL, 1.5 mmol) and 4-dimethylaminopyridine (DMAP; 15.25 mg, 0.125 mmol) were dissolved in 2 mL of dichloromethane (DCM) then added to the resin-bound BOC-Dhc-peptide resin A3 (0.0625 mmol, 0.25 g) and shaken for 16 h at room temperature. The supernatant was removed by filtration and the solid support thoroughly washed with DCM and dimethylformamide (DMF) to remove any residue of urea before being subjected to the cleavage process as described below.

The solid support bearing the assembled lipopeptide was exposed to reagent B (93% TFA, 5% water and 2% triisopropylsilane) for 2 hours. To isolate the product, most of the TFA was removed and the residue is then dissolved in 50% acetonitrile and purified immediately using the purification protocol described below or the material was freeze-dried and stored for later purification.

Scheme 2. Synthesis of compound 3 (x = 11) and compound 4 (x = 27)

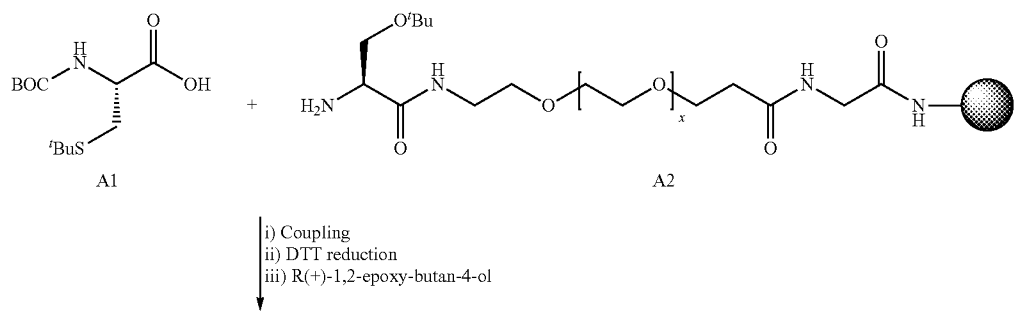

-continued

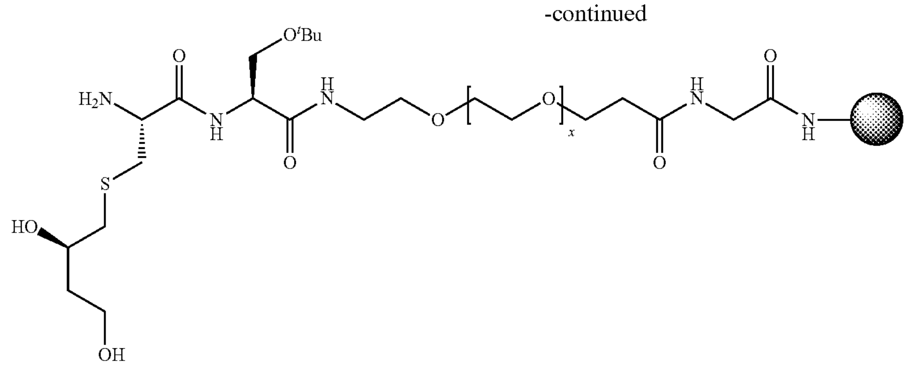

A3 i) Palmitic acid/DMAP/DIC
ii) Cleavage

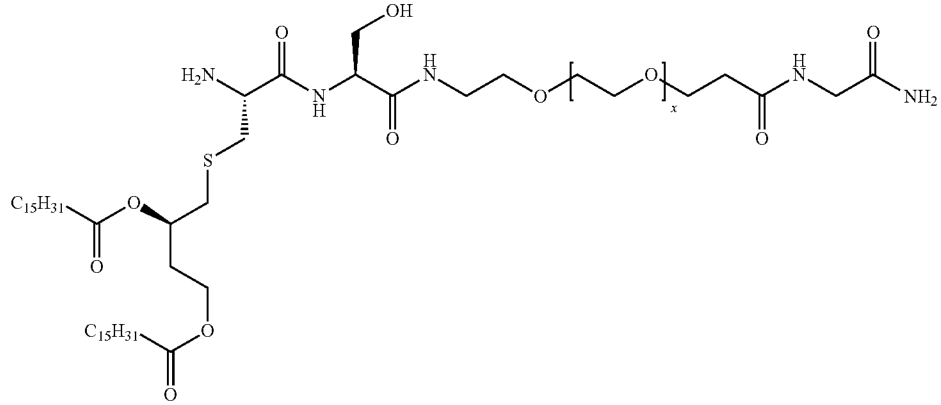

3: x = 11
4: x = 27

Synthesis of Compound 15 and Compound 16. The synthesis of compounds 15 and 16 was carried out as depicted in Scheme 3. Intermediate $A_3$ was prepared as described for compounds 3 and 4 above.

Then, to 250 mg of the peptide resin washed with toluene following glycidolation, were added 100 μl of ethylmethylsulfide ($M_w$=76.16, d=0.842, 100 μl=1.10 mmol) followed by 105 μl of tetradecyl isocyanate (MW=239, d=0.869, 105 μl=0.38 mmol, i.e. 3-fold excess over each of the hydroxyl groups present on the solid support) and finally 210 μl of dibutyltin dilaurate ($M_w$=631.6, d=1.053, 210 μl=0.35 mmol). The reaction mixture was sparged with nitrogen gas for approximately 5 min and mixed (Intelli-Mixer, RM-2, program F26 used) overnight at room temperature. The reaction mixture was transferred to a 50 ml tube and chloroform added to 50 ml. Following sonication for approximately 5 mins the white precipitate, formed during the reaction, dissolved. The solid support was washed with DMF and acetonitrile and the final product obtained following cleavage (as above) from the support was purified by HPLC.

Scheme 3. Synthesis of compounds 15 (x = 11) and 16 (x = 27)

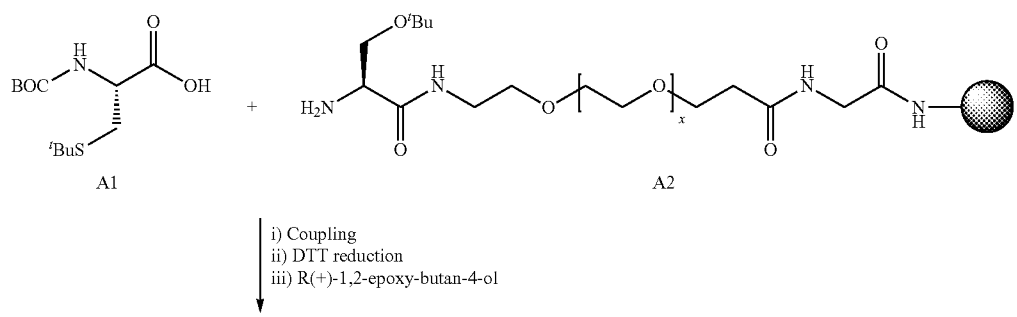

A1 A2

-continued

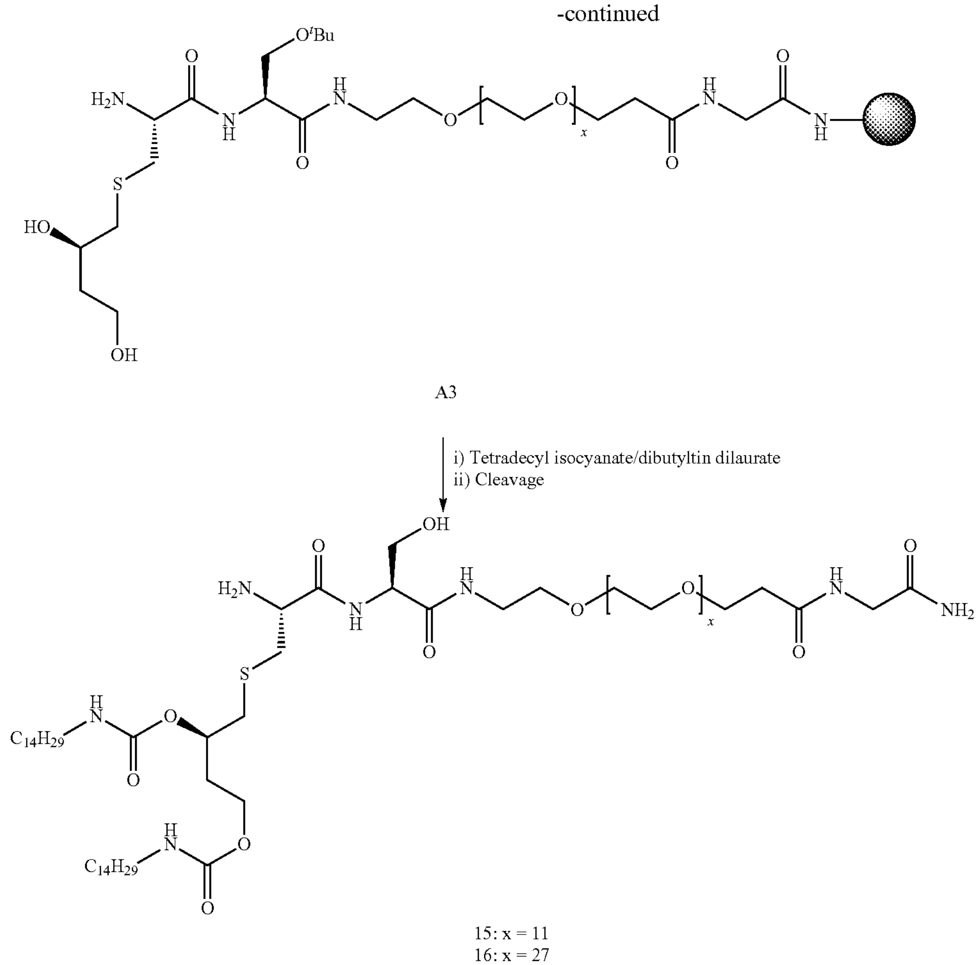

A3

15: x = 11
16: x = 27

Synthesis of compound 20. Compound 20 was synthesized by standard Fmoc Solid Phase Peptide Synthesis, starting with Fmoc-RINK MBHA PS Resin. Removal of the Fmoc group after each coupling was achieved using 20% piperidine in DMF. Couplings of Fmoc-Gly-OH (2-fold excess), Fmoc-NH-PEG$_{28}$-CH$_2$CH$_2$COOH (1.4-fold excess), Fmoc-Ser(tBu)-OH (2-fold excess), and N-(Boc)-S—((R)-2,3-dihydroxybutyl)-L-cysteine (1.5-fold excess) were performed in DMF using equivalent excess of ethyl cyano(hydroxyimino)acetate (Oxyma Pure) and diisopropylcarbodiimide (DIC) as coupling agents. Myristyl Chloroformate coupling was performed using Myristyl Chloroformate (12 eq. vs. moles resin), DIEA (24 eq. vs. moles resin) in dry DCM for 18 hours at room temperature. This coupling was repeated three times ("recoupling"). The first recoupling was done using Myristyl Chloroformate (12 eq. vs. moles resin), NMM (24 eq. vs. moles resin) in dry DCM/THF (85/15) for 18 hours at room temperature. The second recoupling was done using Myristyl Chloroformate (6 eq. vs. moles resin), NMM (12 eq. vs. moles resin) in dry DCM/THF (85/15) for 41 hours at room temperature. Finally the third recoupling was performed using Myristyl Chloroformate (6 eq. vs. moles resin), NMM (12 eq. vs. moles resin) in dry DCM/THF/Toluene (85/15/5) for 21.5 hours at room temperature.

Cleavage of the peptide from the resin, removal of N-terminal Boc group, and serine side-chain deprotection were achieved by exposure of the resin to a solution of 93% trifluoroacetic acid (TFA), 5% $H_2O$, 3% triisopropylsilane (TIPS) for 1.5 hours. Following the cleavage reaction, the mixture was evaporated and the resulting residue was re-dissolved in 30% acetonitrile/water and lyophilized.

Synthesis of compound 24. Compound 24 was synthesized by standard Fmoc Solid Phase Peptide Synthesis, starting with Chlorotrityl Chloride Resin with an initial substitution of 1.6 meq/g. The first amino acid, Fmoc-Gly-OH, was loaded on the resin first, using a 0.5-fold molar excess of Fmoc-Gly-OH and DIEA (1.5-fold excess), followed by capping with DMF/MeOH/DIEA (80/10/10), and Fmoc deprotection, to obtain the dry loaded H-Gly-CT Resin with a final substitution of 0.67 meq/g. Removal of the Fmoc group after each coupling was achieved using 20% Piperidine in DMF. Coupling of Fmoc-NH-PEG$_{23}$-CH$_2$CH$_2$COOH (1.4 eq.) was performed using (7-Azabenzotriazol-1-yloxy)trispyrrolidinophosphonium hexafluorophosphate (PyAOp; 1.4 eq.), diisopropylethylamine (DIEA; 3.2 eq.) in DMF, whereas couplings of Fmoc-Ser(tBu)-OH (2 eq), and N-(Boc)-S—((R)-2,4-dihydroxybutyl)-L-cysteine (1.5 eq.) were performed in DMF using equivalent excess of Oxyma Pure and DIC as coupling agents. Palmitic Acid coupling was performed using palmitic acid (20 eq. vs. moles resin), DIC (20 eq.), DMAP (2 eq.) in DCM/THF (85/15) (v/v) for 24 hours at room temperature.

Cleavage of the peptide from the resin, removal of N-terminal Boc group, and serine side-chain deprotection were achieved by exposure of the resin to a solution of 93% TFA, 5% H2O, 3% TIPS for 1.5 hours. Following the cleavage reaction, the mixture was evaporated and the resulting residue was re-dissolved in 30% Acetonitrile/Water and lyophilized.

Synthesis of compound 36. Compound 36 was synthesized by standard Fmoc Solid Phase Peptide Synthesis, starting with Fmoc-RINK MBHA PS Resin. Removal of the Fmoc group after each coupling was achieved using 20% Piperidine in DMF. Couplings of Fmoc-Gly-OH (2-fold excess), Fmoc-NH-PEG28-$CH_2CH_2COOH$ (1.4-fold excess), Fmoc-Ser(tBu)-OH (2-fold excess), and N-(Boc)-S—((R)-2,3-dihydroxybutyl)-L-cysteine (1.5-fold excess) were performed in DMF using equivalent excess of Oxyma Pure and DIC as coupling agents. 2-Methyl-Palmitic Acid coupling was performed using 2-Methyl-Palmitic Acid (20 eq. vs. moles resin), DIC (20 eq.), DMAP (2 eq.) in DCM/THF (85/15) (v/v) for −20 hours at room temperature.

Cleavage of the peptide from the resin, removal of N-terminal Boc group, and serine side-chain deprotection were achieved by exposure of the resin to a solution of 93% TFA, 5% $H_2O$, 3% TIPS for 1.5 hours. Following the cleavage reaction, the mixture was evaporated and the resulting residue was re-dissolved in 30% Acetonitrile/Water and lyophilized.

Purification and Characterisation

Purification and characterisation: Following cleavage from the solid support, each of the analogs were purified by reversed-phase HPLC according to either protocol A or B described below.

Protocol A: Reversed phase HPLC was conducted using an Agilent Zorbax 300SB-$C_3$, Sum column (9.4 mm×250 mm; Agilent Technology, Australia) installed in an Agilent HPLC 1260 Infinity system (Agilent Technologies, Santa Clara, California, USA) with the chromatogram developed using Buffer A (0.1% trifluoroacetic acid in water) and buffer B (0.1% trifluoroacetic acid in acetonitrile).

Protocol B: Reverse phase chromatography was conducted using a Novasep Axial Compression Column (5-cm diameter) loaded with cyano media (Daisogel SP-120-CN-P), with a gradient of Acetonitrile in [0.1% TFA/Water]. Following intermediate lyophilization, ion-exchange was performed on Dowex ion-exchange resin in order to obtain the peptide as the acetate salt.

Compounds 3, 4, 15 and 16 prepared as above were purified by protocol A and compounds 20, 24 and 36 prepared as above were purified by protocol B.

Identification and purity determination of the target materials were carried out using an in-line HPLC-MS system using the following conditions:

Conditions A: HPLC column: Agilent Zorbax 300-SB C3 (150×0.5 mm; 5 μm) with the following gradient conditions: 0-5 min, 20% B: 5-32 min, 20% B-100% B: 32-40 min, 100% B-20% B. The flow rate was 20 μl/min. LC-MS: Agilent 1100 series capillary LC system in-line with an Agilent 1100 series LC/MSD ion-trap mass spectrometer. The mass spectrometer was operated with electrospray ionisation configured in the positive ion mode. Data analysis software from Agilent Technologies was used to de-convolute the charged ion series for identification of the peptide material and the material then characterised by LC-MS.

Conditions B: analytical reverse phase HPLC with a cyano column (Daiso Fine Chem, SP-120-3-CN-P, 150×4.6 mm, 3 μm, 120 Å). The peptide was also analyzed by ESI LC-MS in Positive Ion Mode, using a Finnigan LCQ Deca XPMax.

Compounds 3, 4, 15 and 16 prepared and purified as described above, were each found to be greater than 95% pure according to conditions A.

Compounds 20, 24 and 36 prepared and purified as described above, were found to be greater than 95% pure according to conditions B.

Experimental masses (m/z) accorded with calculated molecular weights for each compound.

Peptide Quantitation

Quantitation of compounds 3, 4, 15 and 16 was carried out by in vacuo hydrolysis at 110° C. of samples in sealed glass vials in the presence of 6N HCl containing 0.1% phenol. Derivatisation of amino acids was then carried out using Waters AccQTag reagents according to the manufacturer's instructions followed by analysis on a Waters Acquity UPLC System (Waters Millipore) using an AccQTag ultra column (2.1 mm×100 mm; Waters Millipore). Quantitation of other compounds may be achieved by a similar protocol.

1.5—Synthesis of Sulfone and Sulfoxide Analoques of Compounds 15 and 16

Sulfone and sulfoxide derivatives of compounds 15 and 16 may be accessed by a similar synthetic routes as described above, with the omission of ethylmethylsulfide scavenger, and optional omission of nitrogen sparging, from the carbamate formation step. This reaction may yield a mixture of thiol, sulfone and sulfoxide derivatives, which may be separated and purified by HPLC.

Alternatively, sulfone or sulfoxide derivatives may be prepared by oxidation of the corresponding sulfide with an oxidant such as meta-chloroperoxybenzoic acid (MCPBA) or tert-butyl hydroperoxide (t-BuOOH) under appropriate conditions.

Example 2—Activation of Human TLR2

The potency of the compounds as activators of human and mouse TLR-2s is tested in an in vitro assay. The assay assesses NF-kB activation in the HEKBlue-mTLR-2 cell line. These cells have been stably transfected with mouse TLR-2 and express TLR-1 and TLR-6 endogenously at sufficient levels to allow for fully-functional TLR-1/2 and TLR-2/6 activation.

Toll-Like Receptor 2 (TLR2) stimulation is tested by assessing NF-kB activation in the HEKBlue-hTLR2 cell line. These cells have been stably transfected with human TLR2 and express TLR1 and TLR6 endogenously at a level sufficient to allow for fully-functional TLR1/2 and TLR2/6 activation. The activity of the test articles are tested on human TLR2 as potential agonists. The test articles are evaluated at seven concentrations and compared to control ligands. These steps are performed in triplicate.

NF-kB reporter gene assay protocol: This assay was carried out as described previously (Jackson et al. 2004; Lau et al. 2006; Sandor et al. 2003; Zeng et al 2010). HEK293T cells were cultured in 96-well plates at $4\times10^4$ cells/well and transfected 24 h later with 100 ng of the NF-kB luciferase reporter gene [50 ng of TK-Renilla-luciferase expressing plasmid (Promega corporation, Madison, USA)] with or without 5 ng TLR2-expressing plasmid in the presence of 0.8 μl Fugene 6 (Roche Diagnostic). Compounds were added to the wells 24 h later at the concentrations indicated in the histograms. Cell lysates were prepared 5 h after stimulation using reporter lysis buffer (Promega Corporation, Madison, USA). Luciferase activities in the cell lysates were determined using a reagent kit (Promega Corporation, Madison, USA) and using a FLUOstar microplate reader (BMG Labtech, Ortenberg, Germany). The NF-kB-dependent firefly luciferase activity is normalised with NF-kB-independent renilla luciferase activity. The relative stimulation was calculated as the ratio of the stimulated to non-stimulated samples.

The results of this assay for compounds 3, 4, 15 and 16 are shown in FIG. 1. These data show that these compounds exhibit significant activity at TLR2.

Example 3—URT Virus Challenge

In these Examples, an upper respiratory tract (URT) influenza virus challenge model is utilised in mice, using a dose of infectious virus which replicates in the URT and then progress to the lungs. The URT model is used to determine which compounds can prevent replication and dissemination of influenza virus from the URT to the lungs.

Cytokine and chemokine profiles in the nasal turbinates, trachea, lungs and sera of animals following URT treatment with three doses or a single dose of the compounds are also measured.

The cytokine profiles of mice which were pre-treated with three doses of compounds of the invention followed by challenge with Udorn virus are also measured.

Experimental Animals

Groups of male or female C57BL/6 mice of similar age (e.g. about 6-8 week old) are used for all studies. After administration of saline, the compound or viral challenge, mice are monitored daily for weight changes, and behavioural or physical changes.

URT Administration of Compounds

Mice are anaesthetized by isoflurane inhalation and saline or various doses of the compounds, diluted in saline, are administered intranasally using a pipettor. For the multi-treatment experiments, mice receive 3 doses of the compounds of the invention every second day over a 5 day period.

Preparation of Influenza Virus

A/Udorn/307/72 (H3N2) influenza virus (ie. Udorn virus) is propagated in the allantoic cavity of 10 day-old embryonated hens' eggs. Eggs are inoculated with approximately $10^3$ pfu of virus in 0.1 ml of saline. After 2 days incubation at 35° C. the eggs are chilled at 4° C. and allantoic fluid harvested and clarified by centrifugation. Viral infectivity titre (pfu/mL) is determined by plaque assay as described below and aliquots of the allantoic fluid were stored at −80° C. until used.

URT Virus Challenge

Mice are anaesthetised with isofluorane and inoculated intranasally with 500 pfu of Udorn virus in 10 μl of saline, using a pipettor. On day 5 post-challenge, the nasal turbinates, trachea and lung are harvested to assess viral loads.

Extraction and Preparation of Nasal Turbinates, Trachea and Lung Homogenates

Mice are killed by $CO_2$ asphyxiation 24 hours post-treatment or 5 days post-influenza challenge. Nasal turbinates, trachea and lungs from each mouse are collected in 1.5 mL of RPMI-1640 medium with antibiotics (100 ug/mL penicillin, 180 ug/mL streptomycin and 24 ug/mL gentamicin) and kept on ice until processed. Tissues were homogenised using a tissue homogeniser and the resulting organ homogenates then centrifuged at 2,000 rpm for 5 min to remove cell debris. Supernatants are collected and stored at −80° C. for subsequent measurements.

Assessment of Viral Titres

Titres of infectious Udorn virus are determined by plaque assay on confluent monolayers of Madin Darby canine kidney (MDCK) cells. Six-well tissue culture plates were seeded with $1.2\times10^6$ MDCK cells per well in 3 ml of RP10 (RPMI-1640 medium supplemented with 10% (v/v) heat inactivated FCS, 260 ug/mL glutamine, 200 ug/mL sodium pyruvate and antibiotics). After overnight incubation at 37° C. in 5% $CO_2$ confluent monolayers were washed with RPMI. Test supernatants serially diluted in RPMI with antibiotics, are added to duplicate wells of monolayers. After incubation at 37° C. in 5% $CO_2$ for 45 min, monolayers are overlaid with 3 mL of agarose overlay medium containing 0.9% agarose and 2 ug/mL trypsin-TPCK treated in Leibovitz L15 medium pH6.8 with glutamine and antibiotics. Plates are incubated for 3 days at 37° C. in 5% $CO_2$ and virus-mediated cell lysis then counted as plaques on the cell layer. The total organ viral titres (plaque forming units, PFU) for individual animals are calculated.

Determination of Cytokine Levels in Nasal Turbinates, Trachea, Lungs and Sera

IFN-γ, IL-2, IL-4, TNF, IL-10, IL-6, KC, MCP-1, RANTES, IL-12/IL-23p40 and IL-17A present in nasal turbinates, trachea, lung homogenates and serum samples were measured using a BD Cytometric Bead Array (CBA) Flex Kit according to the manufacturer's instructions with the exception that a total of 0.15 μl of each capture bead suspension and 0.15 μl of each PE-detection reagent is used in each 50 μl sample. Samples were analysed using a Bection Dickinson FACSCanto II flow cytometer and the data analysed using FCAP Array multiplex software.

Statistical Analyses

A one-way analysis of variance (ANOVA) with Tukey comparison of all column tests may be used. A two-way ANOVA with Bonferroni's test may be used to compare the same treatment groups in the single and 3 repeat dose regimes. A p-value<0.0322 was considered statistically significant. Statistical analyses are performed using suitable software, such as GraphPad Prism, version 7.0.

Example 4—Assessing the Effect of Pre-Treatment with Different Doses of Compounds of the Invention on the Outcome of URT Challenge with Udorn Virus This experiment is performed to determine the anti-viral effect of URT pre-treatment with various doses of the compounds of the invention.

On day 0 mice (5 animals/group) receive either saline, 5 nmoles, 0.1 nmoles or 0.005 nmoles of compound of the invention, administered intranasally in 10 μl after being anaesthetized with isoflurane. On day 1 following administration with compound of the invention, mice are challenged intranasally with 500 pfu of Udorn virus in a volume of 10 μl after being anaesthetized with isoflurane. Mice are killed on day 5 and nasal turbinates trachea and lungs were removed, homogenised and frozen for subsequent analyses.

The experimental design is summarised in the schematic below

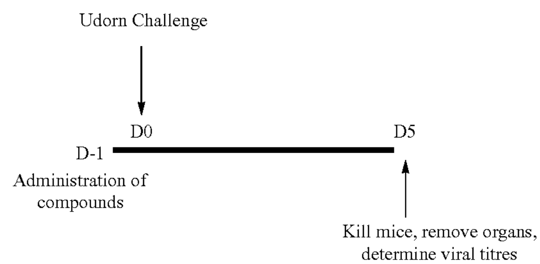

Example 5—TLR2 Activation by Various Compounds

Comparison of the abilities of various compounds to stimulate luciferase activity in an NF-κB cell-based reporter system is determined. HEK293T cells, transiently co-transfected with a human TLR2 plasmid and a luciferase-NF-κB plasmid reporter system, are exposed to various dilutions of each compound. Successful receptor binding and subsequent signal transduction events are determined by measuring the luminescence due to luciferase activity

Example 6—TLR Binding and Specificity

The compound of the invention is assessed for its ability to activate a range of other TLR pattern recognition receptors. These assessments are conducted using both human and mouse TLR panels. These assays detect a secreted embryonic alkaline phosphatase (SEAP) reporter under the control of a promoter which is inducible by NF-κB activation in HEK293 cells.

The secreted embryonic alkaline phosphatase (SEAP) reporter is under the control of a promoter inducible by the transcription factor NF-κB. This reporter gene allows the monitoring of signaling through the TLR, based on the activation of NF-κB. In a 96-well plate (200 μL total volume) containing the appropriate cells (50,000-75,000 cells/well), 20 μL of the test article or the positive control ligand is added to the wells. The media added to the wells is designed for the detection of NF-κB induced SEAP expression. After a 16-24 hr incubation the optical density (OD) is read at 650 nm on a Molecular Devices SpectraMax 340PC absorbance detector.

Control Ligands hTLR2: HKLM (heat-killed *Listeria monocytogenes*) at 1×108 cells/mL hTLR3: Poly(I:C) HMWat 1 μg/mL hTLR4: *E. coli* K12 LPS at 100 ng/mL hTLR5: *S. typhimurium* flagellin at 100 ng/mL hTLR7: CL307 at 1 μg/mL hTLR8: CL075 at 1 μg/mL hTLR9: CpG ODN2006 at 1 μg/mL.

Example 7—Stability I

Stability was assessed by tracking changes in the absolute peak area and % peak area of the compound of the invention subjected to the following conditions to the peak area and % peak area obtained from freshly prepared solutions of the relevant compound. The compound was formulated in each of the following formulations:

1. Phosphate buffered saline (PBS), pH 7.4. For example, the PBS buffer may comprise 8 g NaCl, 0.2 g KCl, 1.15 g disodium hydrogen phosphate and 0.2 g potassium dihydrogen phosphate in 1 litre of MilliQ water.
2. 0.9% w/w saline (pH 5.8). For example, saline solution may be prepared by dissolving sodium chloride (1.855 g) in 200 mL of Milli-Q water.

Stability for each formulation was assessed under the following conditions:

1. 25° C./60% relative humidity (ICH ambient)
2. 40° C./75% relative humidity (ICH accelerated)

Sample Preparation

Solutions of approximately 1 mg/mL of each compound (2 mL) were accurately prepared in the PBS and saline diluent systems. Actual concentrations are provided in Table 1.

TABLE 1

Test solution concentrations for stability monitoring

| Compound No. | Diluent | Conc'n (mg/mL) |
|---|---|---|
| 3 | Saline | 1.05 |
| | PBS | 1.10 |
| 4 | Saline | 1.10 |
| | PBS | 1.05 |
| 15 | Saline | 1.05 |
| | PBS | 1.03 |
| 16 | Saline | 0.990 |
| | PBS | 0.956 |

All compounds were heated to approximately 60° C. under hot running tap water for approximately 30 seconds, followed by vortex mixing for a further 30 seconds.

Each vial in Table 1 was further sub-aliquoted into 3 separate HPLC vials which were then placed into storage at 4-8° C. (fridge), 25° C./65% RH and 40° C./75% RH for 2 weeks. The vials were wrapped in aluminium foil to exclude light for the storage duration.

Equipment and Operational Parameters

A Shimadzu Nexera UHPLC with diode array detector was used to monitor peak area changes at t=0 and t=2 weeks.

A Shimadzu LCMS-8030 system was used to identify impurity and degradant peaks, and to verify the selectivity of the HPLC methods by checking across the main HPLC peak for possible co-eluting components.

UHPLC Parameters

Column—Phenomenex Kinetex Biphenyl, 50×2.1 mm, 2.6 μm, part no. 00B-4622-AN

Vials—Agilent clear glass, 2 mL with multi-injection septa, part no. 226-50512-00

Mobile Phase A—5 mM ammonium formate in Milli-Q water

Mobile Phase B—acetonitrile, Merck LC-MS grade

Needle Rinse Solution—1:1 water:methanol

Injection Volume: 1 μL

Column Temperature: 40° C.

Autosampler Temp: 20° C.

Total Flow Rate: 0.5 mL/min

Total Run Time: 10 min

UV-vis wavelength: 205 nm

TABLE 2

Gradient 1

| Time (min) | % A | % B |
|---|---|---|
| Init | 55 | 45 |
| 0.1 | 55 | 45 |
| 8.0 | 25 | 75 |
| 8.5 | 25 | 75 |
| 8.6 | 55 | 45 |

TABLE 3

Gradient 2

| Time (min) | % A | % B |
|---|---|---|
| Init | 55 | 45 |
| 0.1 | 55 | 45 |
| 8.0 | 25 | 65 |
| 8.5 | 25 | 65 |
| 8.6 | 55 | 45 |

LCMS Parameters

LC injection volume: 0.1 μL
Interface: ESI
Interface Temperature: 350° C.
Desolvation Temperature: 250° C.
Nebuliser Flow: 3 L/min
Heat Block: 400° C.
Drying Gas Flow: 15 L/min
Q3 scan mode: Positive
Start Time: 1 min
End Time: 8 min
Start m/z: 400
End m/z 2000 (INNA-011)
Scan Speed: 15000/sec Stability Results The samples of each of compounds 3, 4, 15 and 16 were analysed using either gradient 1 (compounds 3 and 4) or 2 (compounds 15 and 16). Results are shown in the following Tables 4 and 5, and in FIGS. 2 and 3. Results for storage at 40° C. are shown in Table 4 and results for storage at 25° C. are shown in Table 5.

Figure 3:
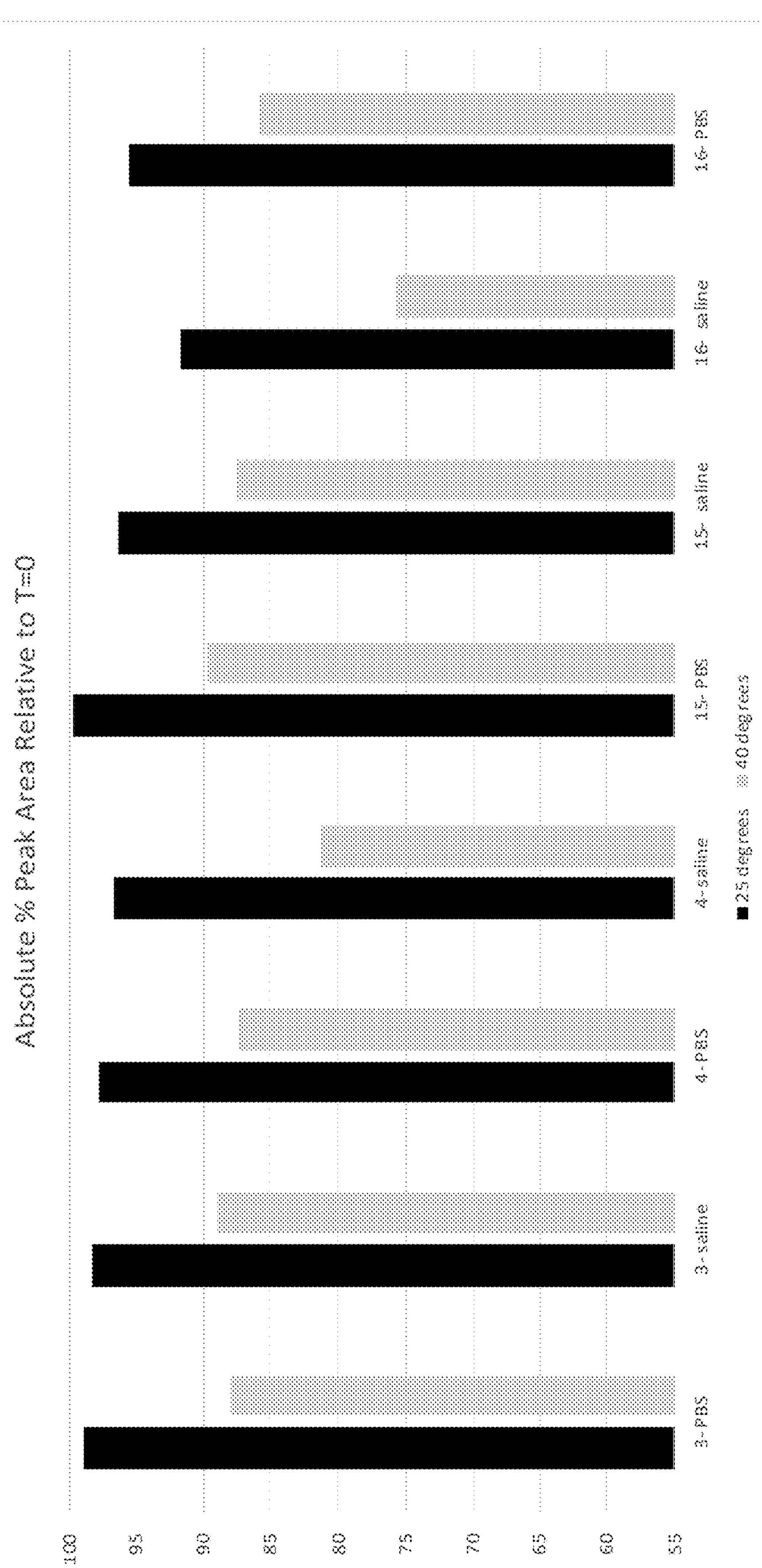
FIG. 3. Two-week (14 day) stability results as for FIG. 2 generated using the areas of the main peaks expressed as a percentage of the areas at time zero.

The stability results compare the peak area from the sample after subjecting to the relevant conditions relative to the percent peak area of the main HPLC peak at time zero, which was normalised to 100% to exclude the contribution of impurities to the total peak area. FIG. 2 shows the 2-week data calculated by this methodology. FIG. 3 shows a second data set generated using the areas of the main peaks expressed as a percentage of the areas at time zero.

TABLE 4

Stability of compounds 3, 4, 15 and 16 overtime in saline (0.9%) or PBS (pH 7.4) at 40° C.

| | % Peak Area ICH accelerated | | % Peak Area ICH accelerated | |
|---|---|---|---|---|
| Compound No. | Saline t = 0 | Saline t = 14 days | PBS t = 0 | PBS t = 14 |
| 3 | 98.7 | 96.5 | 98.5 | 95.4 |
| 4 | 97.2 | 94.0 | 97.3 | 95.0 |
| 15 | 97.8 | 91.6 | 96.5 | 90.4 |
| 16 | 95.5 | 87.0 | 95.8 | 90.4 |

TABLE 5

Stability of compounds 3, 4, 15 and 16 overtime in saline (0.9%) or PBS (pH 7.4) at 25° C.

| | % Peak Area ICH accelerated | | % Peak Area ICH accelerated | |
|---|---|---|---|---|
| Compound No. | Saline t = 0 | Saline t = 14 days | PBS t = 0 | PBS t = 14 |
| 3 | 98.7 | 98.6 | 98.5 | 98.5 |
| 4 | 97.2 | 96.8 | 97.3 | 97.3 |
| 15 | 97.8 | 97.9 | 96.5 | 96.0 |
| 16 | 95.5 | 94.1 | 95.8 | 95.7 |

Each of compounds 3, 4, 15 and 16 demonstrated substantial stability over the 2-week test period, suggesting that they may be suitably stable during storage and post-administration.

Example 8—Stability II

The relative stabilities of compounds 4, 16, 20, 24 and 36 and that of compound (8) of WO2019/119067 were evaluated under accelerated conditions (40° C./75% RH) for 9 days. Each compound was prepared at 1 mg/mL concentration in an aqueous formulation of 0.1% w/v EDTA/0.9% saline w/v buffered to pH 5.

The structure of compound (8) of WO2019/119067 is:

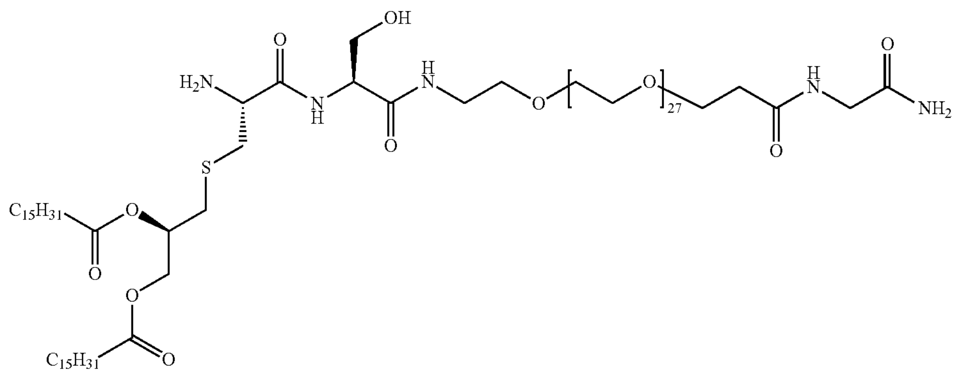

Stability was measured using reversed phase HPLC with a UV detector analytical wavelength of 205 nm. Peak areas of each compound at the 9 day time point were compared with areas at time zero. Compound stability at day 9 was calculated as a percentage of the time zero peak area data.

Compound stability was further assessed by comparison with a reference sample of the same compound. Reference samples were prepared at 1 mg/mL concentration in an aqueous formulation of 0.1% w/v EDTA/0.9% saline w/v buffered to pH 5 and frozen during the period of testing. Thawed samples were sonicated and measured by HPLC.

Data for each compound is summarised in Table 6.

TABLE 6

| Compound | area % recovery (Day 9) | % RSD (relative standard deviation) in reference | % RSD in samples | Estimated total % RSD (RMS) |
|---|---|---|---|---|
| Compound (8) of WO2019/119067 | 94.4 | 0.01 | 0.02 | 0.02 |
| 4 | 102.1 | 0.09 | 0.03 | 0.09 |
| 16 | 100.7 | 2.70 | 0.06 | 2.70 |
| 20 | 98.7 | 0.03 | 0.06 | 0.07 |
| 24 | 98.9 | 0.03 | 0.11 | 0.11 |
| 36 | 98.4 | 0.00 | 0.23 | 0.23 |

Each of compounds 4, 16, 20, 24 and 36 is shown to possess substantial stability over the 9 day test period. Each of these compounds also possesses superior stability under the accelerated conditions than the comparator compound.

Stability of compounds over further extended periods is assessed by prolonged exposure to the accelerated conditions, for example, for 28 days.

Example 9—Activation of Human TLR2 II

The potency of the compounds as activators of human TLR-2s is tested in an in vitro assay in HEK-BLUE-hTLR2 cells.

Culturing of HEK-BLUE-hTLR2 Cells

HEK-BLUE-hTLR2 cells are designed for studying the stimulation of human TLR2 (hTLR2) by monitoring the activation of NF-kB. HEK-BLUE-hTLR2 cells are obtained by co-transfection of the hTLR2 and SEAP (secreted embryonic alkaline phosphatase) reporter genes into HEK293 cells. Stimulation with a TLR2 ligand activates NF-kB which induces the production of SEAP.

HEK-BLUE-hTLR2 cells were purchased from InvivoGen (San Diego, CA, USA). Cells were grown in DMEM supplemented with 10% FCS, 100 U/ml penicillin, 100 ug/ml streptomycin and 2 mM L-glutamine, 100 μg/mL Normocin in the presence of selection antibiotic purchased from InvivoGen and passaged when 70% confluence was reached per manufacturer's recommendation. Cells were dislodged and resuspended in test media as suggested by manufacturer for testing.

Testing of Compounds i) A serial dilution of respective compounds were prepared in saline and added in 20 ml of each dilution in triplicates per well in a flat bottom 96-well plate and placed in the incubator while waiting for the cells.
ii) Remove HEK-BLUE-hTLR2 cells in a T-75 flask from incubator and discard the growth media.
iii) Gently rinse the cells with prewarmed 10 ml of PBS
iv) Add 5 ml of prewarmed PBS and place the cells in 37° C. for 2 mins and then detach the cells by gently pipetting up and down the PBS on the surface where the cells adhere.
v) Cells suspension at the density of 280,000 cells/ml is prepared in HEK-Blue™ Detection medium which is purchased from InvivoGen and prepared according to the manufacturer's instruction,
vi) Add immediately 180 ml of the cell suspension per well of the plate which contains the solution of the compounds. The plate is then returned to the incubator at 37° C. for 16 hr and was read at 620 nm by using an ELISA reader.

Figure 4:
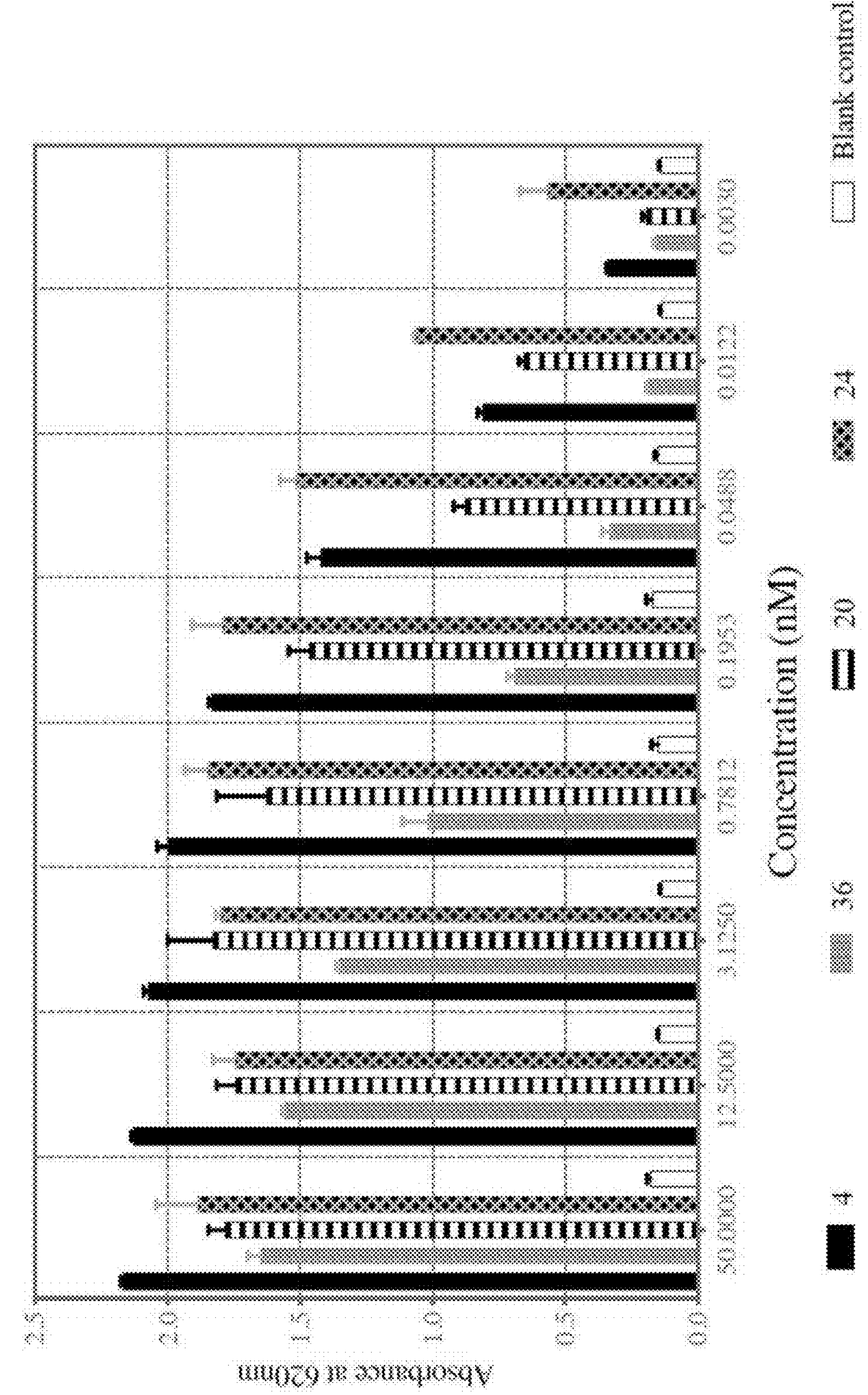
FIG. 4. TLR2 activity of compounds 4, 20, 24 and 36 from the NK-κB luciferase assay described in Example 9.

The results of this assay for compounds 4, 20, 24 and 36 are shown in FIG. 4. These data show that these compounds exhibit significant activity at TLR2.

The invention claimed is:

1. A compound of general formula:

A-Y—B wherein A is represented by:

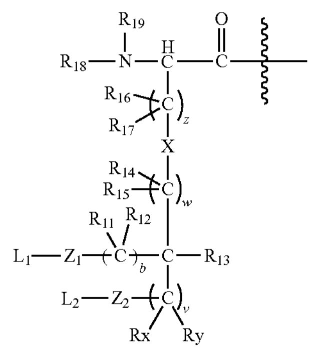

wherein:

b is 0;

w is 1;

v is an integer from 2 to 5;

z is 1;

X is —S—;

$Z_1$ and $Z_2$ are each independently selected from the group consisting of —O—, —NR—, —S—, S(═O), S(═O)$_2$—, —C(═O)O—, —OC(═O)—, —C(═O)NR—, —NRC(═O)—, —C(═O)S—, —SC(═O)—, OC(═O)O—, NRC(═O)O—, —OC(═O)NR—, and —NRC(═O)NR—;

$R_{11}$, $R_{12}$, $R_x$, $R_y$, $R_{14}$, $R_{15}$, $R_{16}$, and $R_{17}$ are each independently H or $C_1$-$C_6$ aliphatic;

R, $R_{13}$ and $R_{18}$ are each independently H or $C_1$-$C_6$ aliphatic;

$R_{19}$ is H, $C_1$-$C_6$ aliphatic, an amino protecting group, $L_3$-C(═O)—, or $A_2$;

$L_1$ and $L_2$ are each independently $C_5$-$C_{21}$ aliphatic or $C_4$-$C_{20}$ heteroaliphatic;

$L_3$ is $C_1$-$C_{21}$ aliphatic or $C_2$-$C_{20}$ heteroaliphatic;

$A_2$ is an amino acid or a peptide;

wherein any aliphatic or heteroaliphatic present in any of R, $R_{11}$, $R_{12}$, $R_{13}$, $R_{14}$, $R_{15}$, $R_{16}$, $R_{17}$, $R_{18}$, $R_{19}$, $R_x$, $R_y$, $L_1$, $L_2$, and $L_3$ is optionally substituted;

Y is

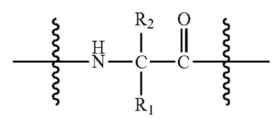

wherein:

$R_1$ and $R_2$ are independently selected from the group consisting of H, —$CH_2OH$, —$CH_2CH_2OH$, —CH($CH_3$)OH, —$CH_2OPO(OH)2$, —$CH_2C$(═O)$NH_2$, —$CH_2CH_2C$(═O)OH and —$CH_2CH_2C$(═O)$OR_8$, wherein any one of the alkyl hydrogens can be replaced with a halogen;

$R_8$ is selected from the group consisting of H and a straight or branched $C_1$-$C_6$ alkyl;

and

B represents a Polyethylene Glycol (PEG), wherein the PEG is a substituted PEG according to the following formula:

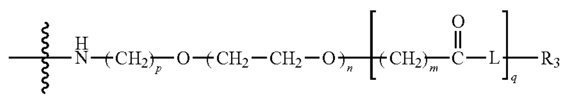

wherein n is 3 to 100;

m is 1, 2, 3, or 4;

p is 2, 3, or 4;

q is null or 1;

$R_3$ is H, —$NH_2$, or —OH, wherein when q is null, $R_3$ is H and when q is 1, $R_3$ is —$NH_2$ or —OH;

L is null or consists of 1 to 10 units, wherein each unit has the formula:

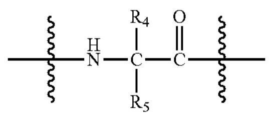

wherein $R_4$ is H; and $R_5$ is a side chain of an amino acid selected from: the 20 naturally occurring amino acids commonly designated by three letter symbols, 4-hydroxyproline, hydroxylysine, demosine, isodemosine, 3-methylhistidine, norvlin, beta-alanine, gamma-aminobutyric acid, citrulline, homocysteine, homoserine, ornithine, and methionine sulfone;

or a pharmaceutically acceptable salt, solvate or prodrug thereof.

2. The compound of claim 1, or a pharmaceutically acceptable salt, solvate or prodrug thereof, wherein q is 1.

3. The compound of claim 1, or a pharmaceutically acceptable salt, solvate or prodrug thereof, wherein n is from 10 to 14.

4. The compound of claim 3, or a pharmaceutically acceptable salt, solvate or prodrug thereof, wherein n is 11.

5. The compound of claim 1, or a pharmaceutically acceptable salt, solvate or prodrug thereof, wherein n is from 24 to 30.

6. The compound of claim 5, or a pharmaceutically acceptable salt, solvate or prodrug thereof, wherein n is 27.

7. The compound of claim 1, or a pharmaceutically acceptable salt, solvate or prodrug thereof, wherein m is from 1 to 3.

8. The compound of claim 7, or a pharmaceutically acceptable salt, solvate or prodrug thereof, wherein m is 2.

9. The compound of claim 1, or a pharmaceutically acceptable salt, solvate or prodrug thereof, wherein v is 2.

10. The compound of claim 1, or a pharmaceutically acceptable salt, solvate or prodrug thereof, wherein $R_x$, $R_y$, $R_{13}$, $R_{14}$, $R_{15}$, $R_{16}$, and $R_{17}$ are H.

11. The compound of claim 1, or a pharmaceutically acceptable salt, solvate or prodrug thereof, wherein $Z_1$ and $Z_2$ are the same and selected from the group consisting of —O—, —NR—, —S—, S(═O), S(═O)$_2$—, —C(═O)O—, —OC(═O)—, —C(═O)NR—, —NRC(═O)—, —C(═O)S—, —SC(═O)—, OC(═O)O—, NRC(═O)O—, —OC(═O)NR—, and —NRC(═O)NR—, wherein each R is independently H or $C_1$-$C_6$ aliphatic.

12. The compound according to claim 1, or a pharmaceutically acceptable salt, solvate or prodrug thereof, wherein the compound is the R stereoisomer of the compound around the chiral center denoted by *:

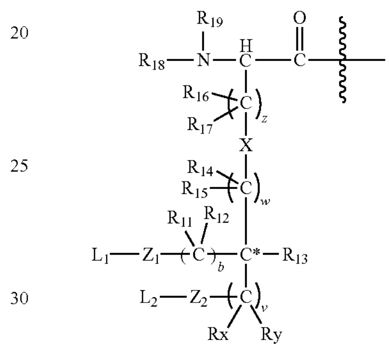

and/or wherein the chiral center denoted by ** in the following formula is in the L-configuration:

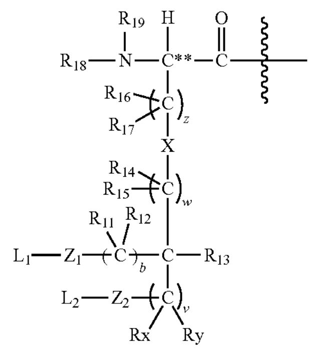

wherein the chiral center denoted by *** in the following formula is in the L-configuration:

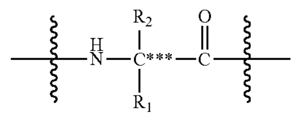

13. The compound according to claim 1 selected from any one of the following compounds:
| Compound Structure | Compound name |
| --- | --- |
| 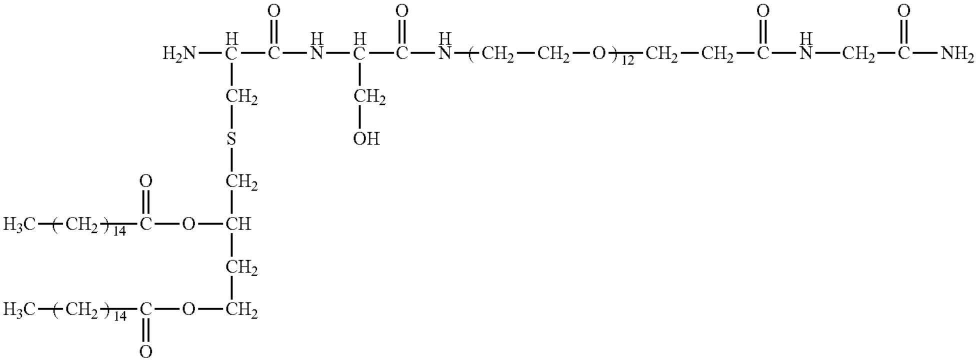 | Compound 1 |
| 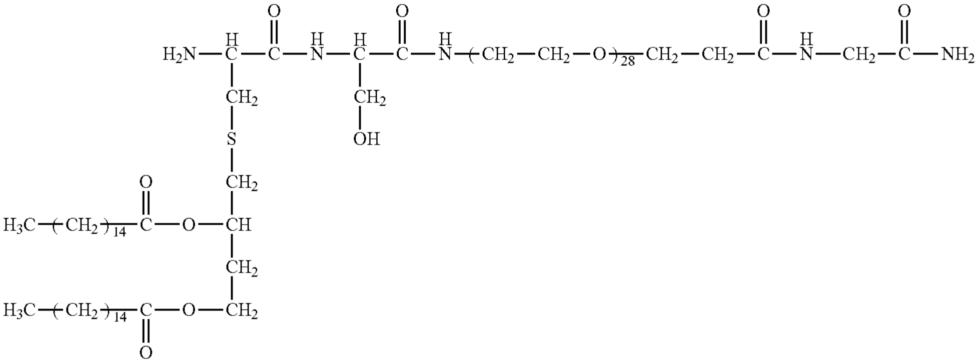 | Compound 2 |
| 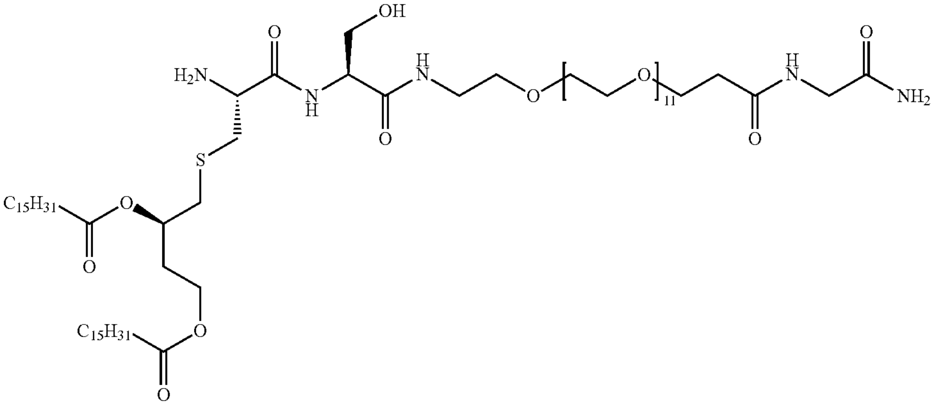 | Compound 3 |
| 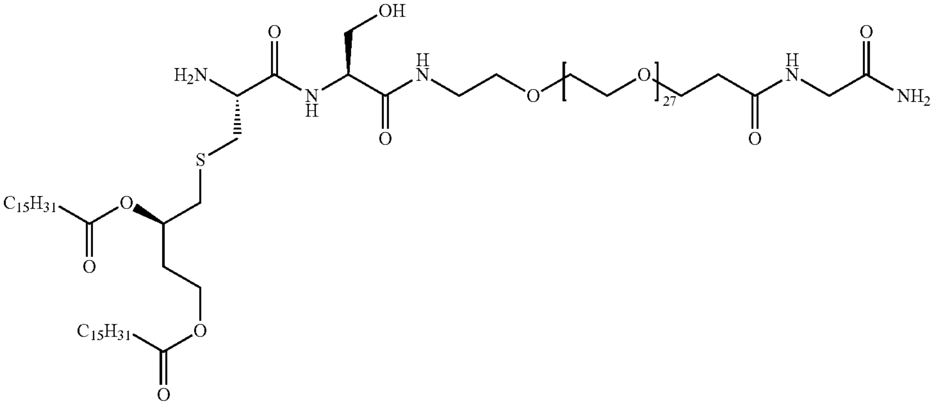 | Compound 4 |

-continued
| Compound Structure | Compound name |
|---|---|
| 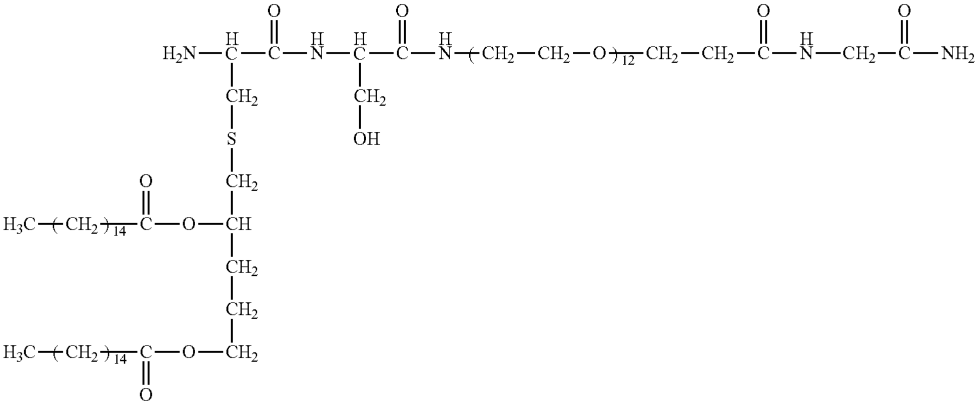 | Compound 5 |
| 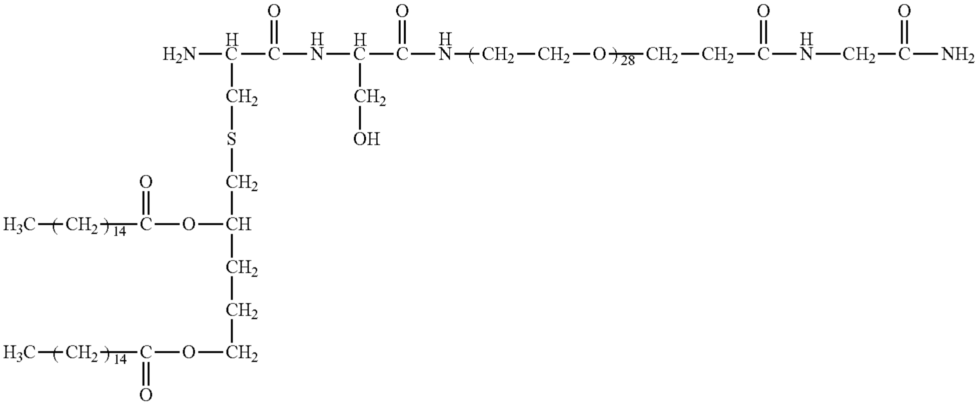 | Compound 6 |
| 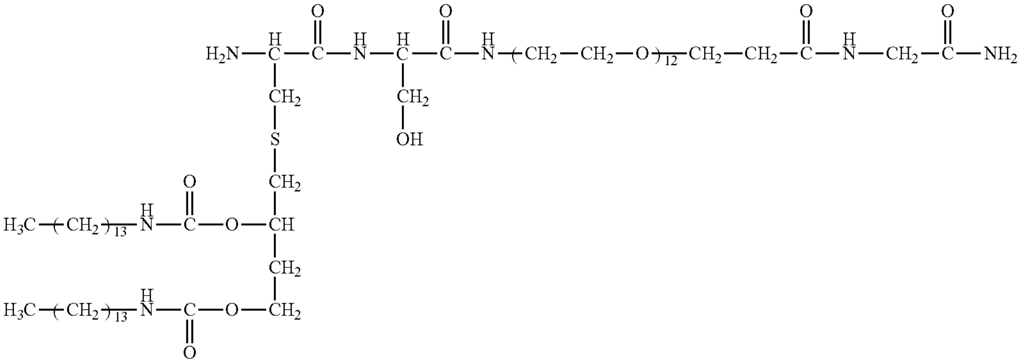 | Compound 7 |
| 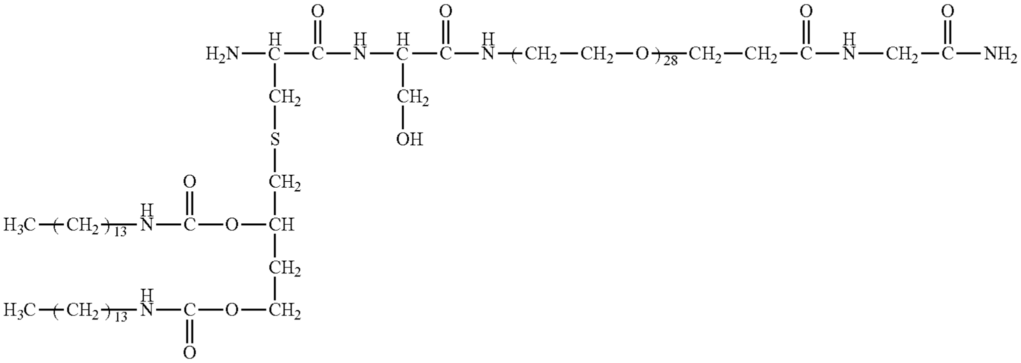 | Compound 8 |

-continued
| Compound Structure | Compound name |
|---|---|
| 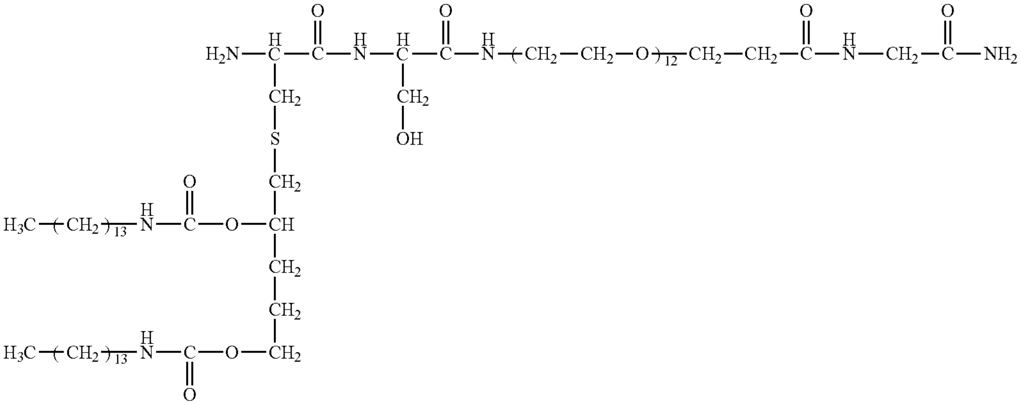 | Compound 9 |
| 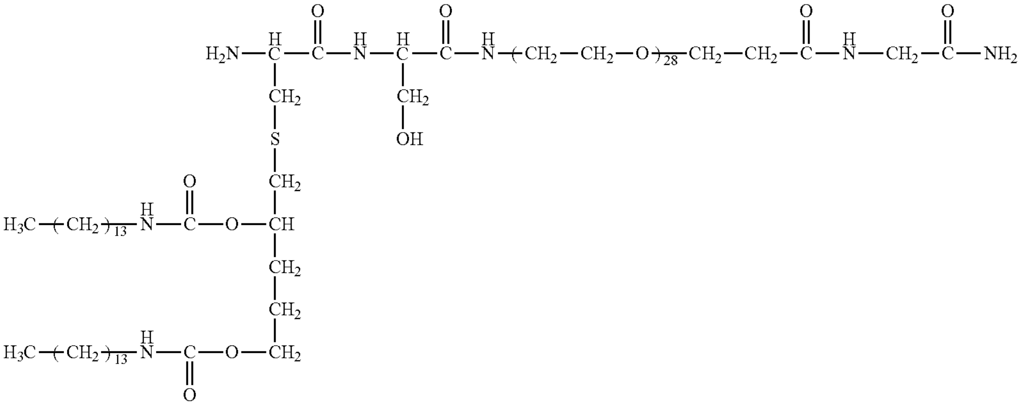 | Compound 10 |
| 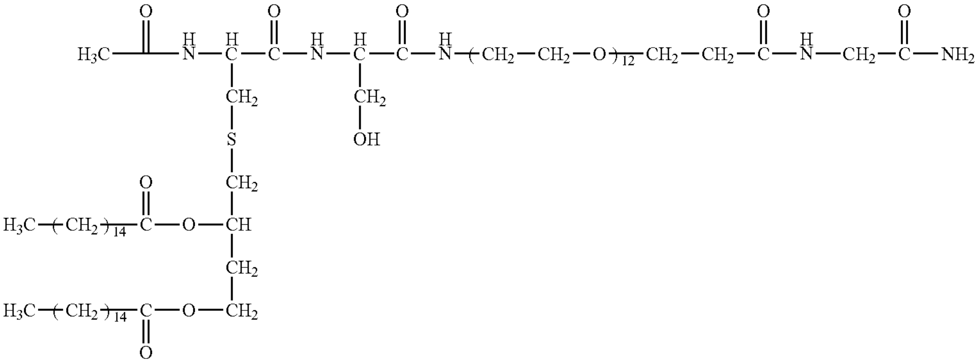 | Compound 11 |
| 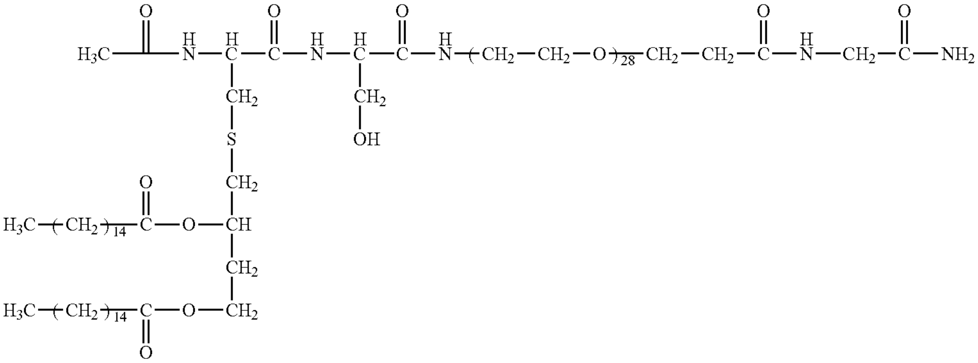 | Compound 12 |

-continued
| Compound Structure | Compound name |
| --- | --- |
| 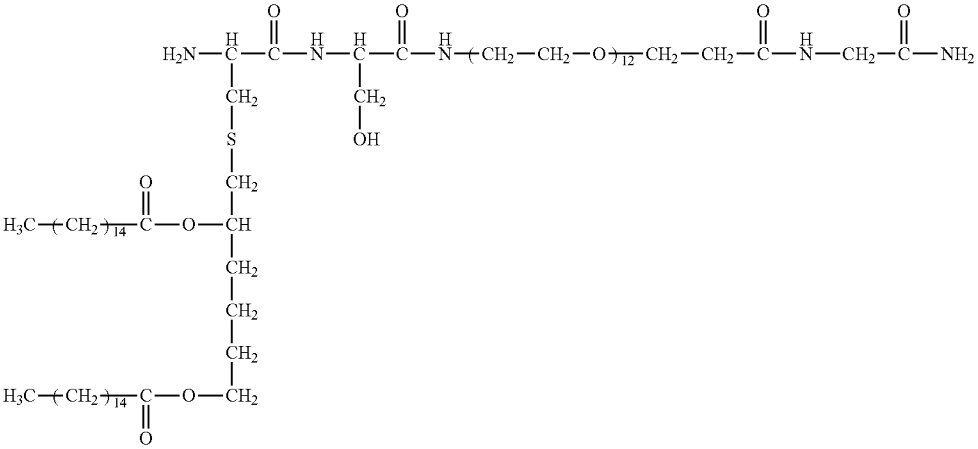 | Compound 13 |
| 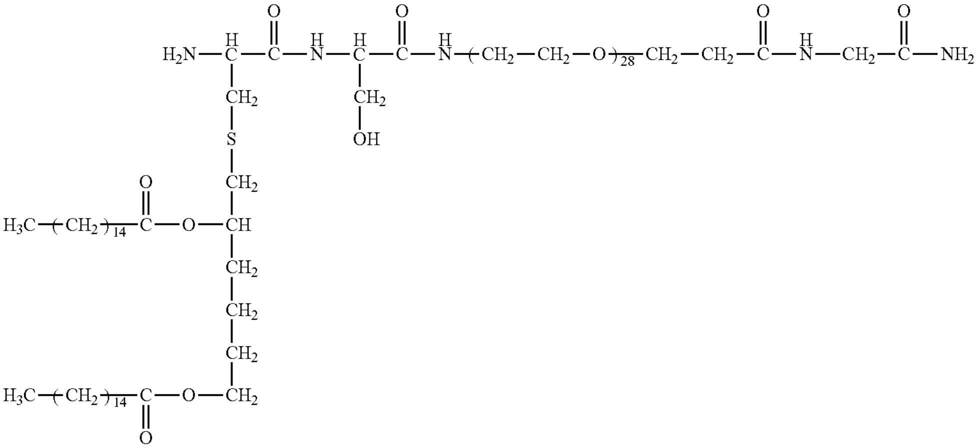 | Compound 14 |
| 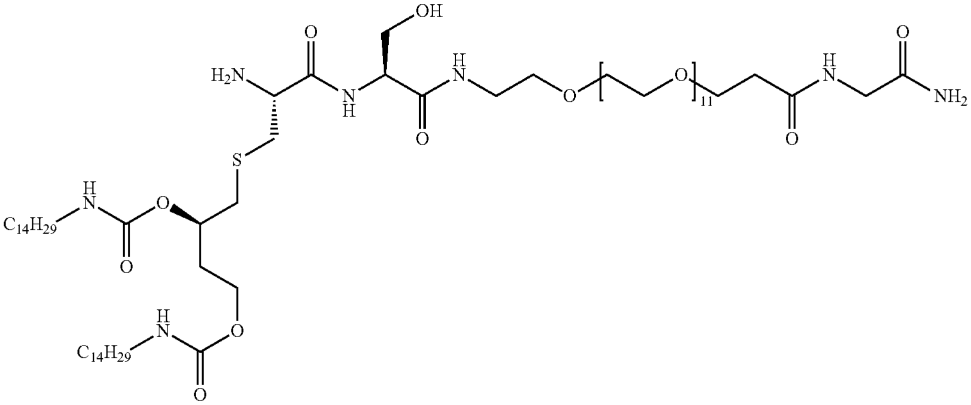 | Compound 15 |

-continued
| Compound Structure | Compound name |
| --- | --- |
| 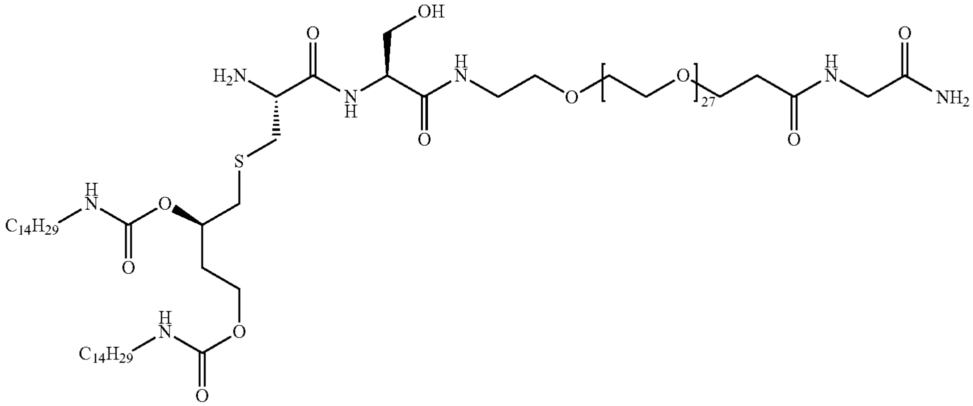 | Compound 16 |
| 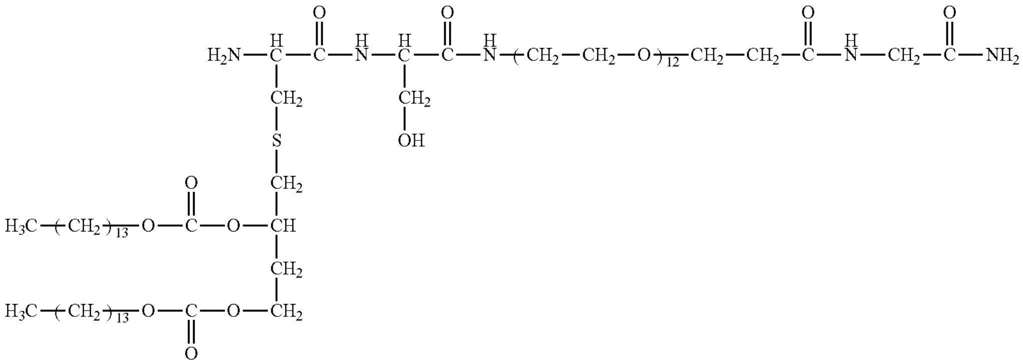 | Compound 17 |
| 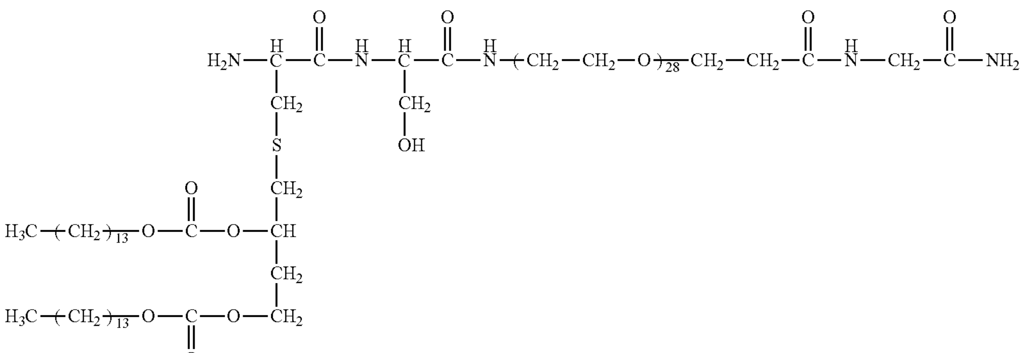 | Compound 18 |
| 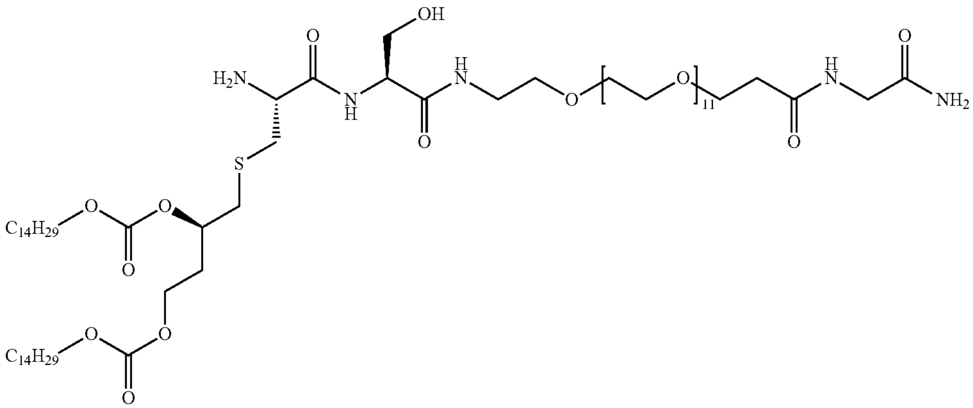 | Compound 19 |

-continued
| Compound Structure | Compound name |
| --- | --- |
| 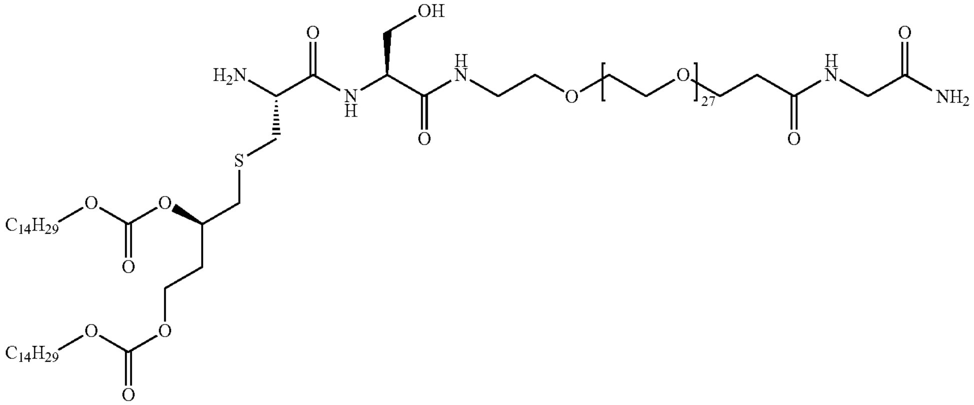 | Compound 20 |
| 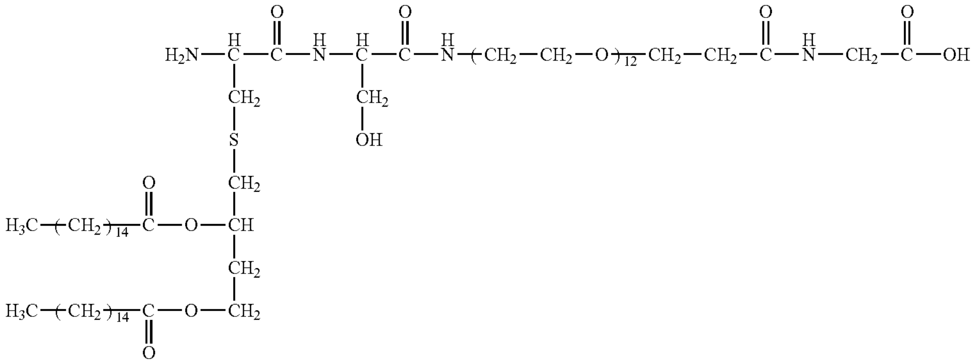 | Compound 21 |
| 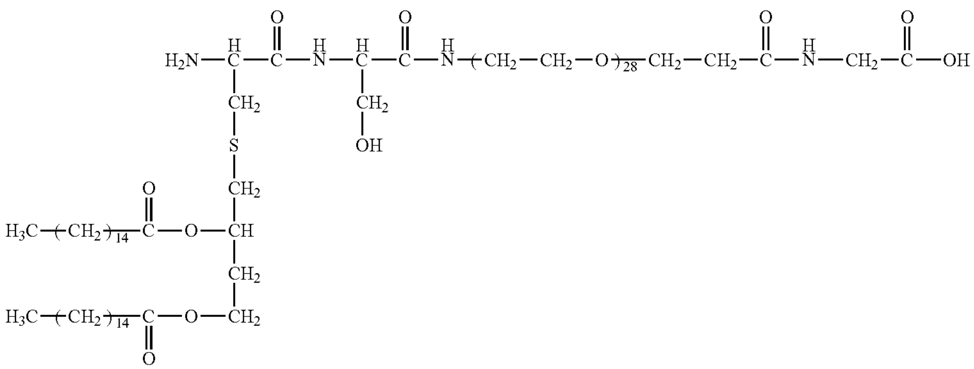 | Compound 22 |
| 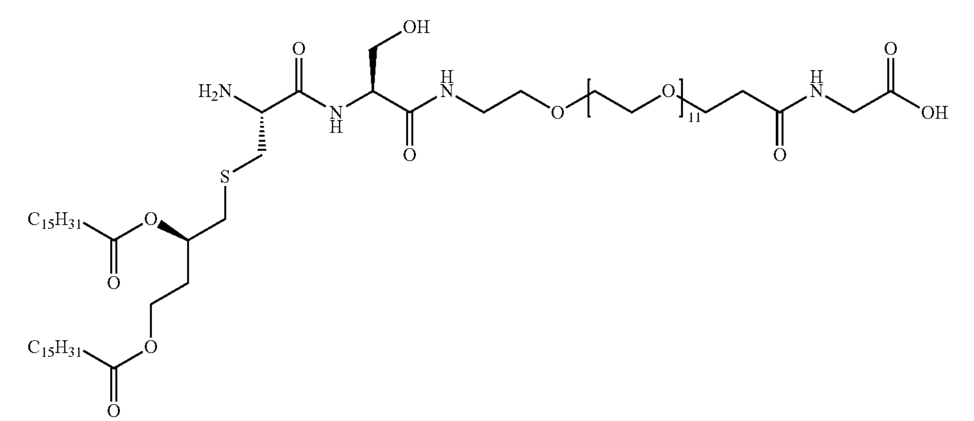 | Compound 23 |

-continued
| Compound Structure | Compound name |
| --- | --- |
| 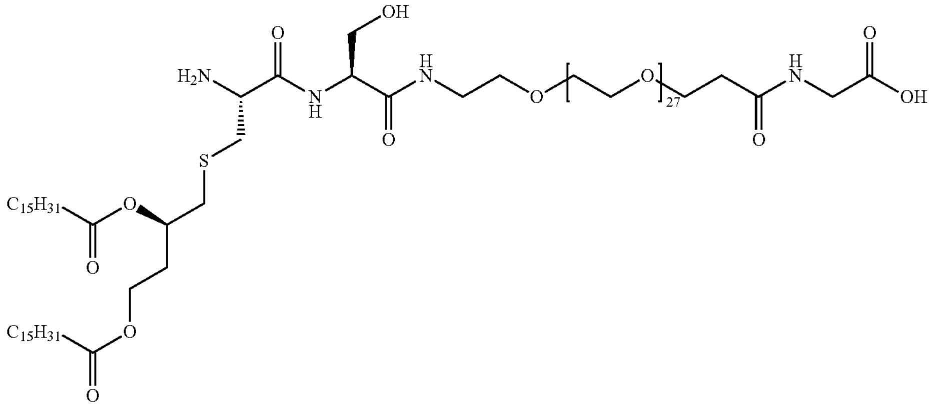 | Compound 24 |
| 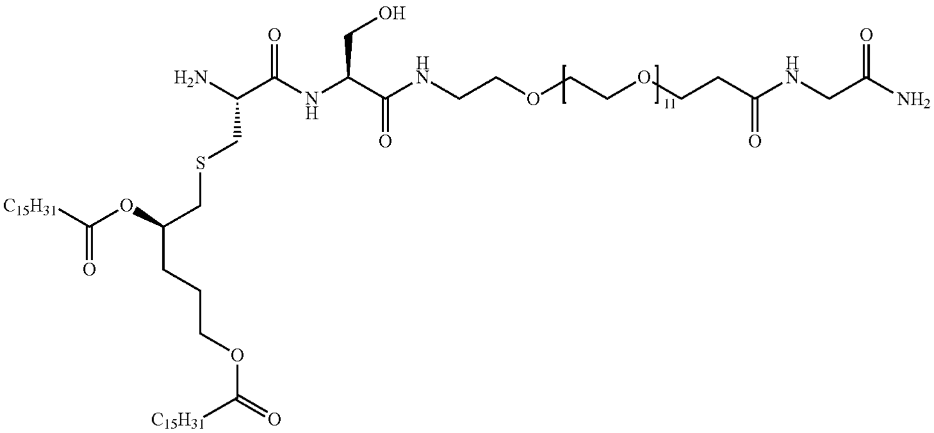 | Compound 25 |
| 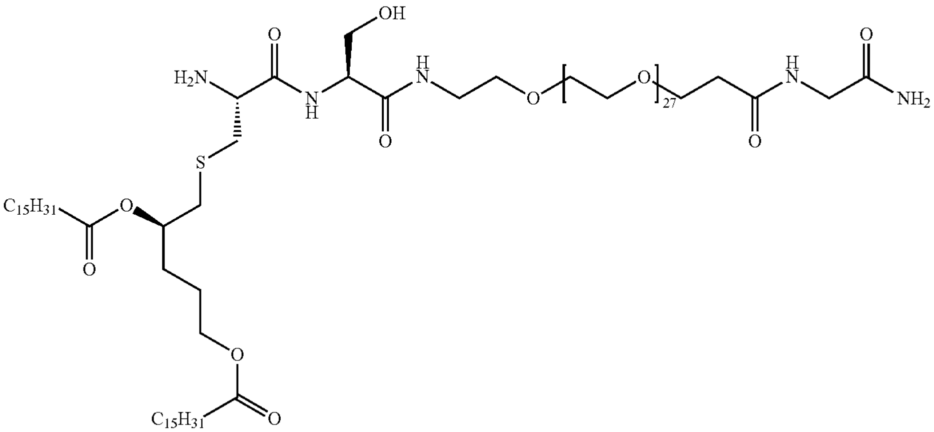 | Compound 26 |

-continued
| Compound Structure | Compound name |
|---|---|
| 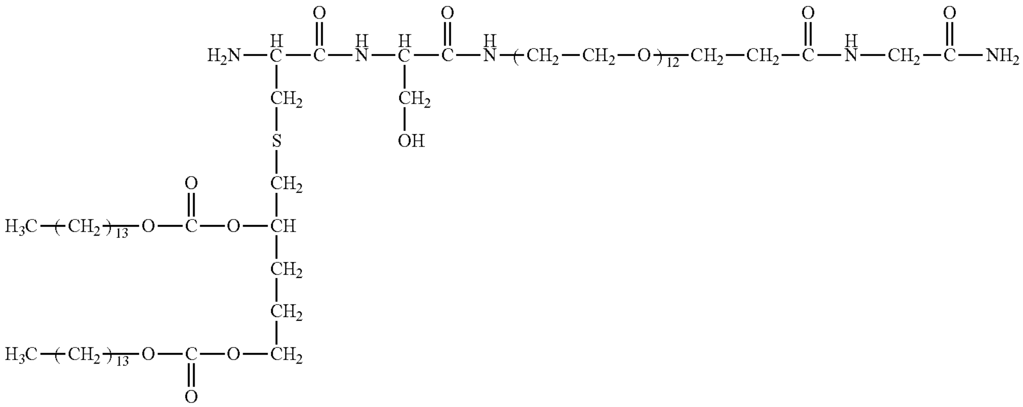 | Compound 27 |
| 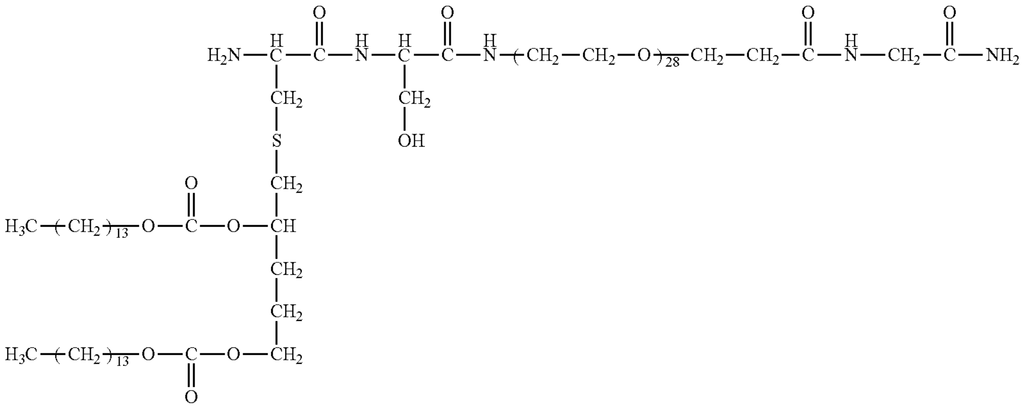 | Compound 28 |
| 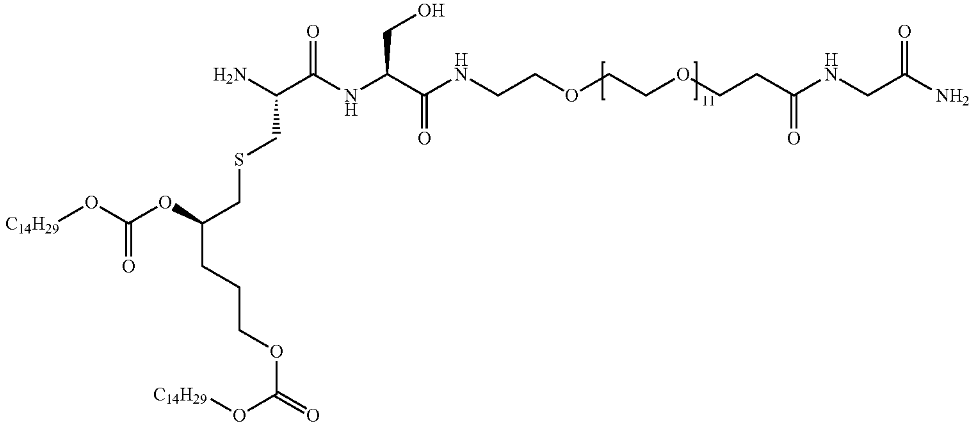 | Compound 29 |

-continued
| Compound Structure | Compound name |
|---|---|
| 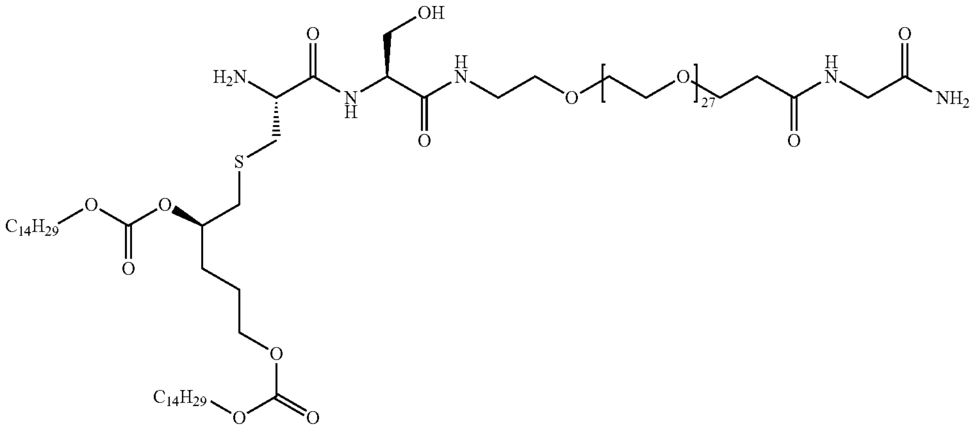 | Compound 30 |
| 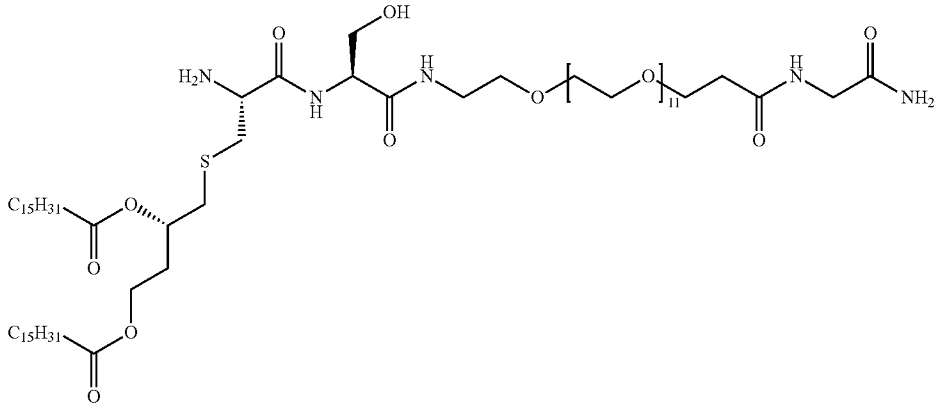 | Compound 31 |
| 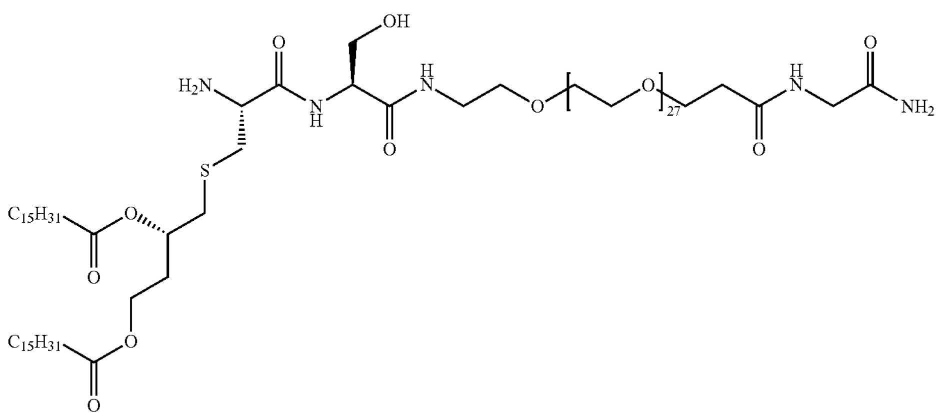 | Compound 32 |

-continued
| Compound Structure | Compound name |
|---|---|
| 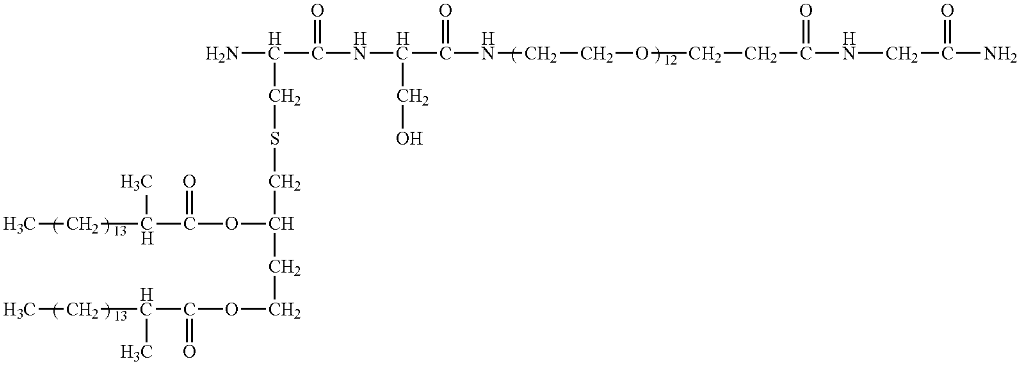 | Compound 33 |
| 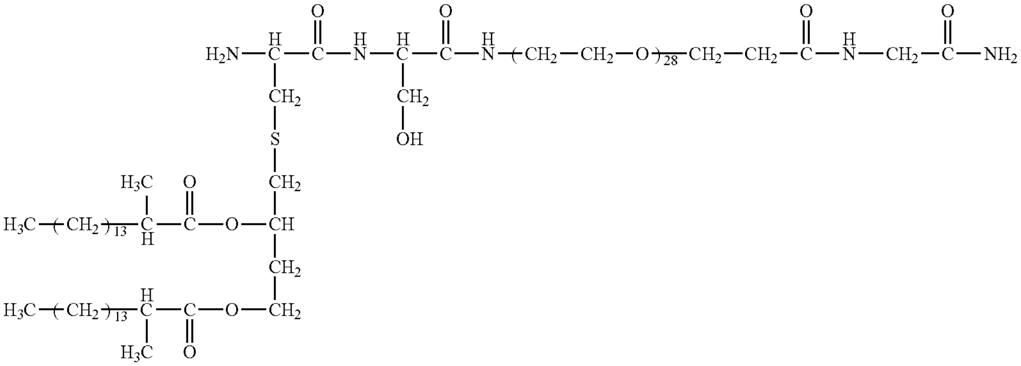 | Compound 34 |
| 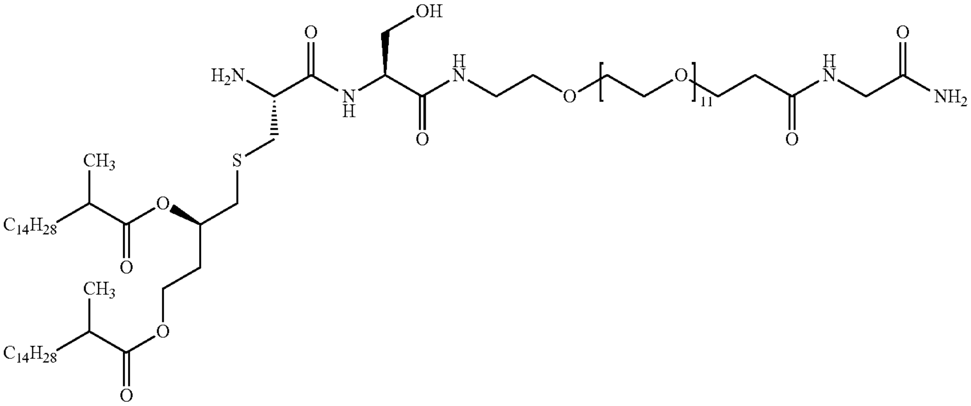 | Compound 35 |
| 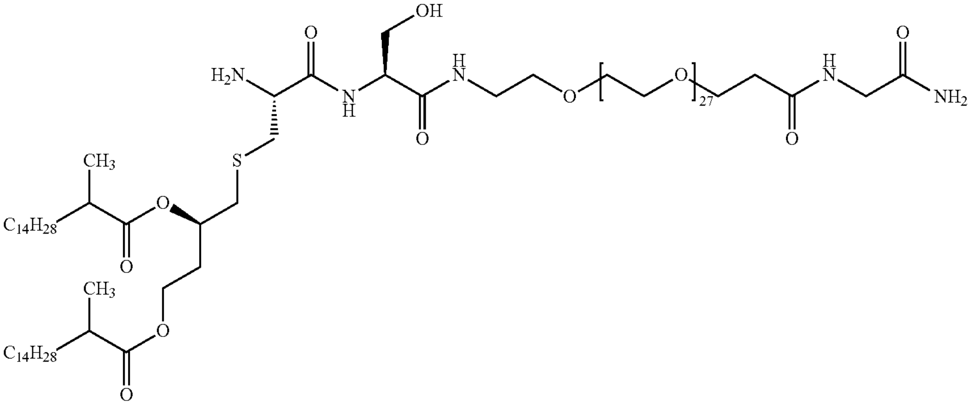 | Compound 36 |

or a pharmaceutically acceptable salt, solvate or prodrug thereof.

14. A composition comprising a compound of claim 1, or a pharmaceutically acceptable salt, solvate or prodrug thereof, and a pharmaceutically acceptable carrier, diluent or excipient.

15. A method of treating a disease, comprising raising an innate immune response in a subject by administering an effective amount of a compound of claim 1, or a pharmaceutically acceptable salt, solvate or prodrug thereof to the subject in need thereof.

16. The method of claim 15, wherein the disease is selected from one or more of a disease caused by an infectious agent, a respiratory disease or condition associated with a viral or bacterial infection, and a respiratory infection.

17. The method of claim 15, which is a method for reducing airway inflammation.

18. The method of claim 17, wherein the method further comprises the step of identifying a subject having a respiratory disease or condition.

19. The method of claim 18, wherein the respiratory disease or condition is not a rhinovirus infection.

20. The compound of claim 1, or a pharmaceutically acceptable salt, solvate or prodrug thereof, wherein $R_5$ is H.

* * * * *